United States Patent
Howell et al.

(10) Patent No.: US 11,806,164 B2
(45) Date of Patent: *Nov. 7, 2023

(54) METHOD AND APPARATUS FOR HEALTH CONDITION OF A PERSON BASED ON BODILY FLUID

(71) Applicant: IpVenture, Inc., San Jose, CA (US)

(72) Inventors: Thomas A. Howell, Palo Alto, CA (US); Angeline Hadiwidjaja, Los Altos, CA (US); Peter P. Tong, Mountain View, CA (US); C. Douglass Thomas, Saratoga, CA (US)

(73) Assignee: IpVenture, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/724,816

(22) Filed: Apr. 20, 2022

(65) Prior Publication Data
US 2022/0240850 A1    Aug. 4, 2022

Related U.S. Application Data

(63) Continuation of application No. 17/211,977, filed on Mar. 25, 2021, now Pat. No. 11,337,650, which is a
(Continued)

(51) Int. Cl.
*A61B 5/00*    (2006.01)
*A61B 10/00*    (2006.01)
(Continued)

(52) U.S. Cl.
CPC .............. *A61B 5/4875* (2013.01); *A61B 5/01* (2013.01); *A61B 5/14507* (2013.01);
(Continued)

(58) Field of Classification Search
CPC ... A61B 5/4875; A61B 5/682; A61B 10/0045; A61B 5/4869; A61B 5/6814; A61B 10/0051

See application file for complete search history.

(56) References Cited

U.S. PATENT DOCUMENTS 3,420,205 A    1/1969  Morison
4,126,132 A    11/1978 Portner et al.
(Continued)

FOREIGN PATENT DOCUMENTS

EP    0 274 363 B1    7/1988
EP    1 184 663 A3    3/2000
(Continued)

OTHER PUBLICATIONS

"Comparison of a New Test for the Measurement of Resting Whole Saliva with the Draining and the Swab Techniques", Pia López-Jornet et al., Department of Oral Medicine, University of Murcia, Murcia, Spain, electronic publication: Feb. 1997, 6 pages.

(Continued)

*Primary Examiner* — Jon Eric C Morales

(57) ABSTRACT

In one embodiment, a hydration sensor or sensing element is configured to measure the hydration level of a user. The sensing element can include a water-permeable material positioned in between two water-impermeable material. The sensing element can be coupled to a bottle of fluid, or a carrier with a timer. The sensing element can be incorporated into a handheld device. The sensing element can be a disposable element, an element applicable for more than one-time use, or a re-usable element. The sensing element or sensor can be calibrated for a specific user or a group of users. One or more additional sensors that do not measure hydration level of the user can be coupled to a hydration sensing element to determine the amount of fluid consumption for the user in different conditions.

17 Claims, 51 Drawing Sheets

Related U.S. Application Data continuation of application No. 16/270,773, filed on Feb. 8, 2019, now Pat. No. 11,013,461, which is a continuation of application No. 15/231,292, filed on Aug. 8, 2016, now Pat. No. 10,258,278, which is a continuation-in-part of application No. 14/279,483, filed on May 16, 2014, now abandoned, which is a continuation of application No. 11/592,431, filed on Nov. 2, 2006, now Pat. No. 8,734,341, which is a continuation-in-part of application No. 11/451,781, filed on Jun. 12, 2006, now abandoned, said application No. 11/592,431 is a continuation-in-part of application No. 11/314,545, filed on Dec. 20, 2005, now abandoned.

(60) Provisional application No. 62/256,901, filed on Nov. 18, 2015, provisional application No. 60/785,825, filed on Mar. 24, 2006, provisional application No. 60/732,925, filed on Nov. 2, 2005, provisional application No. 60/689,312, filed on Jun. 10, 2005, provisional application No. 60/670,957, filed on Apr. 13, 2005, provisional application No. 60/652,213, filed on Feb. 14, 2005, provisional application No. 60/636,969, filed on Dec. 20, 2004.

(51) Int. Cl.
  *G01N 21/78* (2006.01)
  *G01N 37/00* (2006.01)
  *A61B 5/01* (2006.01)
  *A61B 5/145* (2006.01)

(52) U.S. Cl.
  CPC ............ *A61B 5/443* (2013.01); *A61B 5/0008* (2013.01); *A61B 5/681* (2013.01); *A61B 5/682* (2013.01); *A61B 5/6887* (2013.01); *A61B 10/0051* (2013.01)

(56) References Cited

U.S. PATENT DOCUMENTS

| | | |
|---|---|---|
| 4,513,608 A | 4/1985 | Cuming |
| 4,860,753 A | 8/1989 | Amerena |
| 4,883,063 A | 11/1989 | Bernard et al. |
| 5,014,798 A | 5/1991 | Glynn |
| 5,231,993 A | 8/1993 | Haber et al. |
| 5,353,802 A | 10/1994 | Ollmar |
| 5,426,415 A | 6/1995 | Prachar et al. |
| 5,495,961 A | 3/1996 | Maestre |
| 5,563,584 A | 10/1996 | Rader et al. |
| 5,580,794 A | 12/1996 | Allen |
| 5,755,672 A | 5/1998 | Arai et al. |
| 5,833,625 A | 11/1998 | Essen-Moller |
| 5,843,691 A | 12/1998 | Douglas et al. |
| 5,938,593 A | 8/1999 | Ouellette |
| 5,980,498 A | 11/1999 | Brown et al. |
| 6,107,537 A | 8/2000 | Elder et al. |
| 6,248,067 B1 | 6/2001 | Causey, III et al. |
| 6,319,199 B1 | 11/2001 | Sheehan et al. |
| 6,370,426 B1 | 4/2002 | Campbell et al. |
| 6,466,821 B1 | 10/2002 | Pianca et al. |
| 6,485,982 B1 | 11/2002 | Charlton |
| 6,523,392 B2 | 2/2003 | Porter et al. |
| 6,529,446 B1 | 3/2003 | de la Huerga |
| 6,529,767 B1 | 3/2003 | Woo et al. |
| 6,569,094 B2 | 5/2003 | Suzuki et al. |
| 6,602,469 B1 | 8/2003 | Maus et al. |
| 6,623,698 B2 | 9/2003 | Kuo |
| 6,766,817 B2 | 7/2004 | da Silva |
| 6,780,307 B2 | 8/2004 | Kidwell |
| 6,823,717 B2 | 11/2004 | Porter et al. |
| 6,854,317 B2 | 2/2005 | Porter et al. |
| 6,998,273 B1 | 2/2006 | Fleming et al. |
| 7,170,823 B2 | 1/2007 | Fabricius et al. |
| 7,273,454 B2 | 9/2007 | Raymond et al. |
| 7,323,141 B2 | 1/2008 | Kirchhevel et al. |
| 7,332,642 B2 | 2/2008 | Liu |
| 8,118,740 B2 | 2/2012 | Howell et al. |
| 8,734,341 B2 | 5/2014 | Howell et al. |
| 10,258,278 B2 | 4/2019 | Howell et al. |
| 11,013,461 B2 * | 5/2021 | Howell ............... A61B 5/4875 |
| 11,337,650 B2 | 5/2022 | Howell et al. |
| 2002/0001852 A1 | 1/2002 | Mendel-Hartvig et al. |
| 2002/0147617 A1 | 10/2002 | Schoenbaum et al. |
| 2003/0002238 A1 | 1/2003 | Toyoda |
| 2004/0121478 A1 | 6/2004 | Brinz et al. |
| 2004/0133081 A1 | 7/2004 | Teller et al. |
| 2005/0033200 A1 | 2/2005 | Soehren et al. |
| 2005/0143675 A1 | 6/2005 | Neel et al. |
| 2005/0169810 A1 | 8/2005 | Hagen et al. |
| 2005/0228692 A1 | 10/2005 | Hodgdon |
| 2006/0121548 A1 | 6/2006 | Robbins et al. |
| 2006/0231109 A1 | 10/2006 | Howell et al. |
| 2006/0241355 A1 | 10/2006 | Howell et al. |
| 2006/0248946 A1 | 11/2006 | Howell et al. |
| 2006/0278156 A1 | 12/2006 | Miller |
| 2007/0024465 A1 | 2/2007 | Howell et al. |
| 2007/0048224 A1 | 3/2007 | Howell et al. |
| 2007/0213606 A1 | 9/2007 | Sherman et al. |
| 2007/0225578 A1 | 9/2007 | Howell et al. |
| 2007/0249059 A1 | 10/2007 | Stewart |
| 2008/0025154 A1 | 1/2008 | MacDonald et al. |
| 2008/0146890 A1 | 6/2008 | LeBoeuf et al. |
| 2014/0249388 A1 | 9/2014 | Howell et al. |
| 2017/0027506 A1 | 2/2017 | Howell et al. |
| 2019/0246976 A1 | 8/2019 | Howell et al. |
| 2021/0204875 A1 | 7/2021 | Howell et al. |

FOREIGN PATENT DOCUMENTS

| | | |
|---|---|---|
| GB | 855916 | 12/1960 |
| WO | WO 2005084531 A1 | 9/2005 |

OTHER PUBLICATIONS

"Hydration status measurement by radio frequency absorptiometry in young athletes, a new method and preliminary results," Daniel S. Moran et al., IoP electronic journals, Physiological Measurement, Feb. 2004, pp. 51-59.

"Sensing device that when implanted in the mouth can detect hydration levels in soldiers", News-Medical.net, Devices/Technology, May 18, 2004, 3 pages.

"Xerostomia Information for dentists, Helping patients with dry mouth", Bartels, Cathy L., http://www.oralcancerfoundation.org/dental/xerostomia.htm, downloaded Mar. 22, 2007, pp. 1-14.

"0136 A new method to measure viscosity in saliva", Becker, K., et al., http://iadr.confex.com/iadr/eur05/techprogram/abstract_67646.htm, downloaded Oct. 14, 2005, p. 1.

Biode, Technical White Paper #1, (undated) downloaded Dec. 6, 2006, pp. 1-2.

Brownlee, Christen, "Oral Exams, Saliva could provide an alternative for some diagnostic tests," www.sciencenews.org, vol. 168, Sep. 17, 2005, pp. 187-188.

Cambridge Viscometers: Accurate, Reliable and Proven Fluid Viscosity Measurement Technology, http://www.cambridgeviscosity.com/default.aspx, downloaded Dec. 6, 2006, p. 1.

Bossingham, et al. "Water balance, hydration status, and fat-free mass hydration in younger and older adults," Am. J. Clin. Nutr, 81, 2005, 1342-1350.

Casa, D.J. et al. "National Athletic Trainers' Association Position Statement: Fluid Replacement for Athletes," Journal of Athletic Training, 2003, vol. 35, No. 2, pp. 212-224.

Marketing Devices, http://www.courage-khazaka.de/products/marketing_products.htm, downloaded May 14, 2007, pp. 1-4.

Products for Dermatology, http://www.courage-khazaka.de/products/derma_products.htm, downloaded May 14, 2007, pp. 1-4.

(56) References Cited

OTHER PUBLICATIONS

Scientific Devices, http://www.courage-khazaka.de/products/scientific_rd_prod.htm, downloaded May 14, 2007, pp. 1-5.
E-pill Pill Bottle Multi Alarm, http://www.epill.com/bottle.html, downloaded Dec. 5, 2006.
Étude, "The Way to skin counseling," Operation Manual, 2005, front cover page and pp. 1-27.
Gojo Skin Care Lab, Fast, Effective Hand Cleaning, http://automotive.gojo.com/skin_care/, downloaded Nov. 29, 2006, pp. 1-2.
Helton, K.L. et al. "Interfacial instabilities affect microfluidic extraction of small molecules from non-Newtonian fluids," Lab Chip, 2007, 7, 1581-1588.
Kenney, et al. "Influence of age on thirst and fluid intake," Medicine & Science in Sports & Exercise, Official Journal of the American College of Sports Medicine, vol. 33, No. 9, 2001, 1524-1532.
"L'Oréal and STMicroelectronics applying semiconductors to skin aging," Press Release, Geneva, Oct. 18, 2002, pp. 2.
LifePoint Inc.—Saliva Based Testing Systems for the next generation, LifePoint® IMPACT® Test System, downloaded 2005, 2 pages.
Moritex USA Incorporated, Sensors & Meters, copyright 2004, http://www.moritexusa.com/products/product_category.php?plid=5&pcid=10, downloaded Apr. 19, 2006, pp. 1-2.
Mentes, Janet, PhD, APRN, BC, "Oral Hydration in Older Adults," AJN, vol. 106, No. 6, Jun. 2006, 40-49.
Murray, R. "Dehydration, Hyperthermia, and Athletes: Science and Practice," Journal of Athletic Training, vol. 31, No. 3, Sep. 1996, 248-249.
NELLCOR™ Oximax Sensors™, Tyco Healthcare Group, 2002, pp. 1-5.
Nellcor OxiMax, Sensor Selection Guide, Tyco Healthcare, Oct. 2002, 12 pages.
Principal of Operation (viscosity measurement), Norcross Corporation, http://www.viscosity.com/faq_poo.asp., downloaded Nov. 8, 2007, 1 page.
Cheuvront, S.N. et al. "Hydration Assessment of Athletes," Sports Science Exchange 97, vol. 18, No. 2, 2005, p. 1-12.
Prince, R. "A disposable, self-administered Electrolyte Test," submitted to the Department of Electrical Engineering and Computer Science in partial fulfillment of the requirements for the degree of Master of Engineering in Electrical Engineering at the Massachusetts Institute of Technology, Feb. 2003, pp. 13-17.
Rener-Nantz J. in Current Protocols in Food Analytical Chemistry (2001) H1.3.1-H1.3.5, 2001 by John Wiley * Sons, Inc.
Sikdar, S. et al. In "Viscosity Measurements of Non-Newtonian Slurry Suspensions Using Rotating Viscometers," Ind. Eng. Chem. Process Des. Dev., vol. 18, No. 4, 1979, p. 722-726.
Sorbero et al. Assessment of Pay-for-Performance Options for Medicare Physician Services: Final Report. RAND Health. May 2006.
Walsh, N.P. et al. "Saliva flow rate, total protein concentration and osmolality as potential markers of who body hydration status during progressive acute dehydration in humans," Archives of Oral Biology (2004) 49, 149-154.
Walsh, N.P. et al. "Saliva Parameters as Potential Indices of Hydration Status during Acute Dehydration," Med. Sci. Sports, Exerc., v. 36, No. 9, pp. 1535-1542, 2004.
First Office Action for CN Patent Application No. 200610150494.7.
Second Office Action for CN Patent Application No. 200610150494.7.
Third Office Action for CN Patent Application No. 200610150494.7.
Notice of Grant of Patent Right for CN Patent Application No. 200610150494.7, dated Jun. 30, 2011.
U.S. Appl. No. 11/314,545, filed Dec. 20, 2005.
U.S. Appl. No. 11/888,723, filed Sep. 2, 2007.
Non-Final Office Action for U.S. Appl. No. 11/888,723, dated Feb. 15, 2012.
U.S. Appl. No. 11/821,150, filed Jun. 22, 2007.
Notice of Allowance for U.S. Appl. No. 11/592,431, dated Nov. 27, 2013.
Office Action for U.S. Appl. No. 11/592,431, dated Nov. 29, 2011.
Office Action for U.S. Appl. No. 11/592,431, dated Aug. 15, 2011.
Office Action for U.S. Appl. No. 11/592,431, dated May 13, 2011.
Office Action for U.S. Appl. No. 11/592,431, dated Dec. 3, 2010.
Restriction Requirement for U.S. Appl. No. 11/592,431, dated Oct. 19, 2010.
Office Action for U.S. Appl. No. 15/231,292, dated May 17, 2018.
Office Action for U.S. Appl. No. 16/270,773, dated May 6, 2020.
Notice of Allowance for U.S. Appl. No. 16/270,773, dated Nov. 27, 2020.
Notice of Allowance for U.S. Appl. No. 16/270,773, dated Mar. 2, 2021.
Office Action for U.S. Appl. No. 17/211,977, dated Jan. 26, 2022.
Notice of Allowance for U.S. Appl. No. 17/211,977, dated Feb. 28, 2022.
Complaint for Patent Infringement, *IpVenture, Inc. v. MX3 Diagnostics, Inc.*, WDTX, CA No. 6:21-cv-00713, filed Jul. 9, 2021, pp. 1-116.
First Amended Complaint for Patent Infringement, *IpVenture, Inc. v. MX3 Diagnostics, Inc.*, WDTX, CA No. 6:21-cv-00713, filed Sep. 28, 2021, pp. 1-12.
Order Granting Joint Motion to Dismiss, *IpVenture, Inc. v. MX3 Diagnostics, Inc.*, WDTX, CA No. 6:21-cv-00713, filed Jan. 20, 2022, p. 1.
Complaint for Declaratory Judgement of Non-Infringement of U.S. Pat. No. 11,337,650 (Exhibits included), *MX3 v. IpVenture, Inc.*, NDCA, CA No. 3:22-cv-04466, filed Aug. 2, 2022, pp. 1-121.
MX Diagnostics, Inc.'s, Supplemental Preliminary Invalidity Contentions, *IpVenture, Inc. v. MX3 Diagnostics, Inc.*, WDTX, CA No. 3:22-cv-4466-WHO, filed Mar. 28, 2023, pp. 1-24.

* cited by examiner

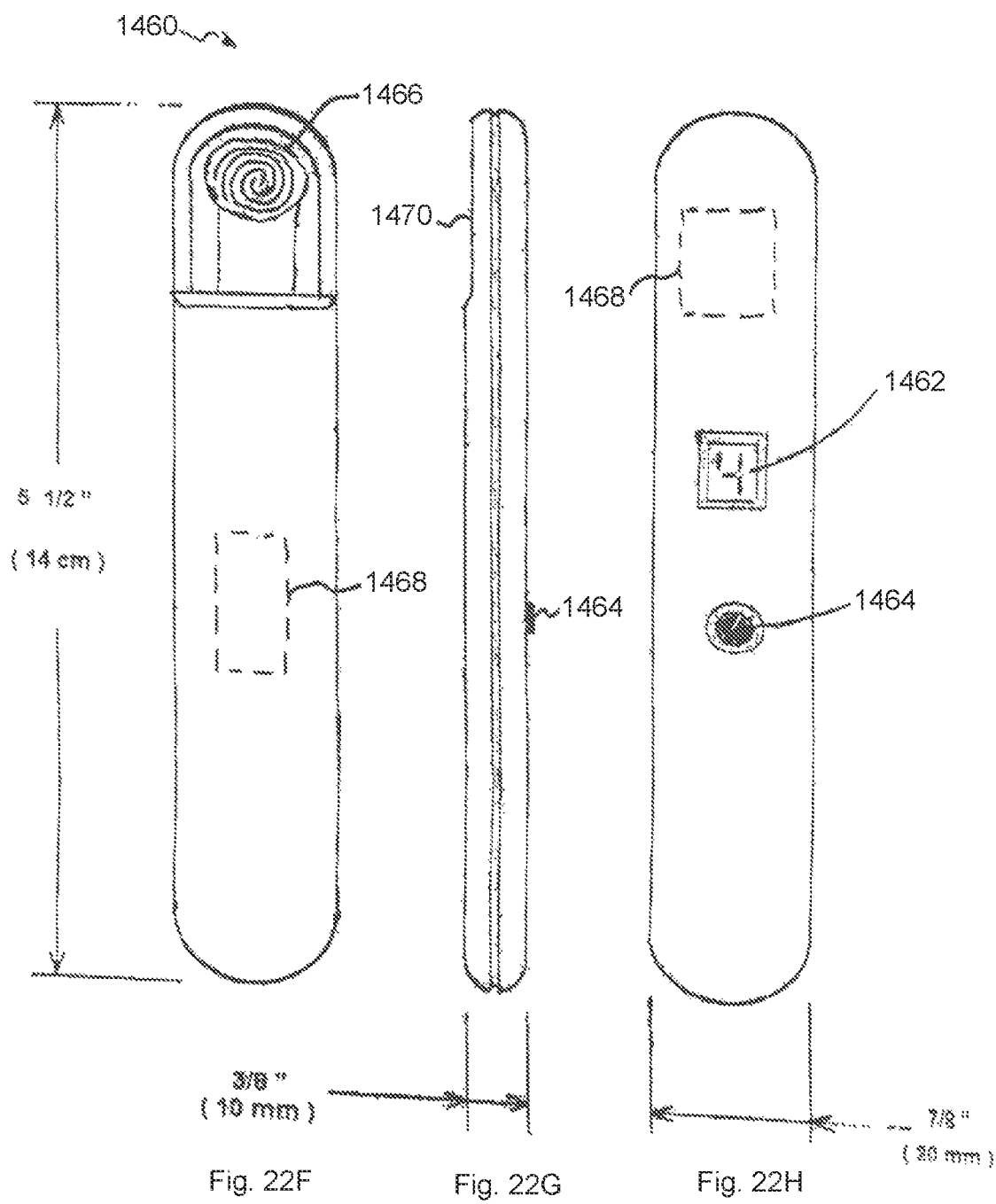

METHOD AND APPARATUS FOR HEALTH CONDITION OF A PERSON BASED ON BODILY FLUID

CROSS-REFERENCE TO RELATED APPLICATIONS

This application is a continuation of U.S. patent application Ser. No. 17/211,977, now U.S. Pat. No. 11,337,650, filed Mar. 25, 2021, and entitled "METHOD AND APPARATUS FOR HYDRATION LEVEL OF A PERSON," which is hereby incorporated by reference, which application is a continuation of U.S. patent application Ser. No. 16/270,773, now U.S. Pat. No. 11,013,461, filed Feb. 8, 2019, and entitled "METHOD AND APPARATUS FOR HYDRATION LEVEL OF A PERSON," which is hereby incorporated by reference, which application is a continuation of U.S. patent application Ser. No. 15/231,292, filed Aug. 8, 2016, now U.S. Pat. No. 10,258,278, and entitled "METHOD AND APPARATUS TO SENSE HYDRATION LEVEL OF A PERSON," which is hereby incorporated by reference, which application claims priority to U.S. Provisional Patent Application No. 62/256,901, filed Nov. 18, 2015, and entitled "METHOD AND APPARATUS TO SENSE HYDRATION LEVEL," which is hereby incorporated by reference.

U.S. patent application Ser. No. 15/231,292, is also a continuation-in-part of U.S. patent application Ser. No. 14/279,483, filed May 16, 2014, and entitled "METHOD AND APPARATUS TO SENSE HYDRATION LEVEL OF A PERSON," which is hereby incorporated by reference, which application is a continuation of U.S. patent application Ser. No. 11/592,431, filed Nov. 2, 2006, now U.S. Pat. No. 8,734,341, and entitled "METHOD AND APPARATUS TO SENSE HYDRATION LEVEL OF A PERSON," which is hereby incorporated by reference, and which application is continuation-in-part of U.S. patent application Ser. No. 11/314,545, filed Dec. 20, 2005, and entitled "BOTTLE OF LOTION WITH A SENSOR," which is hereby incorporated herein by reference, which claims priority to each of: (i) U.S. Provisional Patent Application No. 60/636,969, filed Dec. 20, 2004, entitled "PREVENTIVE MEDICAL SYSTEMS, METHODS AND APPARATUS," and which is hereby incorporated herein by reference; (ii) U.S. Provisional Patent Application No. 60/652,213, filed Feb. 14, 2005, entitled "PREVENTIVE MEDICAL SYSTEMS, METHODS AND APPARATUS," and which is hereby incorporated herein by reference; (iii) U.S. Provisional Patent Application No. 60/670,957, filed Apr. 13, 2005, entitled "BOTTLE OF LOTION WITH A LOTION SENSOR," and which is hereby incorporated herein by reference; (iv) U.S. Provisional Patent Application No. 60/689,312, filed Jun. 10, 2005, entitled "PERSONAL AND PORTABLE BOTTLE," and which is hereby incorporated herein by reference; and (v) U.S. Provisional Patent Application No. 60/732,925, filed Nov. 2, 2005, entitled "METHOD AND APPARATUS TO SENSE HYDRATION LEVEL OF A PERSON," and which is hereby incorporated herein by reference.

U.S. patent application Ser. No. 11/592,431 is also a continuation-in-part of U.S. patent application Ser. No. 11/451,781, filed Jun. 2, 2006, entitled "PERSONAL AND PORTABLE BOTTLE," which is hereby incorporated herein by reference, which claims priority to U.S. Provisional Patent Application No. 60/785,825, filed Mar. 26, 2006, entitled "MEDICAL MONITORING SYSTEM," and which is hereby incorporated herein by reference.

In addition, this application is related to: (i) U.S. patent application Ser. No. 11/451,780, filed Jun. 12, 2006, now U.S. Pat. No. 8,202,217, entitled "HEALTHCARE BASE," and which is hereby incorporated herein by reference; (ii) U.S. patent application Ser. No. 11/479,665, filed Jun. 30, 2006, now U.S. Pat. No. 8,118,740, entitled "MOISTURE SENSOR FOR SKIN," and which is hereby incorporated herein by reference; and (iii) U.S. patent application Ser. No. 11/491,774, filed Jul. 22, 2006, entitled "PORTABLE CONTAINER WITH SPEAKER ATTACHED," and which is hereby incorporated herein by reference.

BACKGROUND

In the United States alone, there are more than 30 million adult runners. To maintain proper body temperature, runners sweat. The water in the sweat needs to be replaced. Appropriate hydration is critical for runners, particularly those who are running for a long period of time. Improper hydration is one of the most common reasons why marathon runners require medical attention during races.

Dehydration causes numerous problems. Even being at one-percent dehydration can affect a runner's performance. For example, a one-percent dehydration may lead to a 10% decrease in performance, which can translate to about 1-hour delay over an extended race, such as a triathlon. In other words, a relatively small fluid loss, such as one pint, can decrease athletic performance by 10-15%. In addition to diminished performance, symptoms of dehydration include thirst, irritability, headache, weakness, dizziness, cramps, chills, vomiting, nausea, and head or neck heat sensations.

The severely dehydrated can go into shock and end up losing control of all of their bodily functions. Though terribly thirsty, they cannot drink. Even ice chips in their mouths might make them vomit. At that point, to replenish the lost fluids, they need to have fluids applied intravenously.

Dehydration is not the only problem. Over-hydration can be problematic as well. Runners lose not only water, but also a certain amount of sodium and other minerals while sweating. Runners can consume large quantities of water during their races. This can cause a drop in overall sodium levels and, potentially, hyponatremia, which means low levels of salt in the blood. The problem typically arises when the runner runs for a long duration of time, such as three hours, while drinking only plain water.

The human body plays a delicate balancing act with the concentration of sodium in the blood. Small changes in the balance can be dangerous to a body's osmotic chemistry. Almost every physiological process in our body depends on osmotic gradients, with water moving from an area of lower salt concentration to an area of higher salt concentration. Severe sodium imbalance may lead to seizures, increased intracranial pressure, pulmonary edema (fluid in the lungs), respiratory arrest and even death. Many scientists view hyponatremia being as threatening to runners as dehydration and heat sickness.

To prevent dehydration or over-hydration, one approach is to drink the amount of fluid substantially equal to the sweat and urine losses.

Sometimes thirst may be a good indicator as to when to drink. If you are thirsty, drink. Monitoring the volume and color of urine can be helpful in determining hydration status as well. A general guideline is to drink until your urine is clear. However, by the time you feel thirsty, for example during a workout, you may already be dehydrated. Also, in the heat of a race, a runner may forget or suppress the natural instinct of thirst and not check his urine.

Another approach to determine when to drink is to measure one's body temperature. One recent approach is to swallow a small temperature sensor. However, some athletes may not want to swallow such a foreign object.

One recommendation from a number of marathon associations is to weigh runners prior to a race and again following the race. The drop in weight post-exercise could provide an indication as to roughly how much fluid one needs to replenish. In the heat of a long race, it may not be convenient to weigh oneself during the race. Also, runners must exercise care when stopping to weigh themselves in the middle of a race. Postural hypotension is experienced when a runner suddenly stops. Blood pooling in the legs can lead to inadequate blood supply to other parts of the body. The runner can then feel faint and collapse.

Although running has been used above as an example to illustrate the importance of proper hydration, proper hydration is important in other types of sports, particularly for endurance sports or sports lasting for a long duration of time. The challenges not only fall on the adults, but children as well.

Hydration is also an issue in children. It can be quite difficult to determine whether a toddler is sufficiently hydrated. We cannot depend on whether he is crying or not. He can be distressed for numerous reasons, and the basic reason may not be easily decipherable. The difficulty is exacerbated if the toddler has diarrhea and is vomiting. Typically, particularly for first-time parents, they often take the toddler to a healthcare provider.

Another issue is related to the dryness of a person's skin. It is typically determined by the person's genetic makeup and the environment. Genetic conditions such as atopic dermatitis and icthyosis cause severe dry skin conditions. According to some studies, just in the United States alone, such genetic conditions affect more than 10 million people. When the skin flares up, it can be very annoying and itchy. One way to alleviate the dry skin conditions is to hydrate the skin, such as by applying lotion and the like. If not quickly treated, the symptoms can rapidly deteriorate.

Skin dryness can also be due to a person's profession. For example, health care professionals have to constantly wash hands. This causes skin dryness.

The aging process might also be linked to skin dryness. Dry skin is susceptible to more wrinkles, which may not be cosmetically appealing.

Sometimes, a person might not even be aware that his skin is dry, or that dry skin has its undesirable consequences.

Further, traditionally, a person schedules an appointment with a medical provider (e.g., a doctor), and then visits the medical provider at the scheduled time. During the appointment, the medical provider can perform a health or wellness check-up for the person. In some instances, the person might be due for a diabetes checkup, a hearing checkup, etc. In other instances, the person may be interested in particular medical conditions. For example, the person might have a skin discoloration that would like to have check to see if it is skin cancer. Unfortunately, for all these checkups and medical evaluations, the person must visit the medical provider's office, which is time consuming and inconvenient for the person. Moreover, medical providers typically charge patients per office visit, so the cost to the person or their insurance company is significant.

It should be apparent from the foregoing that there is a need for ways to determine if a person is appropriately hydrated. Furthermore, it is desirable that the ways be applicable to people of different ages and in different conditions. Also, it would be helpful if at least some of the ways are affordable so that people with limited means can still use them.

It should also be apparent from the foregoing that there is a need for improved approaches to assist people to be aware of skin dryness. And, there is a need to help them to reduce or to avoid skin dryness.

In addition, there continues to be a need for improved approaches for persons to have their health and wellness monitored.

SUMMARY

In different embodiments, the present invention provides methods and apparatus to measure the hydration level of a user based on measuring the saliva of the user. The measurements can be used to indicate if the user is appropriately hydrated. Different embodiments are applicable to people of different ages and in different conditions. Some embodiments are inexpensive and disposable. Other embodiments are applicable for more than one-time use. Yet other embodiments are applicable for continual use or re-use.

Different embodiments of the invention can be implemented in numerous ways including, a method, system, device, and a computer readable medium. Several embodiments of the invention are discussed below.

In one embodiment, a hydration sensor includes a hydration sensing element. The sensing element can be a disposable sensing element. The sensing element includes a piece of water-permeable material, such as a blotting paper, which can be a piece of filter paper. The blotting paper is sandwiched between two pieces of water-impermeable material. In one example, the water-impermeable materials can be adhesive tapes. To measure the hydration level of a user, the sandwiched blotting paper is placed in the user's mouth. Based on capillary action, saliva gets into the paper from the edges. In one embodiment, the rate at which the saliva flows into the paper is a function of the concentration of water in the saliva, or depends on the viscosity of the saliva. By measuring the extent to which the saliva gets into the paper, the hydration level of the user can be determined.

In one embodiment, the sandwiched blotting paper includes a chemical compound deposited on a first side of the blotting paper. The second side of the paper is exposed to saliva, which diffuses or wicks into the first side. The compound when exposed to saliva or water becomes a conspicuous colored patch. This color patch diffuses back to the second side of the blotting paper. The amount or the extent of the compound that changes color depends on how dehydrated the user is and the duration the paper is in the mouth. For example, if the duration of time is fixed, the amount of the compound that changes color provides an indication on the hydration level of the user.

In one embodiment, the hydration sensing element is a hydration sensor. In another embodiment, the hydration sensing element is incorporated into different apparatus to form a hydration sensor. For example, the element is incorporated to a bottle, which can carry fluid. In another embodiment, the element is incorporated to a carrier, such as a box, which can include a clip to attach the box to the clothing of the user. The box can have a timer. The user can turn on the timer after placing the element into his mouth. After a preset amount of time, the timer will alert the user that the measurement is over and the user can remove the element from his mouth to check for his hydration level. In yet another embodiment, the sensor is a handheld device, which can carry a number of sensing elements.

In one embodiment, a hydration sensor incorporates electrical components to automatically measure a hydration sensing element, such as measure visual indications on the element. For example, the hydration sensor includes photodiodes and photo-sensors to measure the element.

Instead of based on visual indications, in one embodiment, sensing is performed through other electrical means. There can be electrically conducting lines on a piece of water-permeable material, such as blotting paper. The sensor measures the time it takes saliva to diffuse from one electrical line to the next to indicate the hydration level of the user. Instead of on a piece of paper, the conducting lines may be attached to a piece of cloth or a piece of fiberglass cloth. In one embodiment, such sensors are applicable for more than one-time use.

In one embodiment, a hydration sensing element is re-usable, or more adaptable to be used numerous times. For example, the sensing element can include a hollow tube or chamber with a small diameter, with conducting wires inside the tube or chamber. The ends of the wires are staggered relative to the opening of the tube. A timer is used to measure the time it takes for saliva to go from one wire end to another wire end. Based on the time measured, the hydration level of the person can be identified. To re-start measurements, saliva in the tube is cleared. There can be different ways to clear the saliva from the tube. One approach is based on a mechanical air pump.

In another embodiment, a re-usable hydration sensor with a mechanical pump can be made in the shape to fit into the mouth of the user. The mechanical pump is activated by the user biting onto the sensor. The sensor includes a wireless transmitter to send measurements to, for example, a portable device. Based on the measurements received, the portable device can alert the user if he needs to drink.

Instead of a mechanical pump, in one embodiment, the saliva is cleared from the tube with an electro-mechanical pump.

The sensing elements can be made of other types of materials. In one embodiment, the sensing element is a piezoelectric element on an absorbent medium, such as a thin sponge, to measure the viscosity of fluid. The sensor can be used to provide an absolute index of the hydration level of a user.

Different people in different physical and/or environmental conditions may need differing amounts of fluid. In one embodiment, a hydration sensor is calibrated. The calibration can be for different types of people in different conditions. A user can perform the calibration. After the calibration, the sensor or that type of sensor can become personalized to the user. For example, before a person starts using a hydration sensor or a type of hydration sensor, the person first gets herself appropriately hydrated. Then, she measures the time it takes for the sensor to indicate that she is appropriately hydrated. The time measured would serve as the baseline. Future measurements can be relative to the baseline.

An embodiment of a sensor with a wireless transmitter has been described. In one embodiment, the sensor is connected to another device through the wireless transceiver. The connection allows the measured hydration levels to be transmitted to the other device, and allows the sensor to receive signals from the other device, such as recommendation on fluid consumption. The other device can be a portable device also carried by the user, a device not in the vicinity of the user, or a base station in the vicinity of the user. In another embodiment, the sensor is connected to another device through a cable.

Different embodiments regarding packaging the sensor have been described. In other embodiments, the sensor can be incorporated into a spoon or a cup. In another embodiment, a hydration sensor is integrated to a bottle or a container, which can carry fluid or beverages for the user to drink. Some of the electronics in the sensor can be transferred to the bottle or the container. There can be promotional materials or different designs on one or more surfaces of the bottle or the container.

In one embodiment, one or more additional sensors are integrated or coupled to a hydration sensor. The one or more additional sensors are for sensing, for example, a piece of environmental information in the immediate vicinity of the hydration sensor. The additional sensor can be a temperature sensor or a humidity sensor. In another embodiment, an additional sensor can measure another piece of information regarding the person using the hydration sensor, such as the person's body temperature or activity level. The additional sensor information can help determine the appropriate amount of fluid for the user to consume. In another embodiment, the additional sensor information can modify the baseline calibration level of the sensor.

In one embodiment, a hydration sensor also provides recommendation to a person using it. The recommendation can be alerting the person to be aware of other factors that can affect the measurements. For example, an audio signal can tell the person to avoid eating food such as candy immediately before measurements.

A number of embodiments of the present invention pertain to a moisture sensor for skin. For example, by use of the moisture sensor, a user can determine that her skin is too dry, and can conveniently apply lotion from a bottle of lotion. The lotion can soothe the skin and reduce problems due to skin dryness, which may result from eczema, cold weather, or constantly washing one's hands. Application of lotion can also help reduce wrinkles by keeping the skin moist. In addition, in one embodiment, the sensor can assist in identifying different types of lotion to apply.

In one embodiment, the moisture sensor can be in the shape of a nail file or a mascara container. In another embodiment, the sensor can be incorporated into other apparatus, such as a pen, a phone or a container (e.g., a lipstick container). The electronics for the sensor could be on one printed circuit board. The circuit board can be flexible so as to more easily conform to the profile of the skin surface to be measured.

In one embodiment, the moisture sensor measures the dryness of a person's scalp, or the skin on the person's head. The sensing surface could be in the configuration of multiple fingers. The fingers could increase the surface area of the sensing surface, while enhancing the ease by which one can measure the scalp underneath a layer of hair. In another embodiment, the sensing surface could be in the configuration of a comb. For example, by using the moisture sensor, a user can determine that he should use a particular type of shampoo or conditioner (e.g., shampoo for dry scalps).

The moisture sensor can be integrated to a bottle of lotion, such as on the bottle's shoulder or cap, or on a face of the bottle. Alternatively, instead of being integrated with the bottle, the sensor can be attachable to the bottle. The sensor can be in a structure that is in the shape of a cylinder, with a corresponding slot on the bottle for the cylinder to be inserted.

In a number of embodiments, a moisture sensor can communicate with one or more electrical components integral with a bottle through wired or wireless connections. The electrical components can provide recommendation to the user based on measured results from the sensor, such as through a display or a speaker on the bottle. In addition, there can be an electrical connector at the bottle for uploading the measured results to another device. For example, the other device can be a memory device or a computer. In another embodiment, the electrical components integral with the bottle are in a base with a slot that allows the bottle to fit snugly therein.

There can be one or more other sensors to measure other attributes of the user and/or the environment. For example, one additional sensor is a humidity sensor to sense the condition of the environment. Such information could further assist a user in determining the type of lotion to apply to her skin.

Different embodiments of the invention also pertain to a medical monitoring system. The medical monitoring system facilitates end-users in obtaining medical information concerning their health or wellness. In one embodiment, an end-user is provided with a medical monitoring appliance. In another embodiment, an end-user acquires an appropriate medical monitoring appliance. The end-user can utilize the medical monitoring appliance to capture health data concerning the end-user. The health data can be electronically stored at a central repository and be available for electronic access by medical personnel and/or the end-user. Different embodiments of the invention also facilitate remote evaluation of an end-user's health data by another person, such as a medical specialist.

Different embodiments of the invention can be implemented in numerous ways, including as a system, device, apparatus, and method. Several embodiments of the invention are discussed below.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which:

FIGS. 22F, 22G and 22H are rear, side and front view for a moisture sensor according to still another embodiment of the invention.

DETAILED DESCRIPTION

In one embodiment, a hydration sensing element measures the hydration level of a user based on measuring the saliva of the user. The sensing element can be configured to measure the viscosity of the saliva of the user. Typically, when the user is well hydrated, his saliva has a higher concentration of water or is less viscous than when he is dehydrated. If the saliva is less viscous, it would wick or move faster or deeper by capillary action into the sensing element. FIGS. 1A-1D illustrate different embodiments of a hydration sensing element more applicable for one-time use.

Figure 1A:
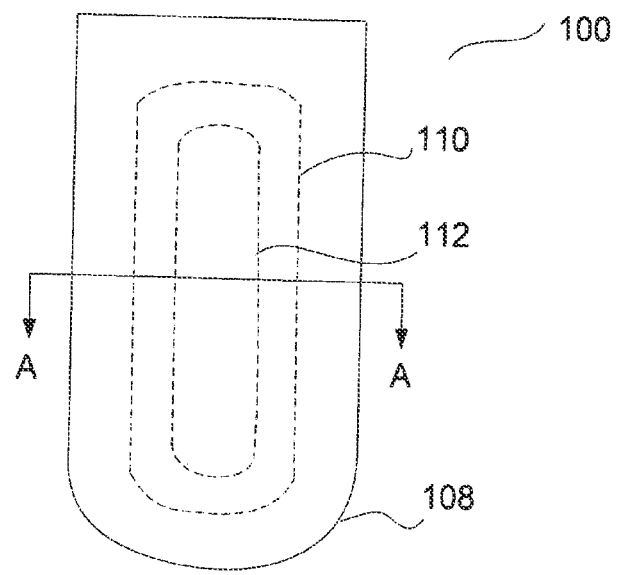
FIGS. 1A-1D illustrate different embodiments of disposable hydration sensing elements according to the invention.
Figure 1B:
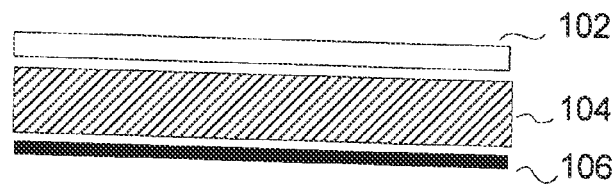

FIG. 1A shows the top view and FIG. 1B shows a cross-sectional view at AA of one embodiment of a hydration sensing element 100. The element 100 can be a disposable hydration sensor, designed to be used once and then disposed. The element 100 includes a piece of water-permeable material 104, such as blotting paper, sandwiched between two pieces of material, 102 and 106, that are impermeable or substantially impermeable to water. In one embodiment, the water-impermeable material can be adhesive tape. To measure the hydration level of a user, at least a portion of the element 100 is placed in the user's mouth. From at least one of its edges, such as 108, and based on capillary action, saliva diffuses or wicks into the water-permeable material 104. The dryness of the user's mouth, or the characteristics of the user's saliva, determines the amount of saliva getting into, or how far or deep the saliva seeps into, the water-permeable material 104. For example, there can be a number of rings on the paper, such as 110. The user can be considered as well hydrated if within one minute, saliva reaches the inner ring 112 on the paper 104.

In one embodiment, the water-permeable material 104 can be a piece of white filter paper, such as similar to the paper used for coffee filters. In one example, the water-permeable material 104 can be about 4 mils thick. In another example, the water-permeable material 104 can be sandwiched between a piece of translucent (or transparent) tape 102 and a black tape 106. The area where the water-permeable material 104 is wet becomes translucent, allowing the black tape 106 to be seen through the tape 102. As an example, for a normal person, after one minute in his mouth, saliva might extend into the water-permeable material 104 a distance of about 2 millimeters when he is appropriately hydrated. But if the person is dehydrated, saliva might extend in by less than 0.5 millimeter, again after the sensing element is in his mouth for 1 minute.

Instead of seeping in from the edge, in another embodiment, saliva can seep into a sensing element through an opening or hole not at the edge. To illustrate, again the water-permeable material 104 can be sandwiched between two pieces of tape. The edges of the sandwiched water-permeable material 104 are sealed to prevent saliva from getting in. However, there is a hole or an opening in the middle of one of the tapes. The time it takes for the saliva to extend outward from the middle of the opening can be used to determine the dryness of the mouth.

Figure 1C:
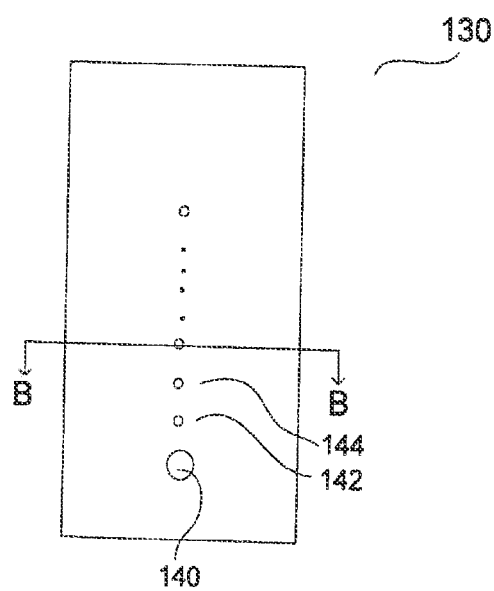
Figure 1D:
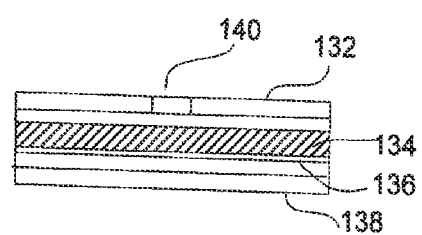

FIG. 1C shows a top view and FIG. 1D shows a cross-sectional view at BB of another embodiment of a hydration sensing element 130. The hydration sensing element 130 includes a water-permeable material 134 sandwiched between two water-impermeable materials 132 and 138. The element 130 can be a disposable hydration sensing element.

In one embodiment, the water-permeable material 134 can be a piece of blotting paper, which again can be a white filter paper. The water-permeable material 134 includes a chemical compound 136 on or coupled to one side, the first side, of the water-permeable material 134. For example, the chemical compound 136 is deposited on the first side (or a portion of the first side). The two water-impermeable materials again can, for example, be tape. A piece of tape (the first-side tape) 138 covers the compound 136. The second side of the water-permeable material 134 is also covered by tape (the second-side tape) 132. In one embodiment, both tapes are not transparent, and can be opaque. The edges of the tapes 132 and 138 are sealed to each other. The second-side tape 132 has an opening 140 that exposes the water-permeable material 134 to saliva. The second-side tape 132 is mostly opaque except having a number of transparent holes 142 and 144 (or spots or circles) at varying distances from the opening. The transparent holes 142 and 144 provide windows to visually see the water-permeable material 134 from the outside. In one embodiment, such as shown in FIG. 1C, the transparent holes 142 and 144 can be arranged in a line from the opening 140.

In one embodiment, when liquid, such as saliva, touches the water-permeable material 134, the saliva diffuses or wicks through it to the chemical compound 136 underneath. The part of the chemical compound 136 that gets wet becomes a conspicuous and/or visible color patch, and the visible patch diffuses or wicks through to the second side of the water-permeable material 134. For example, a colored (e.g., green) patch can appear on the second side. In one implementation, the chemical compound 136 is a water-based paint that is non-toxic and hypoallergenic. When saliva is mixed with the paint, the paint diffuses from the first side to the second side of the water-permeable material 134. In another example, the chemical compound 136 is a dye, such as a powdered food dye. Again when saliva reaches the dye, the dye diffuses from the first side and shows up on the second side of the paper.

When the sensing element 130 is in the mouth of the user, saliva gets into the opening 140, goes through the water-permeable material 134 (e.g., white filter paper) and reaches the chemical compound 136. The chemical compound 136 that is exposed to saliva generates a patch of color, such as a green color on the white filter paper. The green color extends back to the second side of the water-permeable material 134, or the side with the opening. The number of spots changing color from, such as, white (the color of the paper) to green (the color of the patch) depends on the duration the element 130 is within the mouth and the hydration level of the user. In one embodiment, if one fixes the time the element 130 is to stay in the user's mouth, based on the number of spots that have changed color, the hydration level of the user can be inferred. In another embodiment, the transparent spots are in the shape of alphanumeric symbols, such as numbers. For example, a transparent number closest to the opening 140 can be a numeral one, the second most closest transparent number can be a numeral two and so on. In other words, for numbers, the numbers can be in a sequence, such as in ascending order, or in descending order.

As described above, in one embodiment, a hydration sensing element includes a piece of water-permeable material with a first side and a second side, a chemical compound coupled to the first side of the water-permeable material, and a first piece and a second piece of water-impermeable material. The chemical compound is located between the first piece of water-impermeable material and the first side of the water-permeable material, while the second piece of water-impermeable material is coupled to the second side of the piece of water-permeable material. In other words, the water-permeable material is located between the two pieces of water-impermeable material. When the hydration sensing element is placed in the mouth of the user, saliva is allowed to reach the water-permeable material and the chemical compound. When saliva is in contact with the chemical compound, the part of the chemical compound that gets wet becomes a visible color patch. At least a portion of one piece of the water-impermeable material is transparent to show at least a portion of the visible color patch. The hydration level of the person is measured depending on the extent of the color patch.

There are different embodiments related to the chemical compound, the water-permeable material and the two pieces of water-impermeable material. These embodiments can be mixed and matched.

One embodiment relates to how saliva reaches the water-permeable material and the compound. In one configuration, at least one edge of the water-permeable material is exposed to allow the saliva to reach the water-permeable material and the compound. In another configuration, there is an opening on either the first or the second piece of water-impermeable material to allow saliva to reach the water-permeable material and the compound.

One embodiment relates to the transparency or the lack of transparency of the two pieces of water-impermeable material. Note that the two pieces can be made of different types of material. In one configuration, one piece of water-impermeable material is transparent. In another configuration, one piece of water-impermeable material is transparent, and the other piece of water-impermeable material is either opaque or translucent. In yet another configuration, the at least a portion of one piece of water-impermeable material that is transparent is in the shape of an alphanumeric symbol.

One embodiment relates to the physical structure or the shape of the chemical compound. In one configuration, the chemical compound is in the shape of a layer or a sheet. The sheet is coupled to the first side of the water-permeable material. In another configuration, the compound is in the form of particles. A number of such particles are at different positions on the first side of the water-permeable material. For example, the compound is a powdered or granular dye. The compound can be food dye, and can be in tiny concentrated grains. With sufficient water, liquid or saliva, the powdered or granular dye can create a conspicuous color patch across at least a portion, which can be a significant portion, of the water-permeable material. In one embodiment the grains deposited at different locations are not of the same color, such as two different colors at two different locations on the water-permeable material.

One embodiment relates to where a color patch is seen. In one configuration, the water-impermeable material with at least a portion being transparent is the second piece of water-impermeable material. At least a portion of a color patch permeates from the first side to the second side of the water-permeable material to be seen through the second piece of water-impermeable material. In another configuration, the water-impermeable material with at least a portion being transparent is the first piece of water-impermeable material.

In one embodiment, a hydration sensing element is a hydration sensor. In another embodiment, a hydration sensing element is incorporated into different apparatus to form a hydration sensor. For example, a hydration sensing element, such as one shown in FIGS. 1C-1D, can be attached to the end of a small rod or a handle. The hydration sensing element with the handle can become a hydration sensor.

Figure 2:
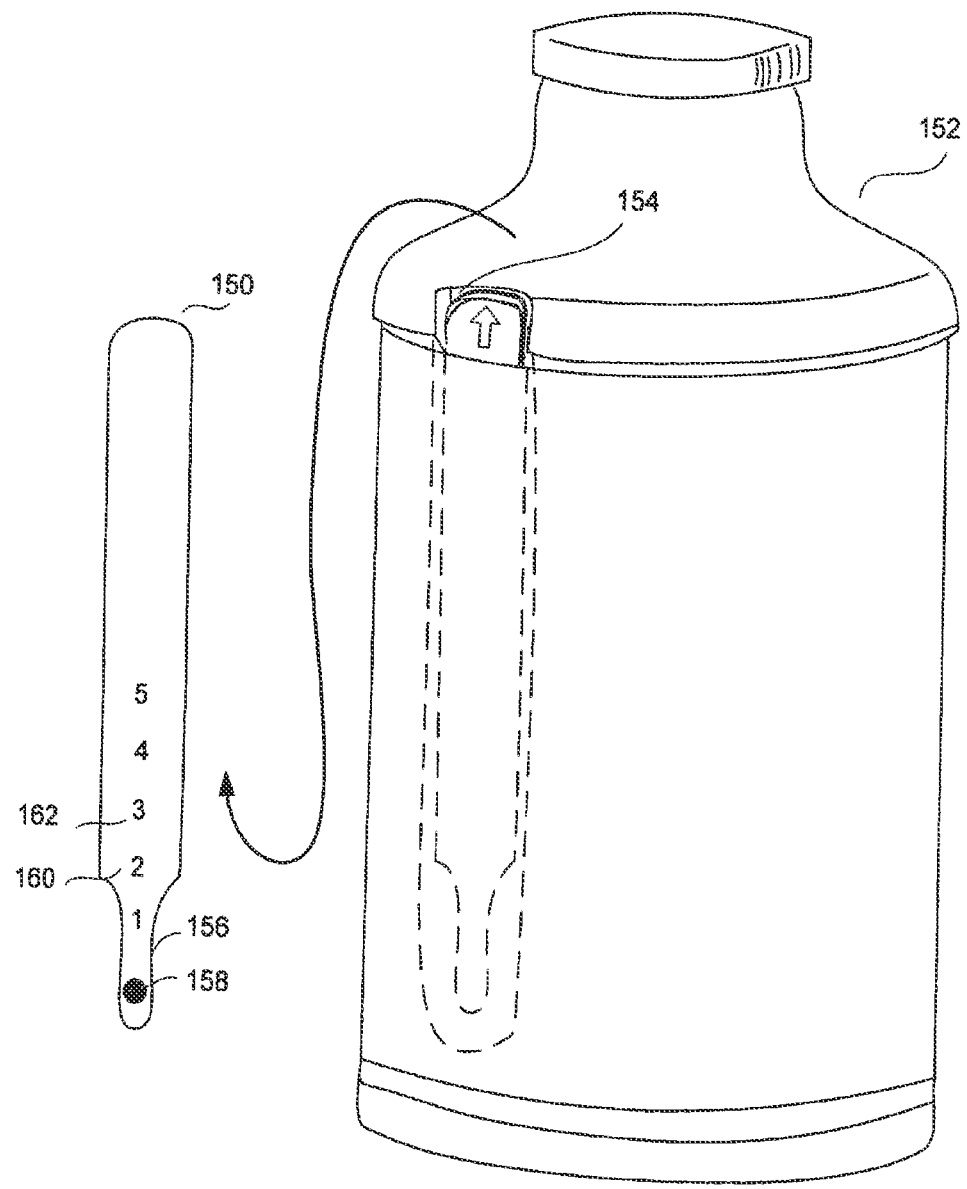
FIG. 2 illustrates an embodiment of disposable hydration sensing elements coupled to a bottle according to the invention.

FIG. 2 illustrates one embodiment of disposable hydration sensing elements 150 coupled to a bottle 152 which can carry a type of fluid or beverage. For example, the fluid can be a type of filtered water, electrolyte drinks or sports drinks, such as Gatorade®. The sensing elements 150 can be similar to the element shown in FIGS. 1C-1D. There can be a slot 154 on one side of the bottle 152 to carry the sensing elements 150. Each sensing element 150 can have a narrower section 156, which is the section to be put in the mouth of the user. An opening 158 can be provided close to the end of the narrower section 156 to receive saliva. Windows, 160 and 162, to the water-permeable material (e.g., filter paper) can be numbers, instead of just holes. Based on the measurement, one or more of such numbers can change color. For example, if only the numeral "1" changes color, the user is rather dehydrated so she should drink some fluid.

Figure 3B:
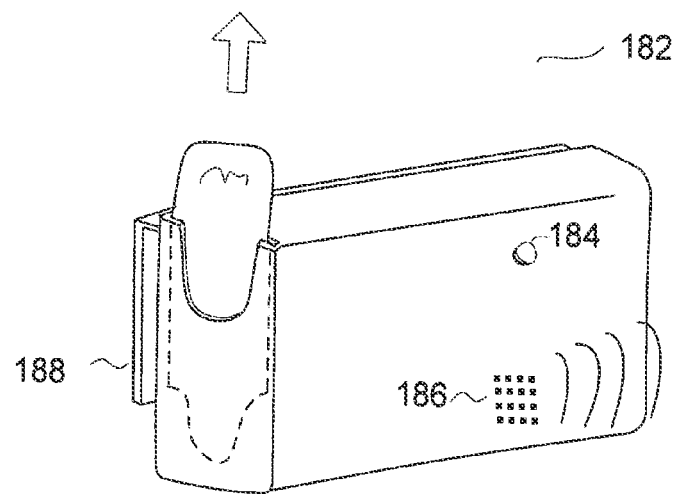
FIGS. 3A-3B illustrate an embodiment of a disposable hydration sensing element and its carrier that has a timer according to the invention.
Figure 3A:
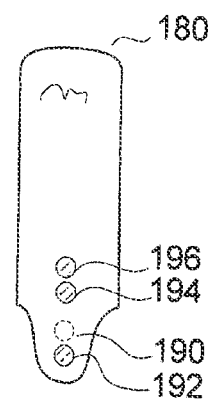

In another embodiment, sensing elements are stored in or carried by a carrier. The sensing elements with the carrier can be a hydration sensor. FIG. 3A illustrates an embodiment of a disposable hydration sensing element 180. FIG. 3B illustrates an embodiment of a carrier 182 that has, among other components, a timer, a switch 184 (such as an activation switch), an audio device 186 and a power source, such as a battery or a solar cell.

The carrier 182 shown in FIG. 3B can hold a number of the hydration sensing elements 180. In this example, the carrier 182 can be a handheld or wearable electronic device. In one embodiment, the carrier 182 can be in the shape of a box. The carrier 182 can have a mechanical device 188, such as a clip, to clamp or attach the carrier 182 onto the clothing of a user. In another embodiment, the carrier 182 can be configured into a wrist band and is carried on the wrist of the user, just like a watch. In yet another embodiment, the carrier 182 also functions as a watch and can include a display. In still another embodiment, the carrier 182 can be incorporated in or attached to a piece of clothing (e.g., helmet, hat, vest, belt or shirt) of the user, or incorporate in or attach to a portable electronic device carried or worn by the user.

The sensing element 180 shown in FIG. 3A can be similar to the elements shown in FIG. 2 or the element shown in FIGS. 1C-1D. For example, the element 180 can have a piece of water-permeable material (e.g., blotting paper) laminated between two pieces of tape. In this embodiment, the compound that produces color patches is on the same surface of the water-permeable material as the surface that is exposed to the opening. In this embodiment, there are a number of dots of a compound, and they can be of different color and at different distances from the opening 190. When they are not wet, the compound is a very small amount of dry powder and is inconspicuous. These can be grains of powder food dye. The grains can be of different color, such as red, blue and green. When there is liquid, the dye dissolves and a color patch is formed. In FIG. 3A, there are three dots. The dot nearest 192 to the opening 190 can be red in color; the second closest 194 can be blue and the furthest away 196 can be green.

To measure hydration level, the user pulls one of the sensing elements 180 out from the carrier 182, places at least a portion of the element 180 in his mouth and then pushes the button or switch 184 on the carrier 182. This will activate the timer. After a duration of time, such as 1 minute, the timer will activate the audio device 186, such as a beeper, which would beep. This will alert the user to remove the element 180 from his mouth and read it. If only the red dot 192 shows up, the user is very dehydrated. If a red 192 and a blue 194 dots show up, then the user is mildly dehydrated. If all three dots can be seen, the user is well hydrated.

Figure 4:
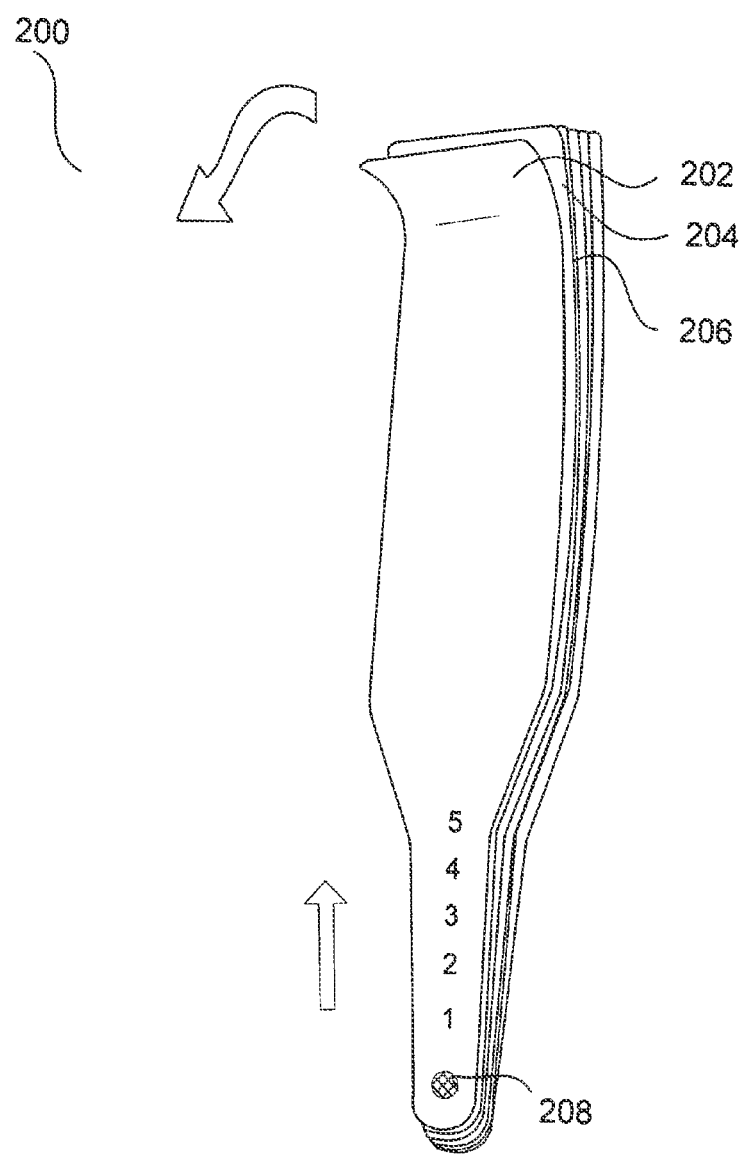
FIG. 4 shows one embodiment of multiple hydration sensing elements in a stack according to the invention.

FIG. 4 shows one embodiment 200 of multiple hydration sensing elements 202 and 204 linked, attached or stuck together into a stack. Each element, such as 202 and 204, can be similar to the element 150 shown in FIG. 2. In one embodiment, the elements 202 and 204 are glued or connected together, such as at their edges, 206. For example, this connection at the edges could provide a waterproof seal. To use each element, the user can peel one off and put it in his mouth. Alternatively, in one embodiment, the user can put the entire stack into his mouth. Saliva only goes into the top element because the only opening exposed is the opening 208 of the top element 202. After the measurement, the user can peel off the top element 202, and the opening in the next element, the element 204 beneath the top element 202, is exposed to be used.

Figure 5B:
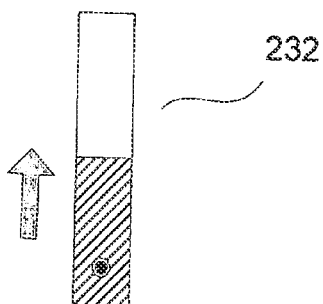
FIGS. 5A-5B illustrate an embodiment of a handheld hydration sensor that can automatically measure a disposable sensing element according to the invention.
Figure 5A:
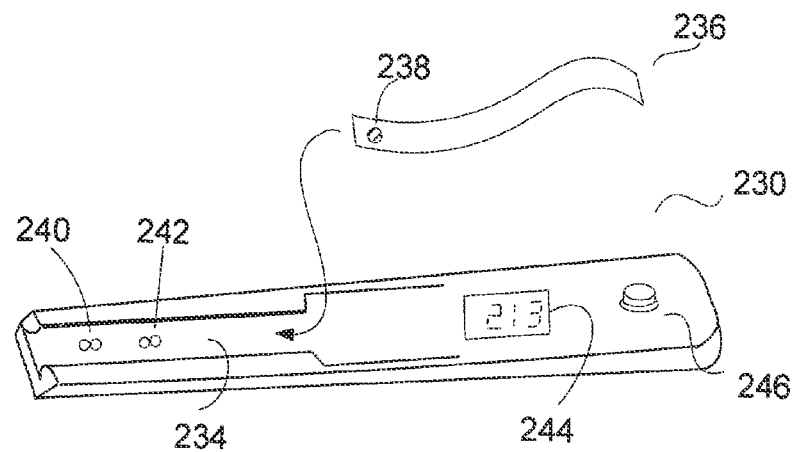

FIG. 5A illustrates an embodiment of a handheld hydration sensor 230 that can measure a sensing element. In one embodiment, the handheld hydration sensor 230 can measure a sensing element 232 such as shown in FIG. 5B.

The sensing element 232 shown in FIG. 5B can be similar to the one shown in FIG. 4, except that the water-impermeable material with the opening for saliva to get to the water-permeable material can be transparent. To take a measurement, the user places one such sensing element 236 into a slot 234 on top of the handheld hydration sensor 230. Next, the user places at least a portion (such as the narrower end) of the sensor 230 into his mouth, under his tongue, like a thermometer. The saliva in the user's mouth will permeate or wick from the opening 238 up the length of the sensing element 236, causing a color change to move up the sensing element as shown, for example, by the arrow in FIG. 5B. As shown in FIG. 5A, in the slot 234 of the handheld hydration sensor 230 there are two LED/photodiode pairs, 240 and 242, that sense the color change of the element.

Though there can be many pairs of photodiodes and photo-detectors along the slot 234, only two are shown. Each photodiode and photo-detector pair measures color change at different distance away from the opening, with the diode emitting light and the corresponding detector measuring the reflected radiation. In one embodiment, based on measuring changes in the reflected light from the different detectors, the extent that the saliva has diffused into the sensing element can be identified.

The handheld hydration sensor 230 in FIG. 5A can also include a timer 244 and a switch, such as an activation switch, 246, which can be functionally similar to the timer and switch shown in FIG. 3B. In one embodiment, the handheld hydration sensor 230 can include at least two pairs of LED/photo-detector positioned at different position in the slot 234, such as described above. The timer can track the time it takes saliva to wick up the element from the position of the first pair to the second pair. With the distance between the two pairs known, the handheld hydration sensor 230 can measure the rate the compound changes color, or the speed the color moves up the element.

A number of embodiments of hydration sensing elements have been described. They are typically based on visual measurements. They are typically more applicable for single use and can be disposable.

Figure 6A:
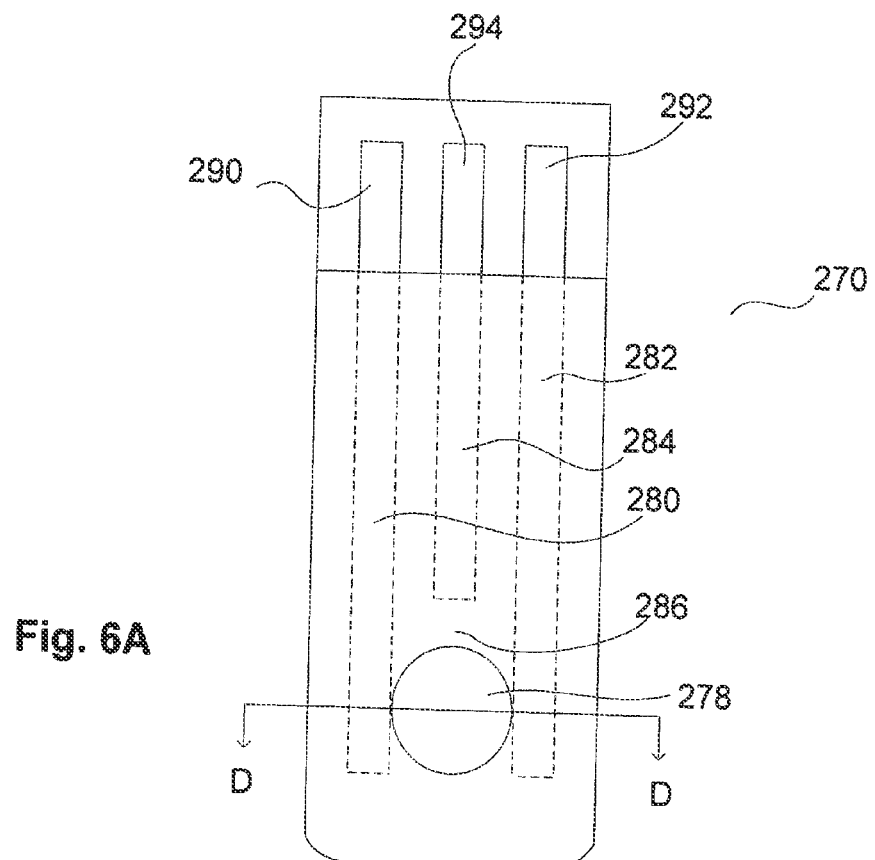
FIGS. 6A-6B illustrate a hydration sensing element applicable for more than one-time use according to an embodiment of the invention.
Figure 6B:
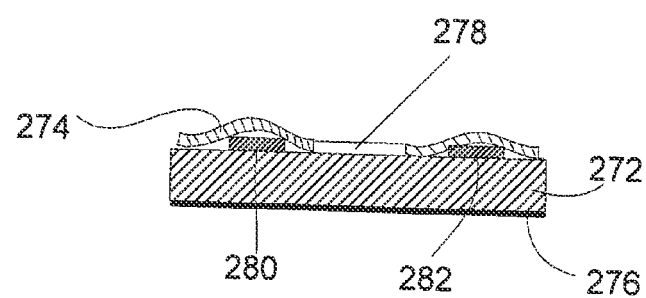

In one embodiment, a hydration sensing element uses electrical resistive measurements. The sensing element can be applicable for more than one-time use. FIGS. 6A-6B illustrate an embodiment of such a hydration sensing element 270. FIG. 6A shows the top view of the hydration sensing element 270, and FIG. 6B a cross-sectional view at DD. In one such embodiment, the sensing element 270 includes a piece of water-permeable material 272, such as a piece of blotter paper, sandwiched between two pieces of water-impermeable material 274 and 276. The two pieces of water-impermeable material 274 and 276 do not have to be transparent, and they can be tape 274 and 276. The top piece of tape 274 includes an opening 278, exposing a small part of the piece of the water-permeable material 272. There are a number of electrically conducting lines on the water-permeable material 272. In one embodiment, there are two conducting lines, such as the two outer lines, 280 and 282, shown in FIG. 6A. They are covered or encapsulated by the top piece of water-impermeable material 274. Each of the lines 280 and 282 has its corresponding metal contacts, such as the left conducting line 280 has a left contact 290 and the right conducting line 282 has a right contact 292.

A user can place the sensing element 270 shown in FIG. 6A in his mouth. Saliva then goes through the opening 278 and is absorbed by the water-permeable material 272. With saliva in the opening 278, the resistance between the lines, such as lines 280 and 282, is reduced. By measuring the resistance between the lines, one can determine how wet/dry the mouth is.

The embodiment of the hydration sensing element 270 shown in FIGS. 6A-6B can be coupled to a timer, which can be in a hydration sensor. The timer can be used to measure the resistance change between the conductors as a function of time after a sensing element is placed in the mouth. For example, before the user puts the sensing element in his mouth, the user activates the timer. At that point, the water-permeable material is dry, and the resistance between the lines can be in the range of more than 10 mega-ohms. The timer starts counting after it is activated (i.e., turned on). In one embodiment, the timer can stop counting when the resistance between the lines drops below a preset threshold, for example, 1 mega-ohm. The timer records the time elapsed. In one embodiment, the timer can produce a beeping sound or a flashing LED to indicate to the user that the resistance has dropped to the preset threshold, and the hydration measurement has been completed. The user can then take the sensing element out of his mouth, and the hydration level of the user can depend on the elapsed time. In another embodiment, the elapsed time can be preset to measure the resistance between the lines. The hydration level can depend on the resistance value.

In yet another embodiment, referring to FIG. 6A, the hydration sensing element 270 includes a mechanism to initiate measuring the hydration level of the user. In this embodiment, there is a third conducting line 284 between the two outer lines 280 and 282. This third line 284 can have its own contact 294. In one embodiment, at least a portion of each of the outer electrically-conducting lines 280 and 282 is closer to the opening 278 than the third conducting line 284. For example, a small portion of the edges of the outer two conducting lines 280 and 282 are exposed to the opening, and the third conducting line 284 is recessed at a certain distance 286 from the opening 278. When the user puts the sensing element 270 into his mouth, the saliva can reduce the resistance between the outer two conducting lines 280 and 282 almost immediately. For example, a timer can start counting when the resistance between the outside lines 280 and 282 drops below a preset value. In other words, when the resistance between the two outer conducting lines is below a preset value, the sensing element 270 starts sensing the hydration level of the user. Then, as saliva continues to diffuse into the water-permeable material 272, the resistance between the middle contact 294 and the contacts of either or both of the outer conducting lines 290 and 292 drops. Again, in one embodiment, when this resistance drops, which can be to below a certain preset value, the timer stops counting.

As discussed, the water-permeable material 272 shown in FIG. 6A can be based on a piece of paper, such as blotting paper. In another embodiment, the water-permeable material 272 is a piece of cloth, such as polyester cloth. The conducting wires can be glued, sewn or integrated into the water-permeable material, such as cloth, or they can be printed with electrically conductive ink onto the material.

In another embodiment, instead of sandwiched between water-impermeable materials, like tape, the water-permeable material can be encapsulated, pressed or heat-sealed in between two pieces of harder and/or more durable materials, such as plastic strips or printed circuit boards. The strips or boards have their corresponding openings for saliva to get in. In one embodiment, the conducting wires can be on one of the strips or boards, which are coupled to or pressed against the water-permeable material, such as cloth or paper.

The hydration sensing element 270 shown in FIG. 6A can be applicable for more than one-time use. One approach is to let the sensing element 270 dry after it has been in the mouth of the user. When it is dry, the user can use the sensing element 270 again for measurement. Alternatively, the user can dip the sensing element 270 in rubbing alcohol, which would speed up the drying process and disinfect the sensing element 270. If the water-permeable material is a piece of cloth, in one embodiment, the user can more easily wash and dry it after it is used.

In one embodiment, a small amount of salt (or other types of resistance-lowering materials) is added in the water-permeable material shown in FIG. 6A, such as in between or among the lines. The resistance-lowering materials can be used to reduce the resistance measured when there is fluid, such as saliva, in between the lines.

Figure 7A:
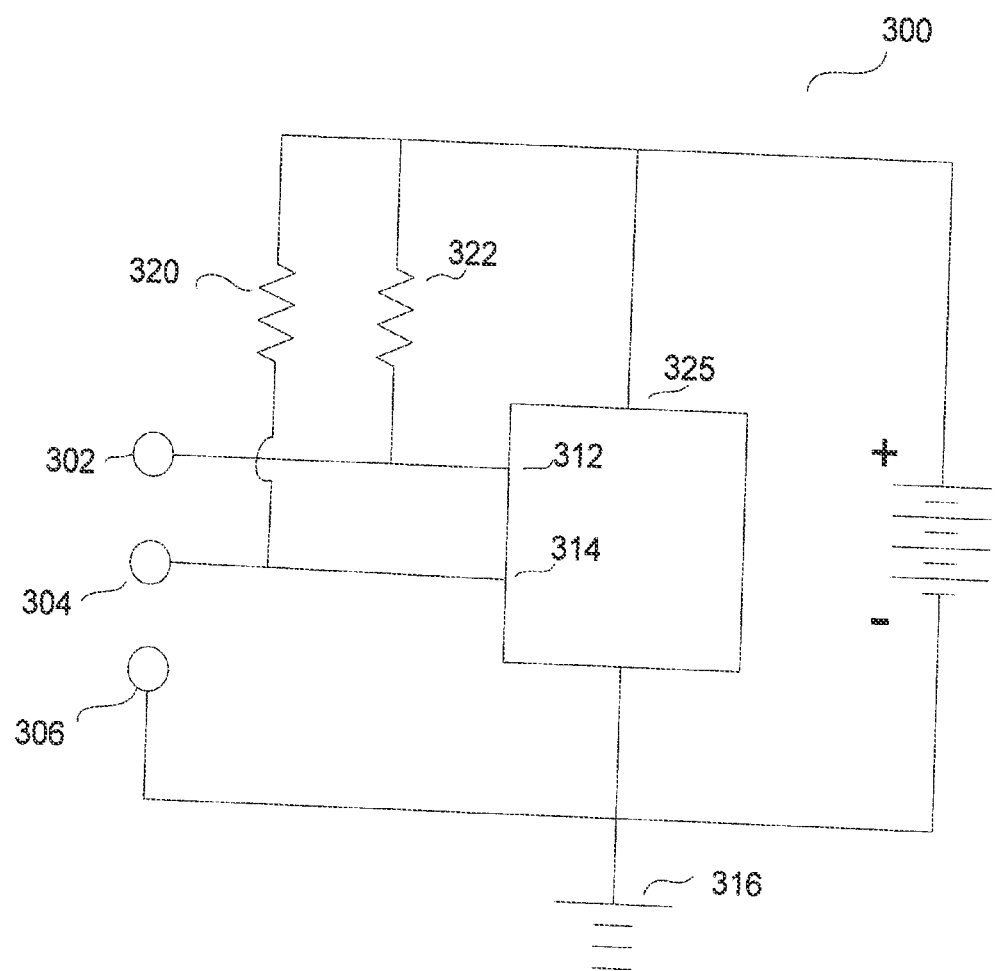
FIGS. 7A-7B show different embodiments of electrical components to measure the outputs from the sensing element shown, for example, in FIGS. 6A-B, according to the invention.

FIG. 7A shows an embodiment 300 of electrical components to measure the outputs from a sensing element, such as the sensing element 270 shown, for example, in FIGS. 6A-6B. In FIG. 7A, the three contacts, 290, 294 and 292 from the sensing element 270 shown in FIG. 6A are connected to a first input terminal 302 and a second input terminal 304 of a microcontroller unit 325 and to a ground input terminal 306, respectively. Two inputs 312 and 314 of the microcontroller unit 325 are connected to the first terminal input 302 and the second terminal input 304, respectively. In addition, the two inputs 312 and 314 are also connected to the Vcc of the microcontroller unit 325 through two resistors 320 and 322. The two resistors 320 and 322 can, for example, be 10 mega-ohm resistors. A battery is connected between Vcc and ground 316. The microcontroller unit 325 can include a counter and is programmed so that when an input signal that is lower than a first threshold value is registered between the first input terminal 302 and ground 316, the counter starts counting. This occurs when the resistance between the outer contacts 290 and 292 of the sensing element 270 drops lower than the first threshold value. The time interval between counts can be fixed. The counter stops counting when an input signal that is lower than a second threshold value is registered between the second input terminal 304 and ground 316. The number of counts is registered. As an example, assume the battery is 1.5 volts, the first threshold value is 0.75 volts and the second threshold value is also 0.75 volts. The microcontroller unit 325 can also be programmed to convert the count to a dryness level, and display the dryness level on a display. To convert the count to a dryness level, there can be a conversion table stored in the unit 325. For example, one approach can be that a count number within a certain range implies that the user is well hydrated. Such a conversion table can be determined based on calibrating the sensing element, which is further discussed below.

Figure 7B:
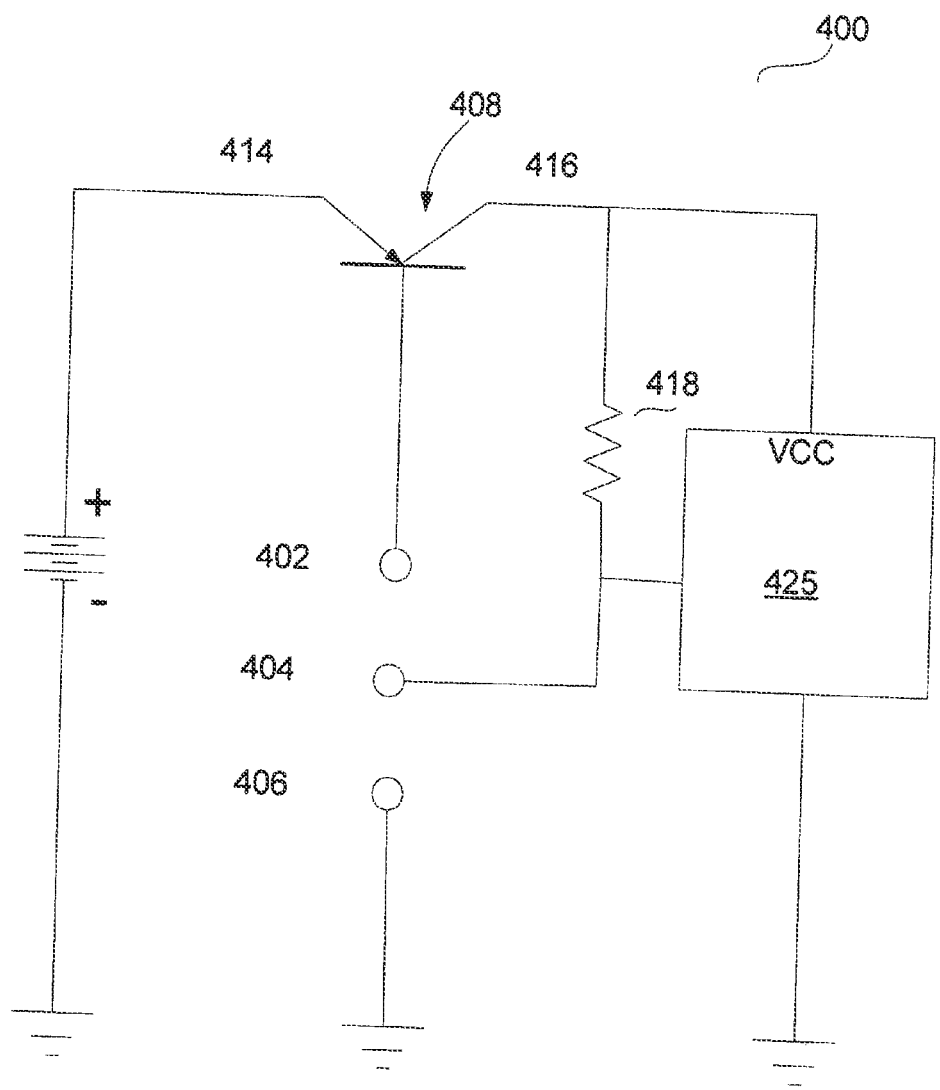

FIG. 7B shows another embodiment 400 of sensor electronics applicable for a hydration sensing element, such as the sensing element 270 shown, for example, in FIGS. 6A-6B. In this embodiment, the three contacts 290, 294 and 292 from the sensing element 270 shown in FIG. 6A are connected to the base 402 of a PNP transistor 408, an input pin 404 of a microcontroller 425, and ground 406 respectively. A battery is connected to the emitter 414 of the transistor 408 and to ground 406. A resistor 418 is connected between the input pin 404 of the controller 425 and to the collector 416 of the transistor 408, which is connected to the positive power-supply (VCC) input of the microcontroller unit 425. To illustrate, in one embodiment, the battery is 1.5 volts, and the resistor 418 is 10 mega-ohms. When the voltage between the outer contacts shown in FIG. 6A (or the voltage at the base of the transistor) reaches, for example, 0.7 volts, the transistor 408 starts to conduct, connecting the positive terminal of the battery to the VCC input of the microcontroller unit 425. This would turn on the microcontroller unit 425, and the microcontroller unit 425 would be programmed to start counting. The middle contact 294 of the sensing element 270 is connected to the collector 416 of the transistor 408 through the resistor 418. When the input at the input pin 404 of the microcontroller unit 425 reaches, for example, 0.75 volts, the unit 425 is programmed to stop counting. Again, the number of counts can be converted by the microcontroller unit 425 to a hydration level, and can be displayed.

Figure 8A:
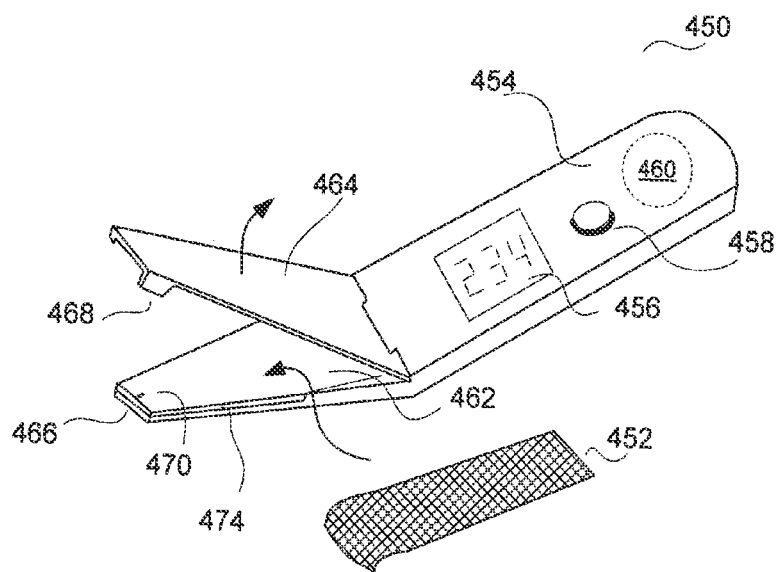
FIGS. 8A-8B show a hydration sensor applicable for more than one-time use according to an embodiment of the invention.
Figure 8B:
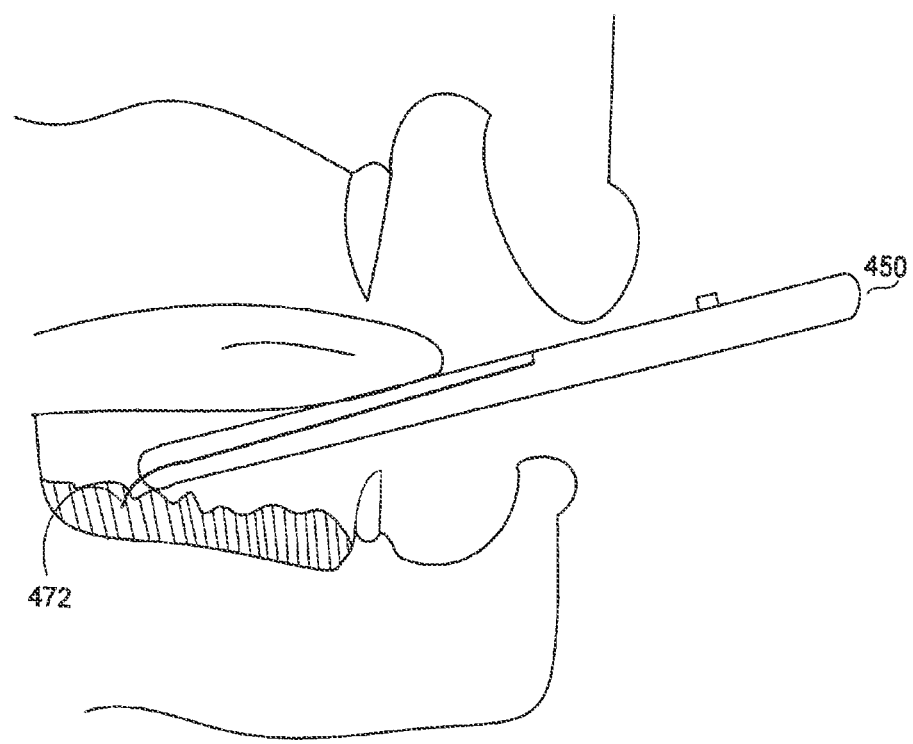

FIGS. 8A-8B show an embodiment of a hydration sensor 450 that is applicable for more than one-time use. FIG. 8A shows a hydration sensor housing 454 for the sensor 450.

The sensor housing 454 includes a timer 456 (which can also function as a clock), a switch 458, such as an on/off switch, and a power source 460, such as a battery, among other electronics. The front portion of the housing 454 includes a cavity 462, which can be closed by a hinged door 464. In one embodiment, the door 464 can be locked by a clip 468 at the tip of the door 464. When the door 464 is closed, the door 464 encloses the cavity 462, except that at least one end 466 (a first end) of the cavity is not fully closed.

The cavity 462 can hold a sensing element, which, in one embodiment, is a piece of water permeable material 452. The water-permeable material 452 can, for example, be a blotting paper, or a piece of cloth, such as fiberglass cloth or polyester cloth.

In one embodiment, inside the cavity 462 there are a number of electrical contacts 470, such as three contacts, and they are positioned proximate to the first end 466 of the sensor housing 454. In one embodiment, the contacts 470 can be on the surface of a printed circuit board in the cavity 462.

The hydration sensor 450 shown in FIG. 8A can be used to measure the user's hydration level. Assume that there are a number of electrical contacts 470, such as three contacts. The contacts 470 are spaced apart, with the resistance value between the first two contacts from the first end 466 of the sensor housing 454 for starting the timer 456, and with the resistance value between the second and the third contacts for stopping the timer 456. The spacing between any two contacts can be, for example, 0.010 inches. The three contacts can be the three contacts for the circuits shown in FIG. 7A, with the first contact from the first end 466 being a ground contact, and the second and third contacts going to the controller. Alternatively, the three contacts can be for the circuits shown in FIG. 7B, with the first contact being ground, the second being the contact to the base of the transistor and the third being the contact to the input of the controller.

To measure hydration level, a sensing element, such as 452, is placed inside the cavity 462, with the door 464 closed, but with a small portion of the sensing element 452 exposed from the first end 466 of the hydration sensor 450. The sensing element 452 is touching the contacts 470; this can be done by having the closed door 464 pushing the element 452 to couple to the contacts. As shown in FIG. 8B, the user inserts the hydration sensor 450 under his tongue and pushes the switch 458 to activate the sensor 450, which can activate the timer 456. The saliva from the user touches the exposed portion 472 of the sensing element 452 and wicks up into the sensing element 452. When the saliva lowers the resistance between the first and the second contacts from the first end 466 to a first preset value, the timer 456 starts counting. When the saliva lowers the resistance between the second and the third contacts from the first end 466 to a second preset value (which can be the same as the first preset value), the timer 456 stops counting. The time elapsed or the number of counts provides an indication to the hydration level of the user.

In one embodiment, to improve the electrical connection between the sensing element 452 and the contacts 470 in the sensor housing, there is an elastomer or a small spring under the door 464 in the vicinity of the contacts 470. When the door 464 is closed, the elastomer or spring presses the sensing element 452 against the contacts 470, which enhances or ensures electrical connection between the sensing element 452 and the contacts 470.

In one embodiment, the contacts 470 are close to the first end 466 of the sensor housing 454. They are much closer to the first end 466 than other edges (e.g. 474) of the sensor housing, such as the left and the right edge. This will ensure that the hydration measurement at the contacts is from saliva coming through the first end 466 of the sensor housing, and not from other edges, such as 474.

In one embodiment, the sensing element 452 shown in FIG. 8A is applicable for more than one-time use. For example, the sensing element 452 can be a piece of blotting paper. After it is used, one can allow it to dry and then use it again. In another embodiment, the sensing element 452 is a piece of cloth, such as polyester cloth. After it is used, one can wash the cloth and then use it again.

In one embodiment, there are multiple pieces of the sensing elements 452 in the sensor housing 454. For example, the sensing elements 452 can be provided in a roll. The roll or multiple pieces can be serrated so that after the user has used one piece, the user can pull out that piece (such as from the first end 466 of the sensor housing 454) and remove it at the serrated region. This also brings a new sensing element into position for a next measurement.

A number of embodiments of hydration sensors and sensing elements have been described that are disposable, and a number of embodiments have been described that are applicable for more than one-time use.

In yet another embodiment, the sensing element is re-usable. For example, the sensing element can be suitable for continual use. In one embodiment, a re-usable sensing element includes a small channel (or tube) where capillary action can bring saliva up the channel. In another embodiment, pumping action can also bring saliva up the channel. There are also at least three contacts on the inside of the channel, with, for example, the first two contacts being used to indicate starting of measurements, and, for example, the second and third contacts being used to indicate the end of the measurements. Each contact has its corresponding electrical wire as leads to allow the contacts to be measured. The plurality of contacts are spaced apart up the channel. To determine the hydration level of the user, the channel is positioned inside the mouth of the user, and the resistances between or among the contacts are measured.

Figure 9:
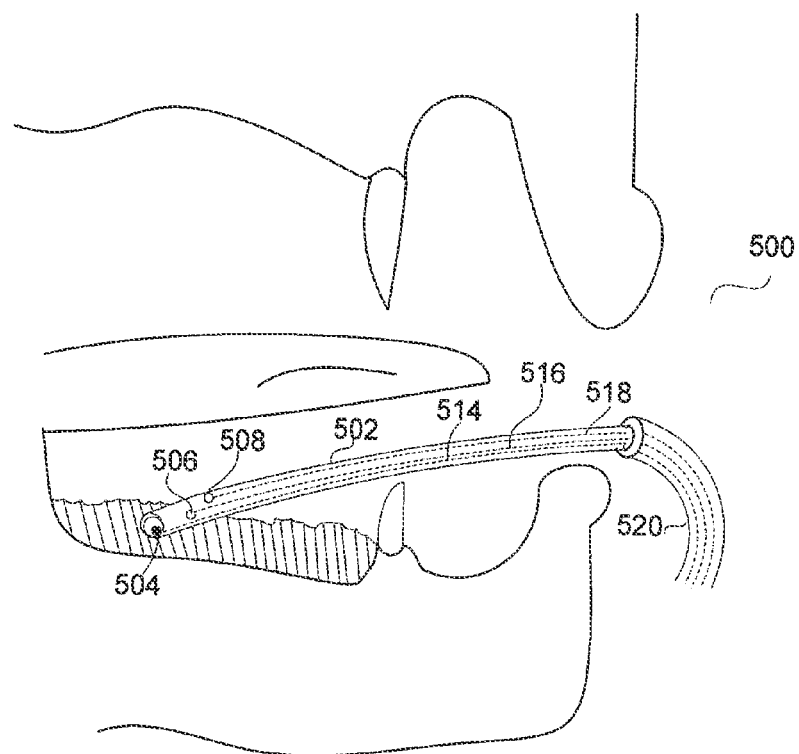
FIG. 9 shows a reusable hydration sensing element according to an embodiment of the invention.

FIG. 9 shows an embodiment of a hydration sensing element 500 that is a re-usable type. In this embodiment, the channel of the re-usable sensor is a hollow tube 502 with a small diameter. In one embodiment, because the tube's inner diameter is small, fluid can wick up the tube based on capillary action. In one example, the tube has an inner diameter of about 9 mils. In another example, the tube has an inner diameter of about 5 mils. The tube can be made of different types of materials, such as glass, nylon, polycarbonic and acrylic. In one example, the tube is made of hydrophilic materials tended to be wetted by water, which can enhance the capillary action. Alternatively, the tube can be made of different types of materials, but coated on its inner surface with a surface coating of materials that tend to be wetted by water.

The sensing element 500 includes a number of metallic contacts. In one embodiment, there are three contacts 504, 506 and 508, with at least two of them positioned internal to the tube 502. The contacts are spaced apart up the tube 502, such as in a linear manner. As an example, the first contact 504 is close to or at the opening of the tube 502. The second contact 506 is at a certain fixed distance from the first contact 504, and the third contact 508 is further up the tube 502. Each contact is connected to a conducting wire or a conductor to electrically extend the contacts out of the tube. For example, as shown in FIG. 9, a first wire 514 connects to the first contact 504, a second wire 516 connects to the second contact 506, and a third wire 518 connects to the third contact 508. In one embodiment, for structural reasons, the wall thickness of the tube 502 increases further away from the opening of the tube. For example, in FIG. 9, the hollow tube 502 inserted inside the mouth is connected through an air-tight joint to another hollow tube 520 that has a thicker wall.

To determine the hydration level of the person, as shown in FIG. 9, a portion of the hollow tube 502 is positioned inside the mouth, probably below the tongue of the user. Then the resistance between at least two of the contacts is measured through their corresponding conductors to determine the hydration level of the user.

Figure 10B:
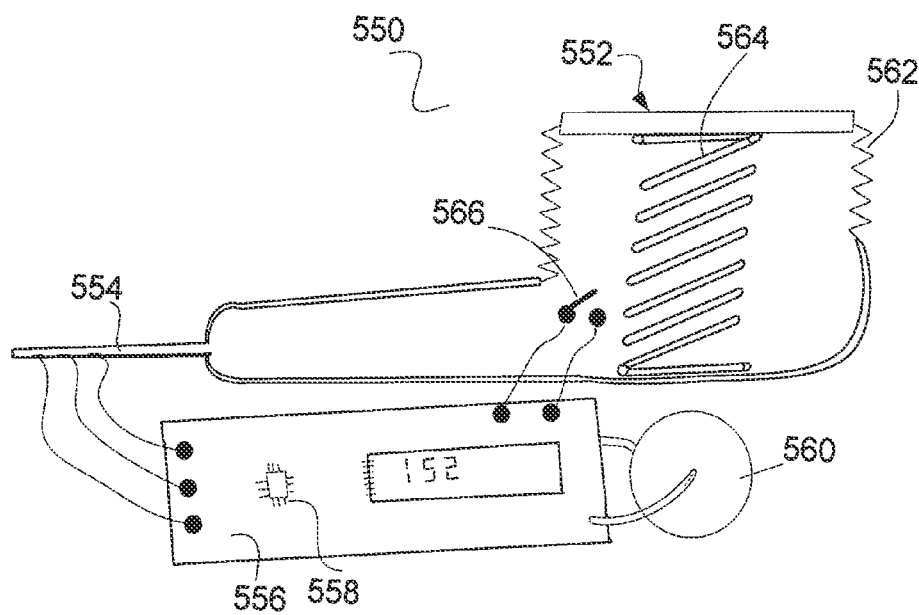
FIGS. 10A-10B show an embodiment of a re-usable hydration sensor based on a mechanical pump according to the invention.
Figure 10A:
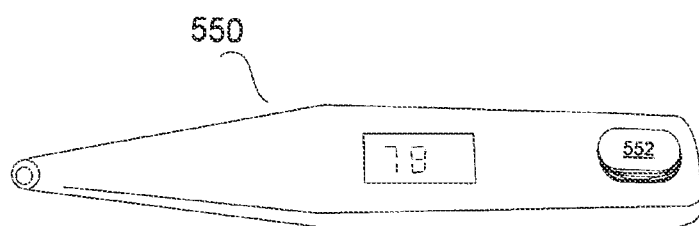

There can be different ways to clear the saliva from the tube. One approach is based on a mechanical pump. FIG. 10A shows an embodiment of a re-usable hydration sensor 550 based on a mechanical pump 552. FIG. 10B shows some of the components inside the sensor 550. As in FIG. 9, the sensor 550 includes a channel or a hollow tube 554 with a small inner diameter. Inside the tube 554, there are a number of electrical contacts. In the following example, assume that there are three contacts, similar to the three contacts in FIG. 9, with three wires from the three contacts. The three wires from the three contacts are used to measure the resistances between or among the contacts. In one embodiment, the three wires are connected to three connection points on a printed circuit board 556. In one embodiment, the circuitry on the board 556 includes those shown in FIG. 7A or 7B, with a microcontroller 558. There can also be a LCD display or other types of display for the controller 558. The sensor 550 can be operated by a small battery, such as a coin-cell battery 560.

To clear the saliva inside the tube 554 of the sensor 550 shown in FIG. 10B, the user can press a mechanical pump 552, which can be bellows 562 with a spring 564. When the bellows 562 are pressed down, air is expelled from the sensor 550, pushing any saliva out from the tube 554. In one embodiment, when the bellows 562 are pressed down beyond a certain preset point, a switch 566 is triggered, which activates the circuitry on the printed circuit board 556 to measure the resistance value between at least two contacts.

After being pressed, as the bellows 562 expands, a small vacuum is created. The flow rate of saliva up the tube 554 depends on the sucking force due to the vacuum created, the diameter of the tube and the viscosity of the saliva in the user's mouth. The time elapsed for the saliva to move, such as from the second to the third contact in the tube, is proportional to the vacuum and the saliva viscosity. The viscosity is inversely proportional to mouth hydration. By measuring the time elapsed, the sensor 550 can determine the viscosity of the saliva in the user's mouth.

In one embodiment, the pressure created by the vacuum is constant. This is accomplished through different ways, for example, by using a spring with a constant spring force, or a hollow sphere of rubber (like an eye-dropper bulb) for the bellows. To illustrate, one way to make a spring with a constant spring force is to use a long compression spring of fine spring wire (such as 8" long) and compress the spring into a short spring (such as 0.4" long). The spring force from the compressed spring is substantially constant.

In another embodiment, the pressure created by the vacuum is also measured by a vacuum pressure sensor inside the bellows for determining the viscosity of the saliva.

In one embodiment, there is a hole at the top surface of the bellows. When the bellows 562 is pressed, the finger pressing the bellows 562 covers the hole and air is pushed out of the tube 554. After being pressed, when the bellows 562 expands, the hole is exposed to suck air back into the bellows 562. With the hole being of sufficient size, no vacuum is created. The flow rate of saliva up the tube 554 depends on the viscosity of the saliva in the user's mouth.

In one embodiment, after saliva is removed from the tube by a pump or other methods, there might be a small droplet of saliva still remaining at or hanging onto the opening of the tube. One way to remove the droplet is to wipe the opening of the tube with a piece of cloth to absorb the droplet.

In one embodiment, the sensor shown in FIG. 10B also includes a memory device and a connector. The connector could be a standard USB connector. The memory device can keep track of, for example, the hydration measurements made and the time the measurements were made. Through the connector, one can upload the measurements to another device or instrument to analyze the data. This other device or instrument can be a computer with analysis software.

In one embodiment, a hydration sensing element can be attached to the user, either directly (such as on the user's ear) or onto something worn by the user (such as the user's eyeglasses, hats or clothes). For example, the sensing element can include an attaching mechanism, such as a clip, which can attach the sensing element to the user. In one embodiment, with the element attached or worn, the tube for saliva to move or seep into is allowed to be within the user's mouth. In one embodiment, the sensing element can measure the saliva of the user continually at predetermined intervals.

In one embodiment, the sensing element can also include a wireless transceiver, which is configured to allow information related to the measurements to be wirelessly transmitted to another electronic device, such as a portable device carried by the user or someone close to the user. In one embodiment, the portable device after analyzing the measurements, wirelessly transmits an indication to the sensing element (e.g. the user needs to drink), and the sensing element can alert the user. Alternatively, the portable device directly provides the indication to the user.

In one embodiment, the portable device can transmit information related to the measurements wirelessly to a remote electronic device (as opposed to, for example, a local device, like a portable device carried by the user). The remote electronic device can be a remote station. For example, if the user is a marathon runner, a remote station can continually monitor and analyze the runner's hydration level. Based on the analysis, if the runner needs to drink, the station can wirelessly send a signal to the portable device, which can then give a signal to the runner. If the portable device is carried by a support team for the runner, the signal will be provided to the support team. The signal can be, for example, a beeping signal, a message or a blinking LED to alert the runner to drink fluid.

In one embodiment, the portable device or the remote electronic device, based on information about the climate and other information, can advise the user or his support team on how much the user should drink at the next water/fluid location. The advice can also depend on the position of water/fluid locations (or other information regarding the race) and the location of the user, which can be identified through a positioning device, such as a global positioning device, carried by the user. In one embodiment, the user's location information can be wirelessly received by the remote station as well.

In one embodiment, the sensing element is connected to a portable device or another electronic device, through a wired connection.

FIGS. 11A-11D show an embodiment of a re-usable hydration sensor 600. It can be similar to the one shown in FIG. 10A. The re-usable hydration sensor 600 can be attached to or worn in the mouth of a user. In this embodiment, the sensor 600 is inside the mouth and is configured to fit on at least one tooth of the user. In one embodiment, the sensor 600, as shown in FIGS. 11A-11D, is a bitable hydration sensor, which can remove saliva from a tube when the user appropriately bites on it.

Figure 11A:
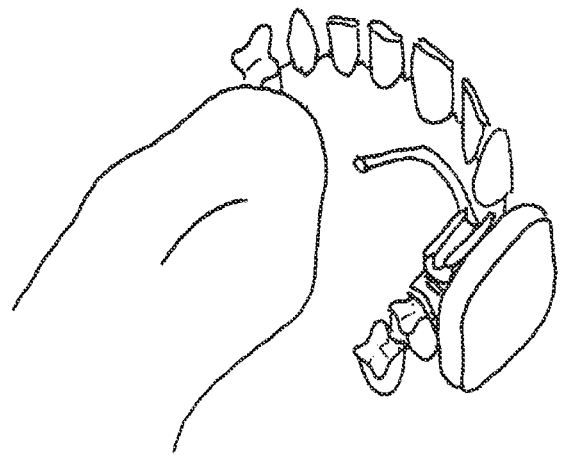
FIGS. 11A-11D show a re-usable hydration sensor clipped to the mouth of a user according to one embodiment of the invention.
Figure 11B:
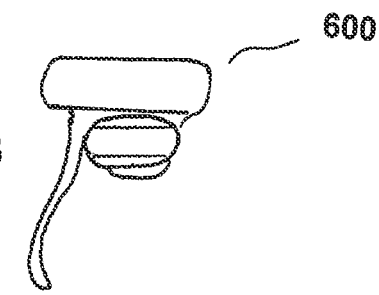
Figure 11C:
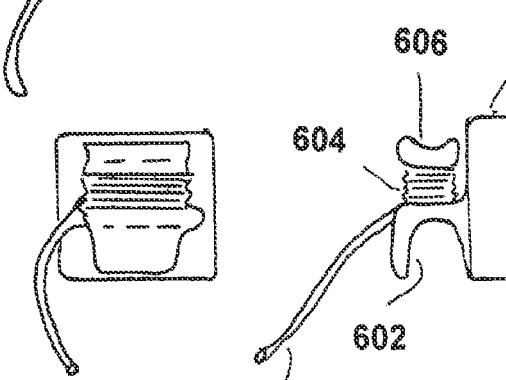
Figure 11D:
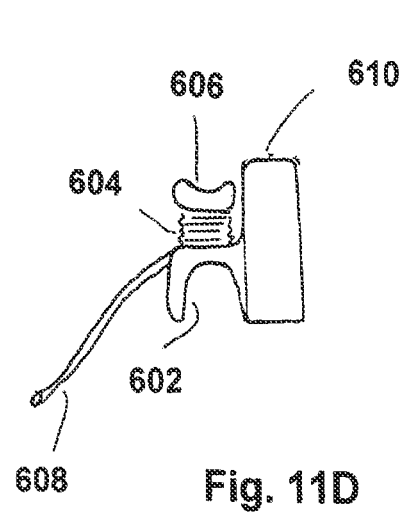

FIG. 11A shows the bitable sensor 600 inside the mouth of the user. FIGS. 11B-11D show the top, side and rear view of the bitable senor 600, respectively. The bitable sensor 600 includes a U-shape seat 602, which in the figure is shaped to sit on the lower right first molar. On top of the seat are bellows 604, with a top cover 606. The top surface of the top cover 606 can be shaped to fit the upper right teeth of the user.

As in the embodiment shown in FIG. 10A, saliva gets into a tube 608 of the bitable sensor 600. To remove saliva in the tube, the user can bite on the bellows 604 of the bitable sensor 600. In one embodiment, when the user bites on the bellows 604, the sensor electronics are activated, such as similar to the embodiments shown in FIG. 10B. In another embodiment, the sensor electronics are activated by the tongue pushing an on/off button, which can be on a side surface of the sensor, such as there can be an on/off button on the inner side surface of the U-shape seat 602.

In one embodiment, the bitable sensor 600 further includes a casing 610 that carries circuits for a power source, such as a battery. In another embodiment, the casing also carries a wireless transmitter. After the sensor has taken measurements, the transmitter transmits the measurements to, for example, a portable device, which, for example, can be carried by the user or another. The portable device can analyze the measurements received and provide feedback to the user, such as he is fine and does not need to drink yet.

In an alternative embodiment, the sensor can be provided in the mouth, but not be bite-activated. In one implementation, the tube or channel for the sensor can be cleared by using one's tongue to depress a bellows. In another embodiment, an electro-mechanical pump can be used to clear the tube or channel of the sensor.

Instead of a mechanical pump, a re-usable hydration sensor can include an electro-mechanical pump to clear saliva from a channel or tube. Under certain condition, the pump is activated electrically to pump saliva from the user's mouth. There are different ways to set the condition. For example, the pump is turned on periodically to clear the tube. In another example, the user can activate a switch to turn on the pump.

Figure 12:
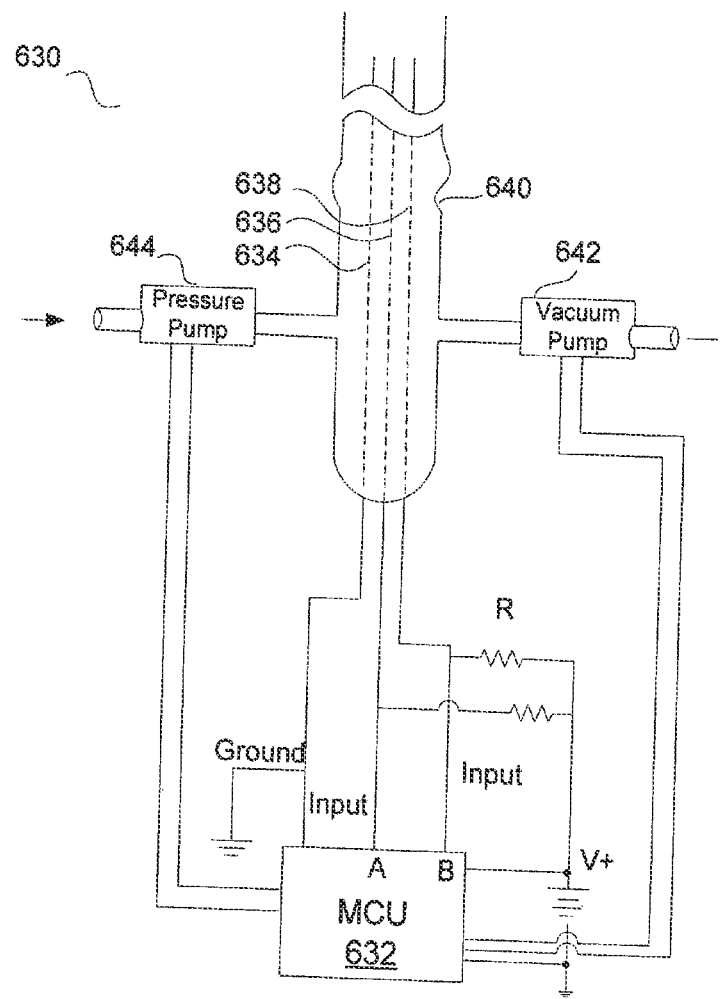
FIG. 12 shows an embodiment of different electrical components of a re-usable hydration sensor based on an electro-mechanical pump according to the invention.

FIG. 12 shows an embodiment of different electrical components 630 of a re-usable hydration sensor based on an electro-mechanical pump. Another such pump can also suck saliva into the sensor. The different conditions for activating the one or more pumps in FIG. 12 will be described in the following.

Figure 13:
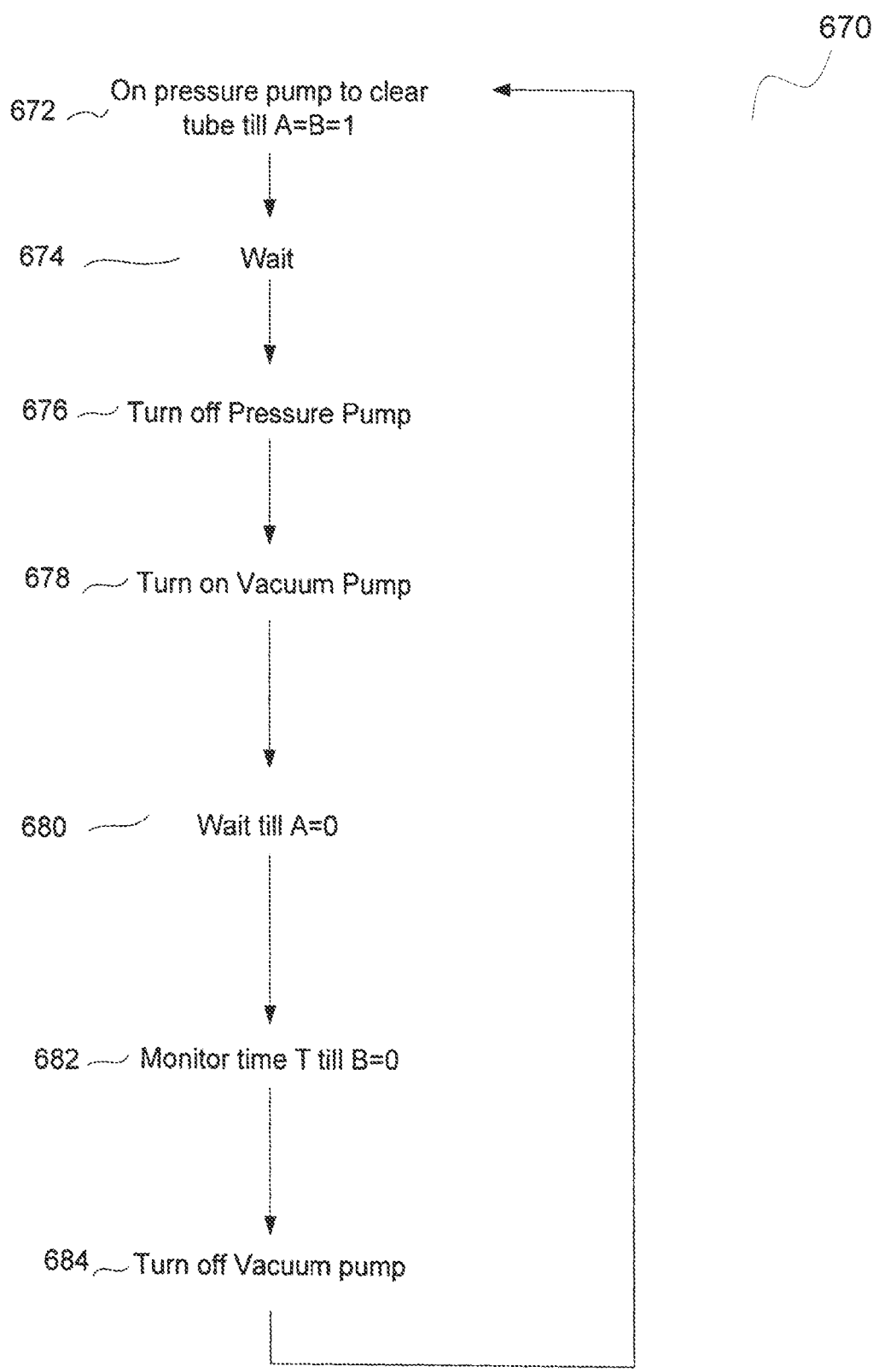
FIG. 13 shows an embodiment of a process for the hydration sensor shown in FIG. 12 according to the invention.

FIG. 12 shows three conducting wires 634, 636 and 638 leading into a microcontroller unit 632. In one embodiment, the three wires can be the three conducting wires from the three contacts of the sensing element shown in FIG. 9. In the following discussion, the three conducting wires are assumed to be three shown in FIG. 9, with 634 corresponding to 514, 636 corresponding to 516, and 638 corresponding to 518. FIG. 13 shows an embodiment of a process 670 for using the electronics of a reusable hydration sensor such as shown in FIG. 12. First, a pressure pump 644 is turned on 672 to push air through the tube 640, which would clear saliva from the tube 640. With the saliva cleared from the tube 640, the inputs A and B received by the microcontroller unit (MCU) 632 will read high or logic 1. At this instant, saliva is substantially cleared from the tube 640 so the resistances between both the first contact and the second contact, and between the second and the third contacts in the sensing element shown, for example, in FIG. 9 are high. By keeping the pressure pump 644 on for a preset amount of time, the tube 640 remains clear during that period. This amount of time can depend on how often the MCU 632 takes measurements. After waiting 674 that period, the MCU 632 turns off 676 the pressure pump 644 and turns on 678 a vacuum pump 642. The MCU 632 then waits 680 till the reading in its input A becomes low (logic 0). At this instant, the resistance between the first and the second contact, through the first 634 and the second 636 conducting wires, is low (or below a preset value) due to the saliva provided between the contacts. Then the MCU 632 monitors 682 the amount of time "T" till its input B also becomes low (logic 0). At this point, the resistance between the second and the third contacts, through the second 636 and the third 638 conducting wires, is low (or below a preset value), again due to the saliva provided between those contacts. Then the MCU 632 turns off 684 the vacuum pump 642. This time T is proportional to the pressure of the vacuum pump and the viscosity of the saliva. The viscosity inversely depends on how well hydrated the user is. The process 670 is repeatable.

In an embodiment that uses a vacuum pump to pull saliva up a tube or channel, the tube or channel uses hydrophobic materials, which can be more easily cleaned and dried for subsequent use. Examples of materials for the tube or channel include polypropylene or polyethylene.

In one embodiment, the embodiment 630 shown in FIG. 12 does not include a vacuum pump 642. After a preset amount of time of the pressure pump 644 being on, the MCU 632 turns off the pressure pump 644. Saliva, if there is any, moves up the tube 640 by capillary action. The MCU 632 then waits till the reading in its input A becomes low (logic 0). At this instant, the resistance between the first and the second contact, through the first and the second conducting wires, is low (or below a preset value) due to the saliva provided between the contacts. Then the MCU 632 monitors the amount of time "T" till its input B also becomes low (logic 0). At this point, the resistance between the second and the third contacts, through the second and the third conducting wires, is low (or below a preset value), again due to the saliva provided between those contacts. This time T is proportional to the viscosity of the saliva, which inversely depends on how well hydrated the user is. The process can be repeated.

Instead of using a pressure pump and a vacuum pump, in another embodiment, the user can blow into the tube to clear the tube. The MCU can measure the time T without needing the pumps.

A number of re-usable sensing elements have been described where there is a small channel, such as in a small tube. In one embodiment, the small channel with electrical contacts is formed using a printed circuit board. There can be a printed circuit board and another board with a trough on one side.

There are different ways to make the board with a trough. For example, a trough can be made as the board is injection molded, by making the trough a feature in the injection mold. Another way to make the trough can be by a milling machine. To illustrate, for example, the cross section of the trough is rectangular in shape, whose height and width dimensions are on the order of 5 mils. The board with the trough can be made of thermal plastic or other types of materials, such as silicone or Teflon. The board with the trough can also be, more generally, considered a trough in a substrate. In one example, the substrate can be a type of dielectric material. In another example, there can be a coating over the materials at least in the trough area where the coating tends to be wetted by water.

Regarding the printed circuit board, a number of conducting lines are formed on it. They can function as the conducting wires shown in FIG. 9, such as 514, 516 and 518. Then an insulating layer is formed over the lines. This layer can be a plastic layer on the printed circuit board, such as a solder mask. There are holes in the insulating layer for contacts. The conducting lines in the vicinity of the holes can be gold plated, and they can serve as contacts. These contacts can function as the contacts in FIG. 9, such as 504, 506 and 508. The gold plating helps prevent corrosion.

The two boards are then joined together, with the trough aligned to the contacts. There are different ways to join the boards together, such as by ultrasonic welding, adhesives or using screws. In another embodiment, the boards are joined together using a double-sided sticky tape, with the tape having a hole in the area of the trough. If the trough is rectangular in cross-section, the walls of the trough can serve as three of the sides, with the printed circuit board serving as the final side of the channel.

In yet another embodiment, a small channel is formed using tapes. For example, after forming the conducting lines on a board, two pieces of tapes are put on the board to serve as the side walls of the channel. Then a piece of acrylic is put on top of the tapes. Different means can be used to hold the structure together. For example, the tapes are double-sided sticky tapes; glue can be applied onto the top of single-sided sticky tapes; or glue can be applied onto the edges of the structure to hold it together. The boundaries of the channel would be the board, the tapes and the acrylic, with the board and the acrylic forming two surfaces and the tapes forming the side walls. The thickness of the tapes determines the height of the channel. In one example, the thickness of the tapes is 2 mils and the width of the channel is 100 mils. Instead of using tapes as the side walls of the channel, in one embodiment, solder mask or paint is used as the side walls of the channel.

In another embodiment, the piece of acrylic can be molded with two ribs or rails, which serve as the side walls, and which are placed against the circuit board. The structure can be secured with glue on the outside. In this embodiment, one surface and the two sides or walls of the channel are formed by the acrylic piece, and the other surface is formed by the circuit board.

In one embodiment, one or more of the walls or surfaces of the small channel or tube are textured. A matte surface can be more hydrophilic. As an example, at least a portion of the channel is made of acrylic, and the acrylic walls or surfaces are textured. Also, when the matte surface is wet, it is transparent, and when it is dry, it is translucent. Depending on whether an area is transparent or translucent, one can determine whether saliva has moved into the area.

In another embodiment, a small channel can be opened and closed. For example, the channel can be opened by the action of a lever, and closed by the action of a spring. In this example, one can open the channel to wipe it clean and to have it dried.

A number of re-usable hydration sensing elements have been described, each having a channel for saliva to get in. In one embodiment, after such a sensing element has been used, the channels can be cleaned using alcohol, such as rubbing alcohol. For example, the opening of a channel can be immersed in alcohol for a duration of time. By, for example, capillary action, the alcohol goes up the channel. Then the opening of the channel is removed from the alcohol. In one embodiment a pressure pump can be used to remove alcohol from the channel. In another embodiment, the alcohol in the channel is removed by evaporation. The user can perform this operation a few times if desired to further clean the channel.

In yet another embodiment, a hydration sensing element can be based on piezoelectric effect. For example, the element includes a piezoelectric element coupled to a piece of absorbent medium, such as a thin sponge. The medium expands and gets heavier when it absorbs fluid. As the medium expands, the element is flexed, and its electrical impedance changes. The impedance of the piezoelectric element is measured, for example, at an AC frequency by an impedance measuring circuit. The AC frequency can be, for example, approximately 3 kilohertz. The degree of change depends on the expansion of the medium, which depends on the amount of fluid the medium absorbs. The amount absorbed in turn is a function of the viscosity of the saliva in the mouth. Thus, by measuring the impedance or the change in impedance as a function of time, one can determine the dryness of the mouth. To measure the swelling of an absorbent medium using a piezoelectric cantilever over the medium is known in the art, and will not be further described. In one embodiment, such a hydration sensing element is used in a hydration sensor. The sensor can further include different electrical components, such as a controller, a display, a switch and a power source. The controller can monitor the measured impedance or the change in impedance, and convert the monitored results to hydration level, which can be displayed accordingly. The sensor can be handheld, attachable to or mounted on the user, according to different embodiments.

Another type of hydration sensing element that is based on measuring the viscosity of fluid is described in U.S. Pat. No. 6,584,831, which is hereby incorporated herein by reference. This type of element can be incorporated into different types of sensors, as previously described.

In one embodiment, a hydration sensor or a hydration sensing element as previously described is calibrated for a user. After the calibration is performed, that type of sensing element or that sensing element can be personalized to the user.

Figure 14:
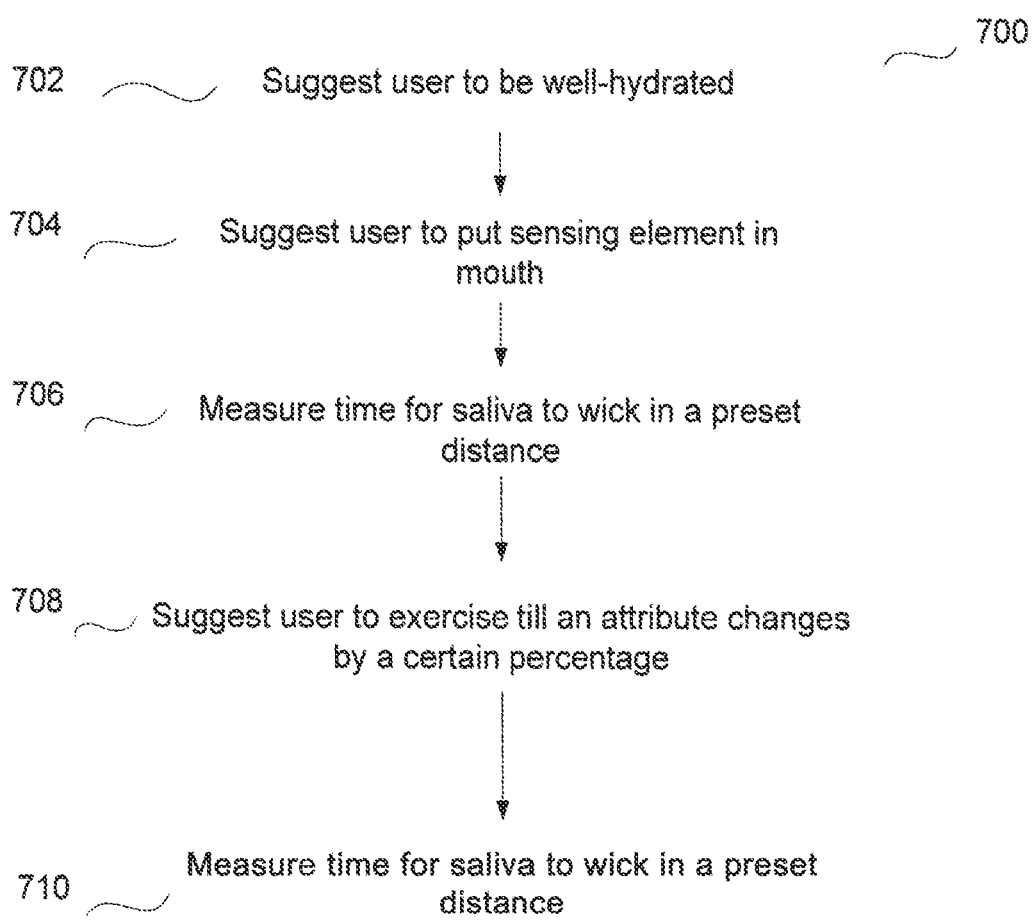
FIG. 14 shows a process to calibrate a hydration sensor according to one embodiment of the invention.

In the following, the sensing element, such as the one shown in FIG. 6A with three conducting lines, is used as an example, though other hydration sensing elements or sensors are applicable. The calibration method can be implemented by a computing device, which can be a handheld device. FIG. 14 shows one embodiment of a calibration process 700.

First, the method 700 suggests 702 the user to be well-hydrated. This can be accomplished, for example, by asking the user to drink 8 ounces of fluid every 2 hours until his urine is clear. When the urine is clear, the user is assumed to be well-hydrated. The suggestion can be through voice, visual or audiovisual techniques from a computing device. Then the method suggests 704 the user to put the sensing element into his mouth, and measures 706 the time T it takes for the user's saliva to wick a preset distance. This can be by measuring the time T when the resistance between the middle conducting line and either or both of the two outer conducting lines drops to a preset value. This time T becomes the reference time or base line of the user. It can be used to indicate the user to be well hydrated. The method then suggests 708 the user to exercise till a user's characteristic changes by a certain percentage. At that point, again the method measures 710 the time T1 for the user's saliva to wick a preset distance, which can be the same preset distance as last time. The method or process can ask the users to continue to exercise until the certain characteristic changes by a second preset value. Again perform the time measurement for the user's saliva to wick the preset distance. This third time T2 will be the time indicating the user is dehydrated to a point where the user's characteristic has changed by the second preset value. This process can repeat by continuing to ask the user to exercise. After the measurements, the sensor is calibrated for the user. Note that instead of measuring the time for a preset distance of wicking, in another approach, the method can measure the distance wicked for a preset amount of time.

In the calibration process, the user's characteristic or attribute can be the user's weight. As an example, the user can ride a stationary exercise bicycle for a duration of time, such as 15 minutes. Then, the user gets off the bike, removes sweat with a towel and measures his weight with an accurate scale. The user keeps doing this until his weight drops by such as a certain percentage. The time T1 can indicate that the user is dehydrated to the point where the user has lost 0.5% of weight, and the time T2 is where the user's weight loss is 1%. In the future, by measuring the time for saliva to wick the preset distance, the sensing element would be able to indicate how much fluid relative to the person's weight the user needs to drink just to replenish his weight loss due to, for example, dehydration.

Instead of using weight loss, in another embodiment, another attribute of a user can be measured to calibrate a hydration sensor. For example, instead of measuring weight loss, the body temperature of the user is measured to calibrate a hydration sensor.

The calibration process can be performed with respect to a type of sensing element for a group of users. The group of users might have certain similar characteristics because the calibration results might depend on the certain similar characteristics of the users, such as weight and age. For example, all of them are normal-weight adults, or all of them can be 30% overweight. Using the same approach as above, for example, in FIG. 14, the method averages the time measured for all of the users at each step. For example, the average time T1 would be the time indicating a user in that group using that type of sensing element being dehydrated by 0.5% of the user's weight. Then, in the future, by measuring the time for saliva to wick the preset distance for that type of sensing element and for users with the similar characteristics, the sensing element would be able to indicate how much fluid relative to a user's weight that the user needs to drink just to replenish his weight loss due to, for example, dehydration.

In one calibration process, a timer measures the time elapsed for a fixed distance wicked by saliva. This process is applicable for many of the different types of sensing elements and sensors previously described, such as the ones shown in FIGS. 1C, 2, 3A, 4, 5B. In yet another embodiment, instead of measuring time elapsed for a fixed distance wicked by saliva, a hydration sensing element can measure the distance wicked by saliva during a fixed time. This approach is applicable, for example, for the sensing elements or sensors shown in FIGS. 1C, 2, 4 and 5B.

In one embodiment, a hydration sensor includes a hydration sensing element to determine the optimal amount of fluid a user should consume in order for the user to be well-hydrated. The sensing element can have been calibrated by a method as described above. Then, based on measuring the hydration level of the user with the element, the sensor determines the optimal level of fluid the user should consume for the user to be well hydrated, and provide a recommendation to the user.

Figure 15:
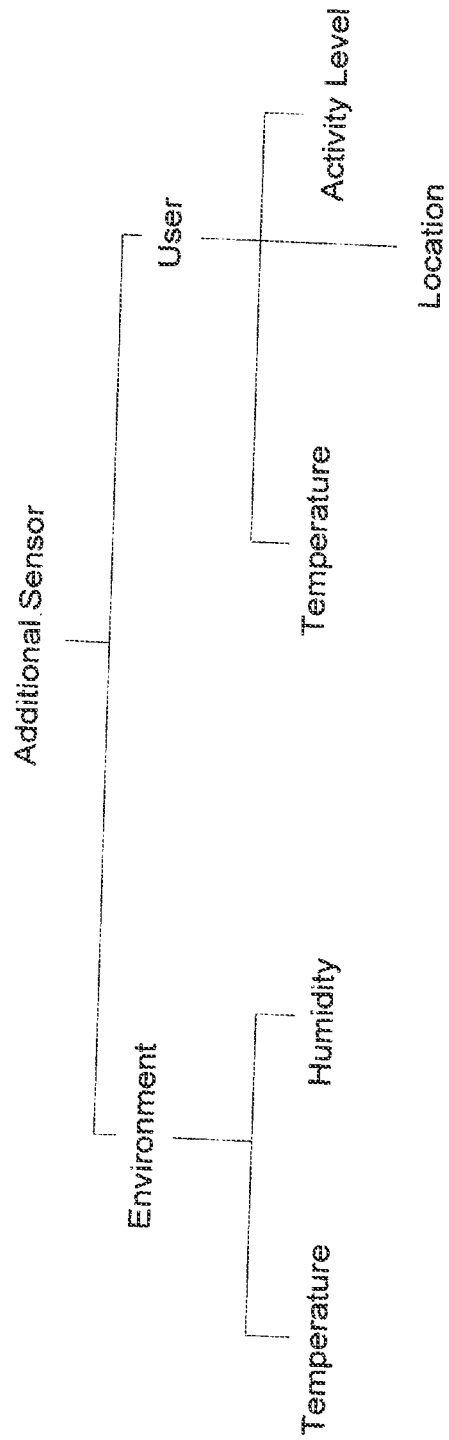
FIG. 15 shows examples of additional sensors applicable for appropriate hydration measurements according to different embodiments of the invention.

In another embodiment, the optimal amount of fluid to be consumed for a user can also depend on other factors of the environment a user is in. For example, a hydration sensor includes a hydration sensing element (such as one of the elements disclosed) and an environmental sensor that senses an attribute of the environment the user is in. FIG. 15 shows examples of environmental sensors applicable for appropriate hydration measurements according to different embodiments. For example, a temperature sensor can be configured to measure the temperature of the environment where the user is in, and the sensor is coupled to a hydration sensing element. As another example, a humidity sensor (coupled to a hydration sensing element) is configured to sense the humidity of the environment of the hydration sensing element. Based on one or more of these additional environmental sensors, the hydration sensor determines the optimal amount of fluid the user should consume. In one embodiment, after the determination, the sensor provides a recommendation to the user. The recommendation can be, for example, visual or audio.

In yet another embodiment, the optimal amount of fluid to be consumed can depend on one or more additional attributes regarding the user, other than the hydration level of the user. In one embodiment, a hydration sensor includes a hydration sensing element (such as one of the sensing elements as disclosed) and a user-attribute sensor that measures an attribute of the user other than the user's hydration level. The optimal amount of fluid the user should consume depends on both the measurements by the hydration sensing element and by the user-attribute sensor. For example, one user-attribute sensor is a temperature sensor for sensing the temperature of the user. Another is a position sensor for identifying the location of the user. Yet another example for a user-attribute sensor is an activity sensor, such as a pedometer, for sensing the activity level (or the lack of activity) of the user.

Information from such one or more additional sensors can be used to adjust the signal for the user or to help determine the appropriate amount of fluid the user should consume. For example, if the temperature is around 72 degrees Fahrenheit, the time as measured by a hydration sensor indicating that the person needs to replenish 0.5% of his body weight of fluid is T1. If the temperature of the environment is high, such as more than 100 degrees, the hydration sensor automatically shortens the time based on a predetermined value.

As shown in a number of embodiments, such as the one shown in FIG. 1B, at least one surface of the sensing element can be made of a piece of opaque materials. In one embodiment, promotional materials or different designs can be printed on that surface. In another embodiment, there can be promotional materials on the sensor. In yet another embodiment, promotional materials can be on a bottle coupled to a hydration sensing element, such as the one shown in FIG. 2.

In one embodiment, the hydration sensing element or sensor is incorporated into a structure that is in the shape of, such as, a spoon, a small cup, or a small container. To use such a sensor or sensing element to measure a user's degree of hydration, as an example, the user spits his saliva into the sensor, such as in the shape of a spoon, to measure the saliva.

In one embodiment, the hydration sensing element, such as the one shown in FIGS. 1A-1D, can be incorporated into a holder of a specific configuration, such as a handle or a stick. For example, a user can hold onto the holder with the sensing element attached to one end of the holder.

In one embodiment, there is a RFID tag coupled to or integral with a hydration sensor or sensing element. The tag can be used to provide, for example, an identification of the sensor, or the tag can be used to transmit wirelessly measurements from the sensor to another device.

In one embodiment, a hydration sensor also provides recommendation to a user using it to be aware of other factors that can affect hydration measurements. For example, an audio signal can tell the person to avoid eating food such as candies or chewing gums, or drinking any beverages, right before taking measurements because such food or water might affect saliva flow, which in turn would distort the hydration measurements.

A number of embodiments have been described where saliva flows into a channel, which can be a minute channel, through capillary effect. Other embodiments have also been described where saliva flows into a channel with the assistance of a vacuum pump, which can be a mechanical or electro-mechanical pump. In one embodiment, with the pump, the dimension of the channel can be larger because saliva flows up the channel not just based on capillary effect.

One or more types of hydration sensing elements or sensors can be used to provide an absolute index on the hydration level of a user. One approach to determine absolute index based on a sensing element is to compare the known viscosity of certain liquids (known standards) with the measured results. A standard curve can be obtained from the viscosities of the known standards. The measured results are then fitted to the standard curve to determine an equation or to create a table that correlates the measured results to the standard curve. In the future, based on the equation or the table, the absolute viscosity value can be determined from the sensor measurements.

Certain diseases can also affect the accuracy of the measurements. For example, a person with dry mouth or xerostomia may not give accurate results. Xerostomia could be due to genetics, radiation therapy, blood-pressure medication and autoimmune diseases. In one embodiment, a hydration sensor would warn or alert the user that if the user has sicknesses such as dry mouth, the measurements may not be an accurate measurement of his hydration level.

In yet another embodiment, a hydration sensor or sensing element, such as one or more of the previously described ones, is used for measuring symptoms related to the disease xerostomia or dry mouth of a user. Typically, the normal flow rate of saliva in an unstimulated manner is about 0.3 to 0.5 mL/minute. Values less than 0.1 mL/min are typically considered xerostomic. Flow rate and viscosity are related. In one embodiment, by measuring viscosity using, such as a viscosity sensor or sensing element as described, one can tell if a person has xerostomia. In another embodiment, the sensor or sensing element has previously been calibrated by a method as described, and the calibration can be for the person being measured.

In one embodiment, a hydration sensor or a hydration sensing element electrically couples to a bottle. In another embodiment, different electrical components in the sensor or sensing element can be incorporated in the bottle. Different embodiments regarding electrical components in a bottle have previously been described in one or more of the related patent applications identified above and incorporated by reference.

Figure 16A:
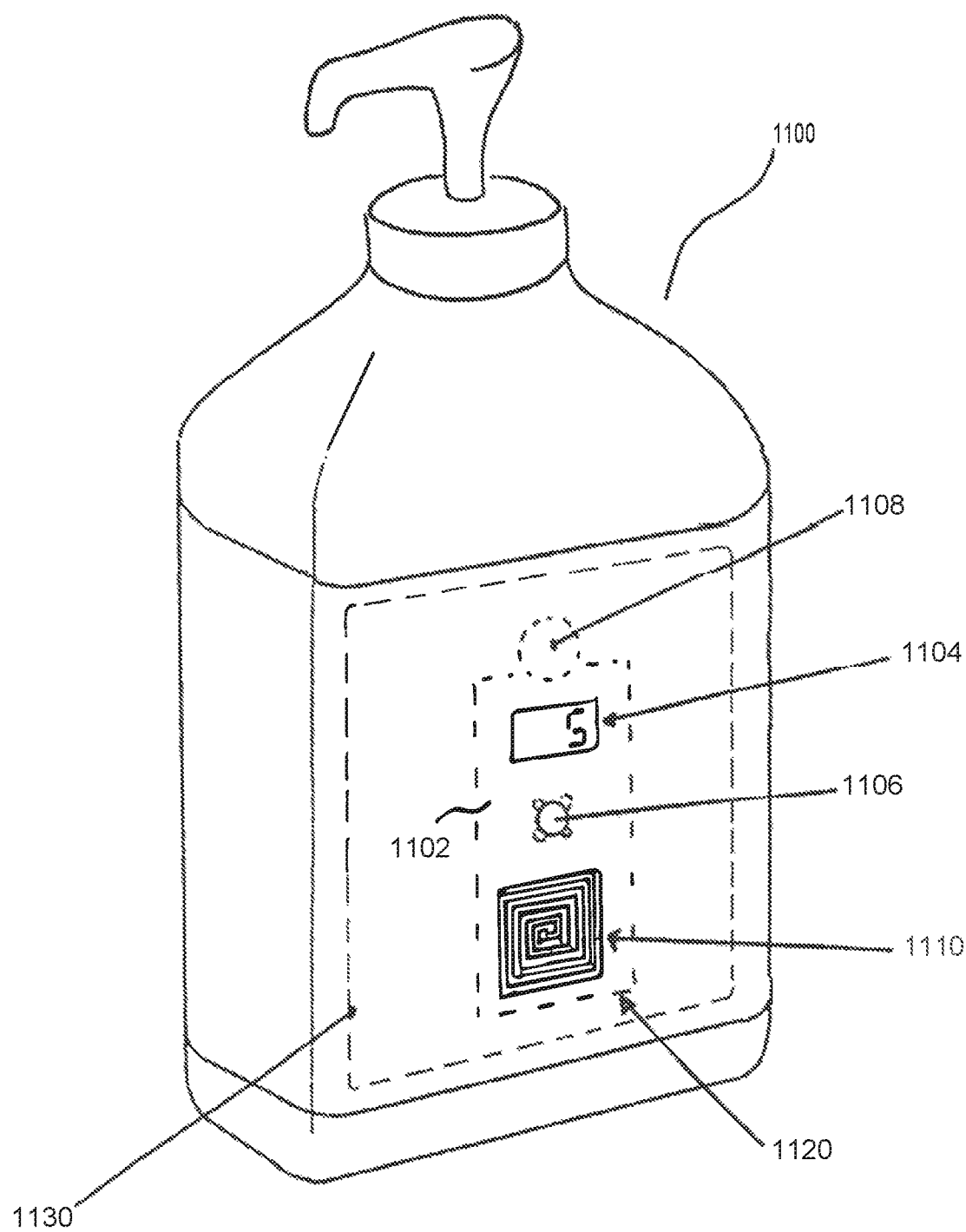
FIG. 16A shows a bottle of lotion with a moisture sensor according to one embodiment of the invention.

FIG. 16A shows a bottle of lotion 1100 with a moisture sensor 1102 according to one embodiment. The sensor 1102 is integral with or integrated into the bottle. The sensor 1102 can provide an indication regarding the dryness of a user's skin, and can provide a recommendation or suggestion regarding the application of lotion, such as whether the user should apply lotion.

Figure 16B:
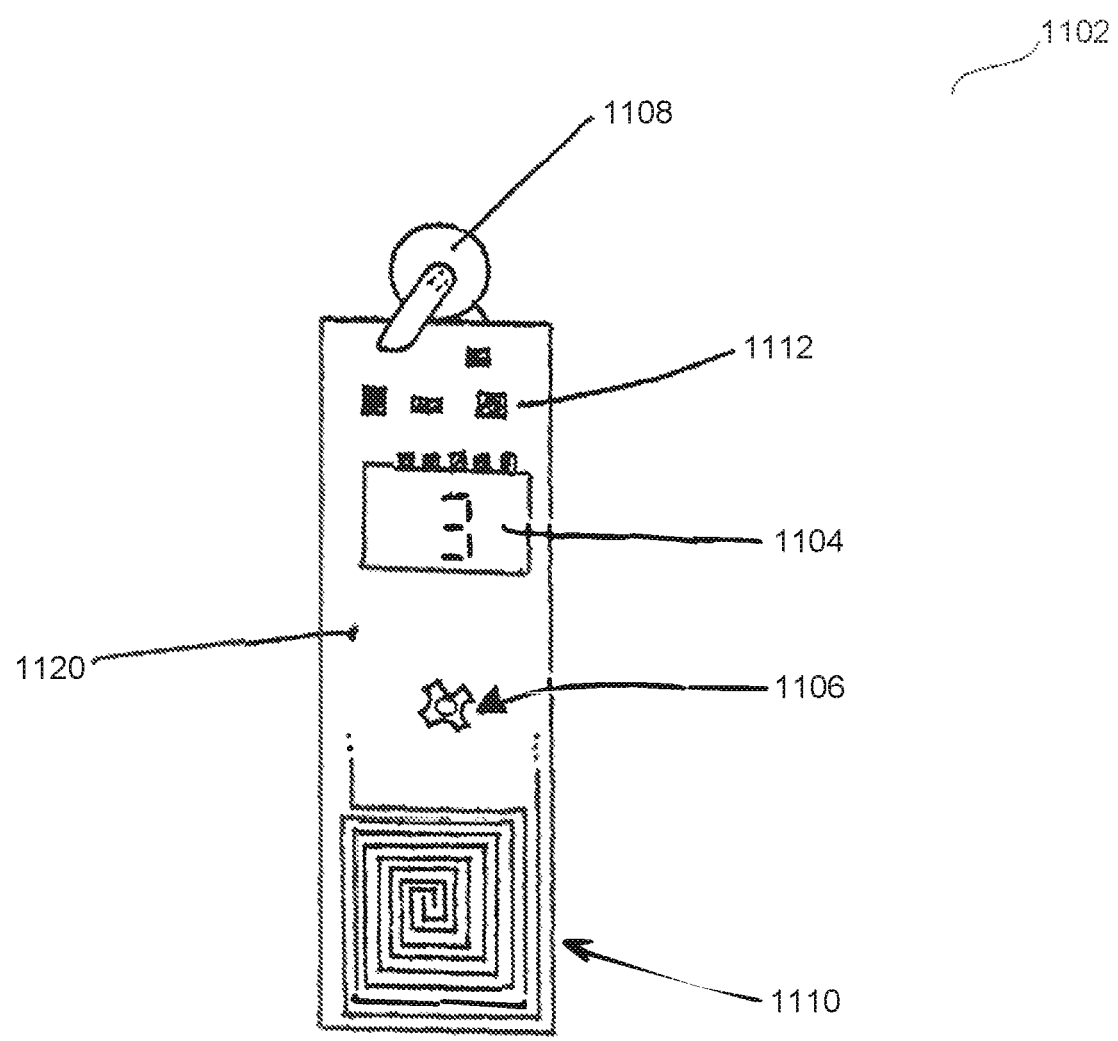
FIG. 16B shows a number of electrical components on a printed circuit board of a moisture sensor according to one embodiment of the invention.

FIG. 16B shows a printed circuit board 1120 with a number of electrical components for the moisture sensor 1102 according to one embodiment. The printed circuit board can be a rigid or a flexible printed circuit board. The electrical components include a display 1104, such as a LCD display, an on/off switch 1106, a sensor head 1110, and one or more integrated circuits 1112, with one being an electronic controller. The controller is configured to control operations of the electronics on the printed circuit, such as the display 1104. Another electrical component for the sensor 1102 is a power source, such as a battery 1108, which, in one embodiment, is a coin battery. In one embodiment, a sensor head 1110 is the part of the sensor 1102 that touches and measures the substance or the area to be sensed. The switch 1106 can be a dome switch. If a user wants to take a measurement, the user pushes the switch. This will turn on the sensor 1102 to measure skin dryness. Outputs from the measurements are shown on the display 1104. In one embodiment, the sensor 1102 is used with the bottle of lotion 1100. The sensor 1102 is an apparatus that provides an indication regarding the dryness of the user's skin. In one approach, the sensor 1102 uses capacitive effect to determine dryness.

In one embodiment, the sensor 1102 is referred to herein as a moisture sensor and it is used in conjunction with a bottle of lotion 1100 to assist the user of the bottle in determining whether lotion from the bottle should be applied to the user's skin. In another embodiment, the sensor 1102 is referred to herein as a moisture sensor and it helps the user determine whether the user's skin needs lotion, though the sensor may not be used together with a bottle of lotion.

Figure 16C:
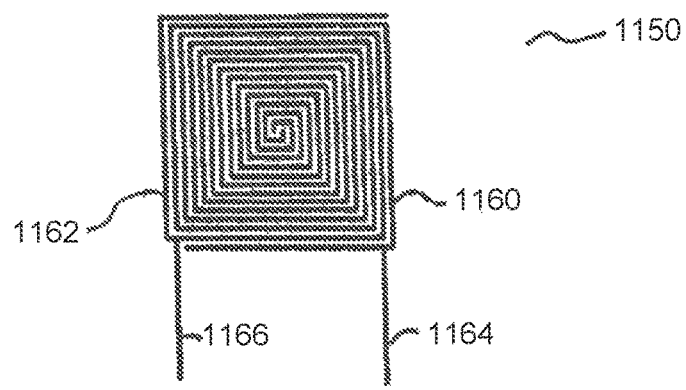
FIG. 16C shows different embodiments of electrical circuits for a moisture sensor head according to the invention.
Figure 16C:
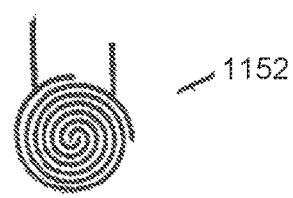
Figure 16C:
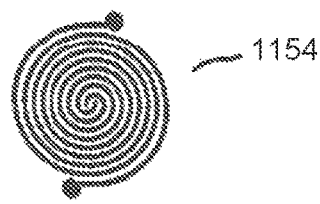
Figure 16C:
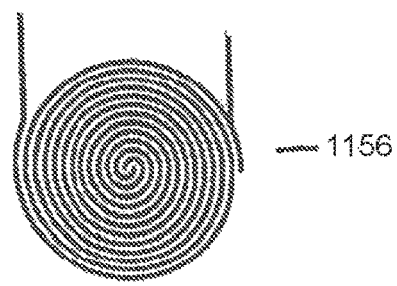

FIG. 16C shows different embodiments 1150, 1152, 1154 and 1156, of electrical circuits for a moisture sensor head 1110 that uses closely-spaced electrically conducting lines. One of the embodiments, 1150, is rectangular in shape, and the other three are circular or spiral in shape. They can be made by printing conducting lines on a printed circuit board. The conducting lines are typically covered by a thin layer of electrically insulating material. An example of such a layer of insulating material is a solder mask, a material commonly used in the circuit board industry. Each of the embodiments shown in FIG. 16C includes two conducting lines adjacent to each other and intertwined together, for example, in the shape of spirals. In one embodiment, the conductors are 10 mils wide, with 10 mils spacing between the lines. Using the rectangular embodiment, 1150, as an example, one can see the two conductors 1160 and 1162. Each of the conductors is connected to a lead, the conductor 1160 to the lead 1164, and the conductor 1162 to the lead 1166. The sensor 1102 (e.g., sensor body) measures the capacitance between the two conductors through the two leads. The capacitance depends on the dielectric constant of the materials adjoining the conductors. With the sensor head 1110 pressed against a piece of skin, the dielectric constant changes depending on the skin's moisture content. Different techniques are known in the art to measure capacitance, and will not be further described.

As an example, with the square embodiment 1150, if it is not touching any skin, the capacitance measured can be about 0.04 nF (nano-farads). When the sensor head is touching a dry skin, the capacitance measured can be about 0.09 nF, and when the sensor is touching a moist skin, the capacitance measured can be about 0.15 nF.

In the example shown in FIG. 16A, the sensor head 1110 is closer to the bottom of the bottle than the display 1104. In another example, the printed circuit board 1120 is switched 180 degrees, with the display 1104 being closer to the bottom of the bottle. In yet another embodiment, with the printed circuit board being a flexible printed circuit board, the printed circuit board does not have to be on a flat surface of the bottle. The printed circuit board could be on a curved surface of the bottle, and the bottle could have more curvature.

Figure 17:
FIG. 17 illustrates a person using a moisture sensor on a lotion bottle according to one embodiment of the invention.

FIG. 17 illustrates an example of a person using a moisture sensor on a lotion bottle according to one embodiment. The person turns on the sensor, and then presses the sensor head against her face to get a measurement. In one embodiment, the sensor tracks the measurements until changes in the measurements are within a preset threshold. Then the sensor takes that measurement as the final measurement.

In one embodiment, there is an indentation on the bottle surface to hold the printed circuit board 1120 with the battery 1108 so that the surface of the board is substantially flush with the outer surface of the bottle.

In the embodiment shown in FIG. 16A, the sensor 1102 includes a battery 1108. In another embodiment, the sensor can be powered by a fuel cell or a solar cell. In yet another embodiment, the bottle includes a latch or a door, to allow the power source, such as the battery, to be accessed (e.g., battery replaced).

In one embodiment, the sensor is water-sealed because the sensor might get wet or there could be moisture on the surface of the sensor. One way to seal the electrical traces on the printed circuit board 1120 is by covering them with solder mask. Other mechanisms of sealing the electrical traces include, for example, epoxy and adhesive tape.

There can be one or more labels 1130 on the bottle 1100. In one embodiment as shown in FIG. 16A, one can place the printed circuit board on the front surface of the bottle 1100 and then place a label 1130 over it. In one embodiment, the label 1130 has at least three openings, one for the switch 1106, one for the display 1104, with the third for the sensor head 1110. The sensor head 1110 can be covered or encapsulated by solder mask or other type of insulating film. The label 1130 can provide improved aesthetic appearance and/or serve to secure the moisture sensor to the bottle. The label could be a shrink-wrap on the surface of the bottle. The shrink-wrapping could be made of a piece of plastic material. Also, there could be, for example, a company logo and/or advertisement on the label 1130.

Figure 18:
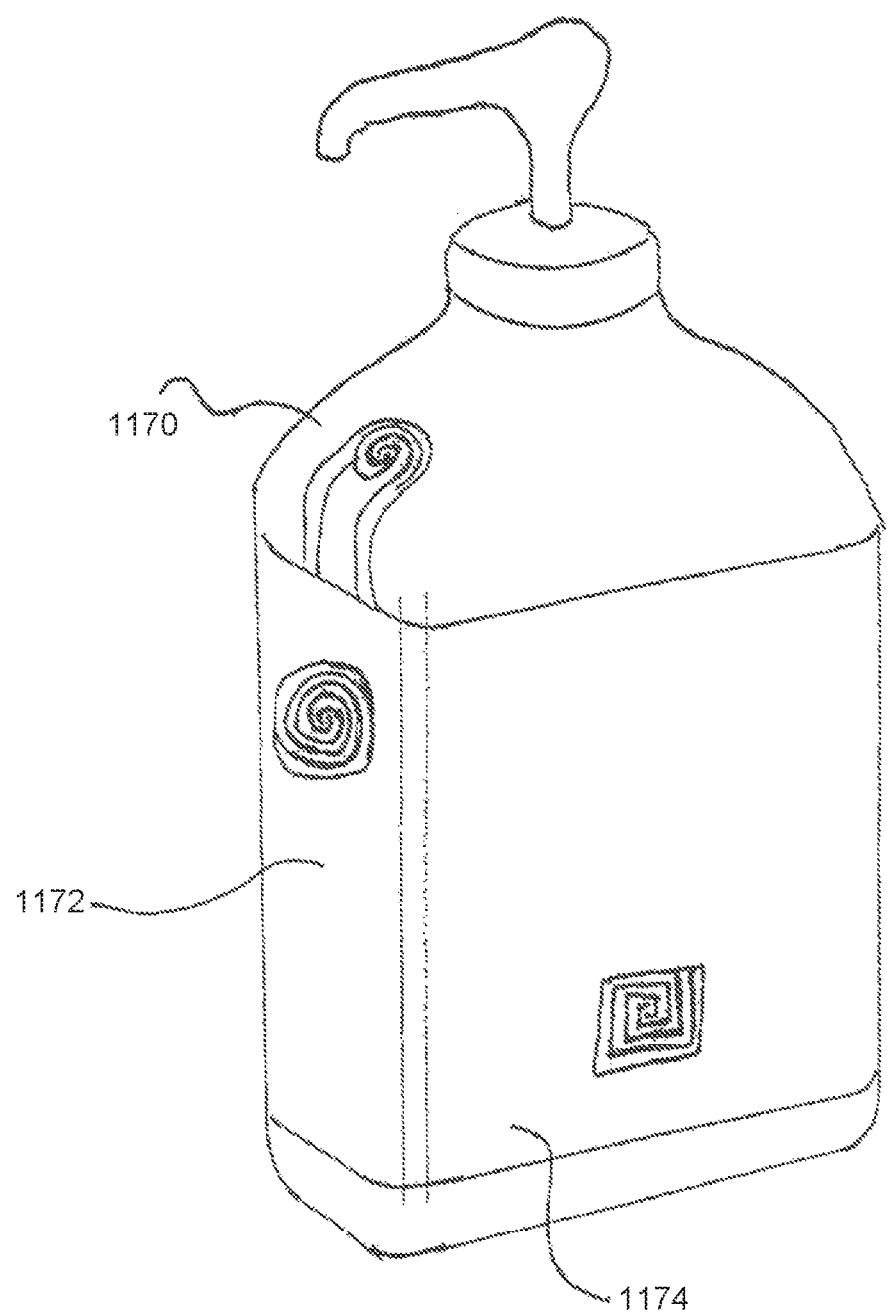
FIG. 18 shows different embodiments regarding the locations of a moisture sensor head that is integral with a bottle of lotion according to the invention.

FIG. 18 shows different embodiments of the locations of a moisture sensor head that is integral with a bottle of lotion. For example, the sensor head can be integrated on a shoulder 1170, on a side surface 1172, or on a front surface 1174 of the bottle. FIG. 16A shows the sensor also on a front surface of a bottle.

Instead of being integral with a bottle, in one embodiment, a moisture sensor is detachable from and can be attachable to the bottle. In one embodiment, the bottle can further include, for example, a clip, a band, a piece of string or a cord that can serve to attach the sensor to the bottle. In another embodiment, instead of the bottle, the sensor includes, for example, a clip, band, string or cord that can serve to attach the sensor.

Figure 19A:
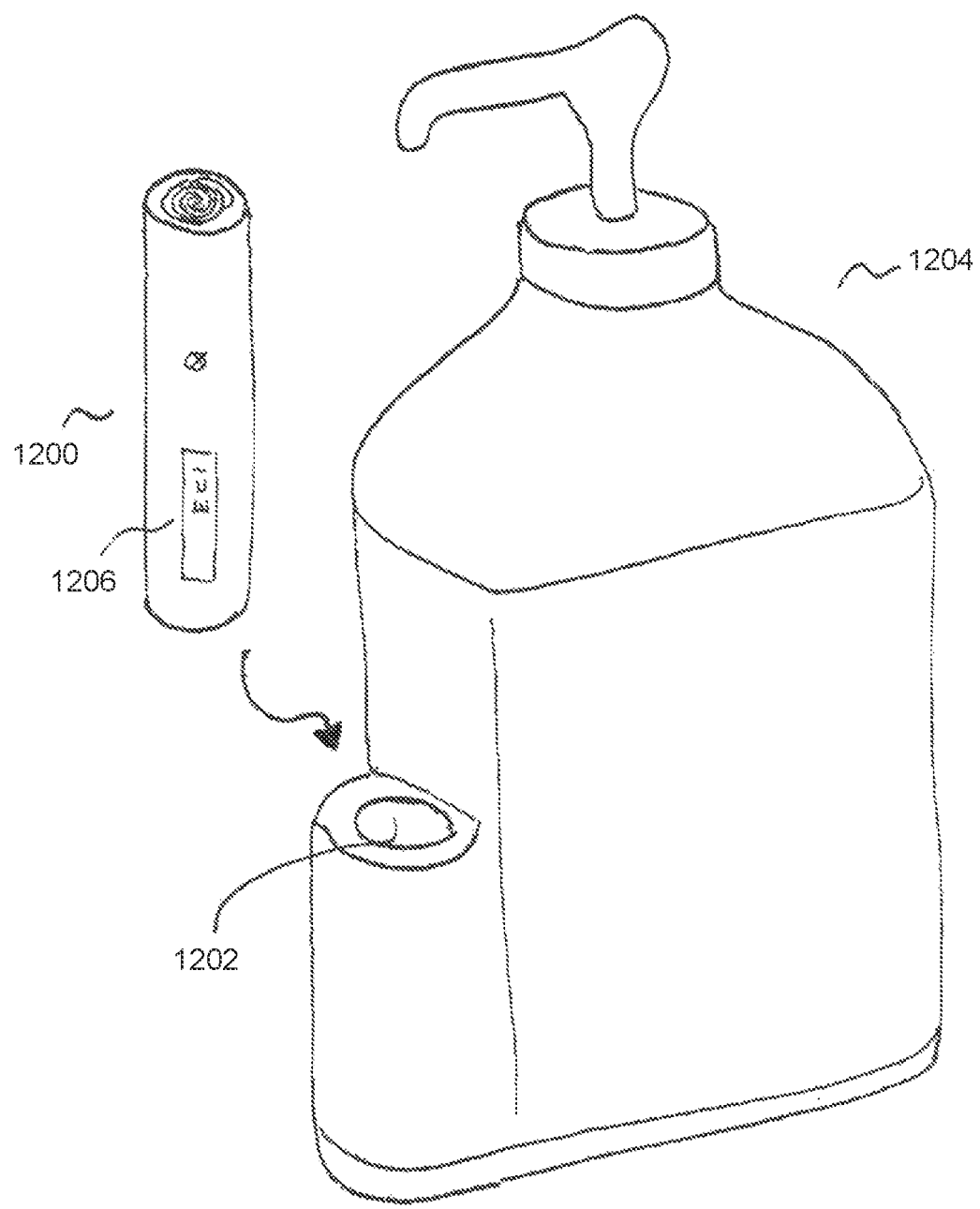
FIGS. 19A-19B show different embodiments of a bottle of lotion with a detachable moisture sensor according to the invention.
Figure 19B:
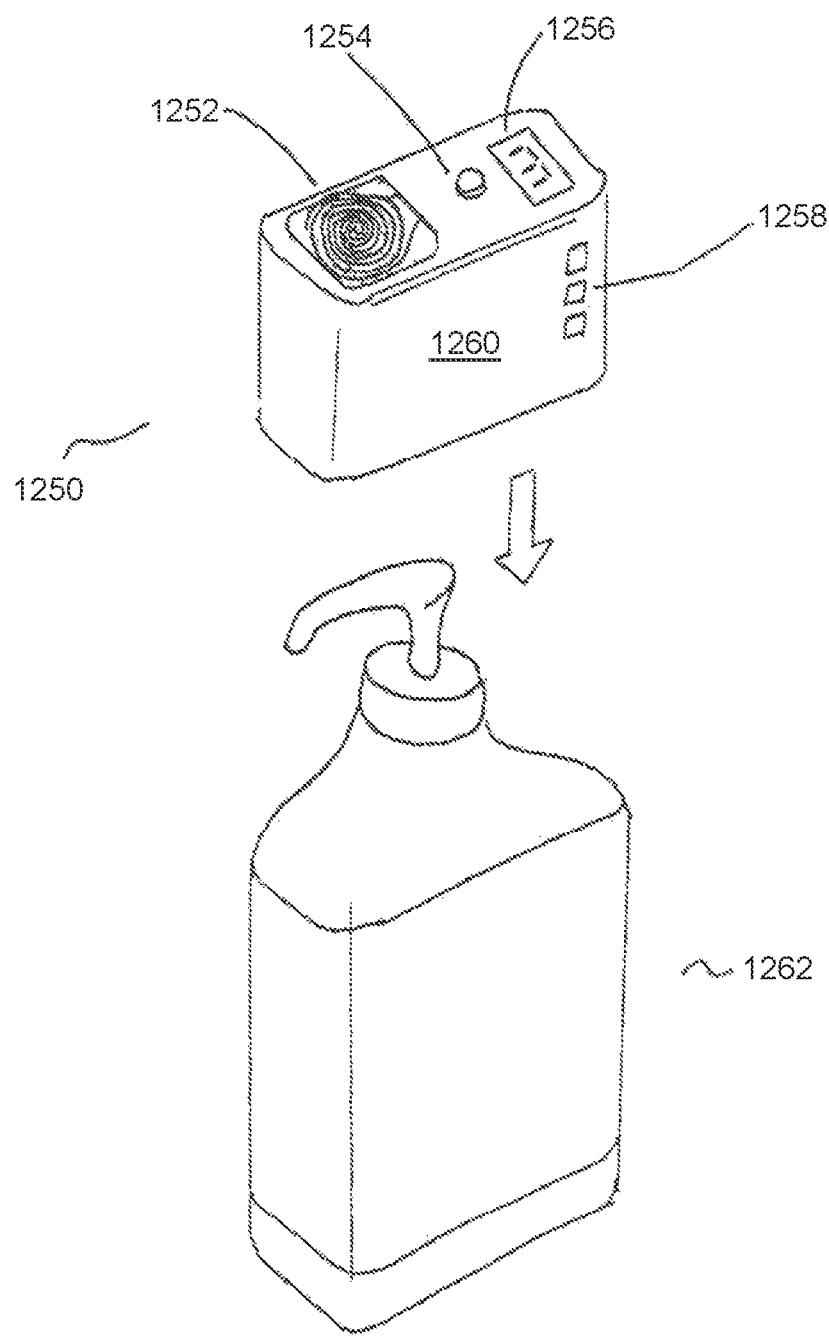

Different embodiments of a sensor that is detachable and attachable are shown in FIGS. 19A and 19B. In FIG. 19A, an attachable sensor 1200 can be in a structure that is in the shape of a tube, such as a cylindrical tube. There can be a slot or a cavity 1202 on the side of the bottle 1204 to receive the tube 1200. The sensor 1200 can be inserted into the slot 1202 when not in use.

FIG. 19B shows another embodiment of a detachable sensor 1250. The sensor 1250 is part of a cap 1260 of the lotion bottle 1262. The sensor 1250 includes a sensor head 1252, an on/off switch 1254, and a display 1256. In this example, the sensor 1250 can also include an electrical input/output port 1258, which will be further described below. Note that the sensor in the embodiment shown in FIG. 19B can also be described as being integrated with the bottle if the cap 1250 is considered to be a part of the bottle. The electrical port 1258 can, in one embodiment, be an electrical connector.

In yet another embodiment, though detachable from the bottle, a moisture sensor is tethered to the bottle. For example, the sensor includes a sensor head that is fabricated on a circular disk. The disk is connected to the bottle through a wire that can be extended from and retractable back into an opening of the bottle. The wire can be rigid or flexible. The sensor head is electrically coupled to at least one electrical component integral with or attached to the bottle through the extendable and retractable wire. In one embodiment, the at least one electrical component can be, for example, a display, an electrical switch, an integrated circuit, a resistor, a capacitor, an inductor, a battery or a speaker.

In the embodiments shown in FIGS. 19A and 19B, the sensor includes a display, such as the sensor 1200 shown in FIG. 19A includes the display 1206. In another embodiment, a detachable sensor includes a sensor head, but does not include an output device, such as a display. For example, the detachable sensor shown in FIG. 19A does not include the display 1206. Instead, there can be one or more electrical components integral with or attached to the bottle, with one of the components being an output device, such as a display. The one or more electrical components integral with or attached to the bottle are electrically coupled to the detachable sensor.

In different embodiments, a detachable sensor can wired or wirelessly communicate with one or more electrical components in a corresponding bottle. In the embodiment that the sensor is tethered to the bottle, the sensor can communicate with the bottle's electrical components by a wired connection through the tether.

In the embodiment that the sensor is not tethered to the bottle, the sensor can communicate with the bottle's electrical components wirelessly. The communication protocol can be based on Bluetooth or Zigbee standards.

In yet another embodiment, for the sensor that is not tethered to the bottle, the sensor electrically communicates with the bottle when the sensor is inserted back into or received by a slot, a receptacle or a housing at the bottle. Data can be temporarily stored at the sensor until the sensor is received by the receptacle at the bottle. Then the data is transferred to the bottle.

In one embodiment, the sensor head includes an application surface, which is the surface configured to touch the skin for measurement. In one embodiment, the application surface of the sensor head is not flat. For example, it can have a curved surface, such as a concave surface. In another embodiment, the application surface of the sensor head conforms to the area where dryness is being measured. In one embodiment, the sensor head is flexible to conform to the shape of the area to be measured. This flexibility could be achieved by the printed circuit board being flexible, such as based on a type of polyimide material known as Kapton®.

In yet another embodiment, a substantially constant force is maintained when the sensor head is applied or pressed onto the surface to be measured. For example, if the sensor includes a printed circuit board inside a housing, the constant-force mechanism can be achieved, such as by placing a soft spring or a piece of foam between the back of the circuit board and the sensor head housing. When the sensor head is pressed onto the surface to be measured, the soft spring or the piece of foam maintains a substantially constant force onto the surface.

Figure 20:
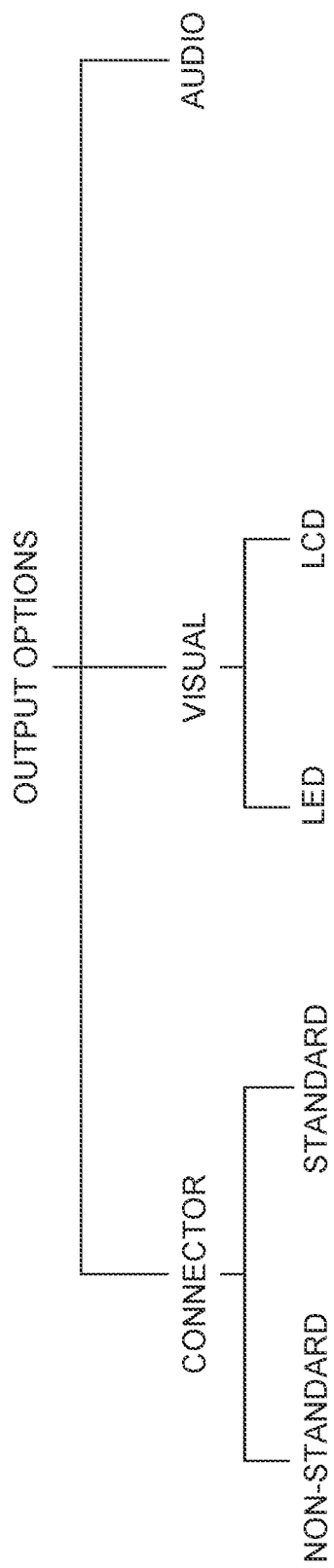
FIG. 20 shows different embodiments of output options from a bottle of lotion with a moisture sensor according to the invention.

FIG. 20 shows different embodiments of output options from a bottle of lotion with a moisture sensor. The electrical components for each of the options can be in a detachable sensor, or integral with or attached to a bottle, or partially in a detachable sensor and partially integral with or attached to a bottle.

Figure 21:
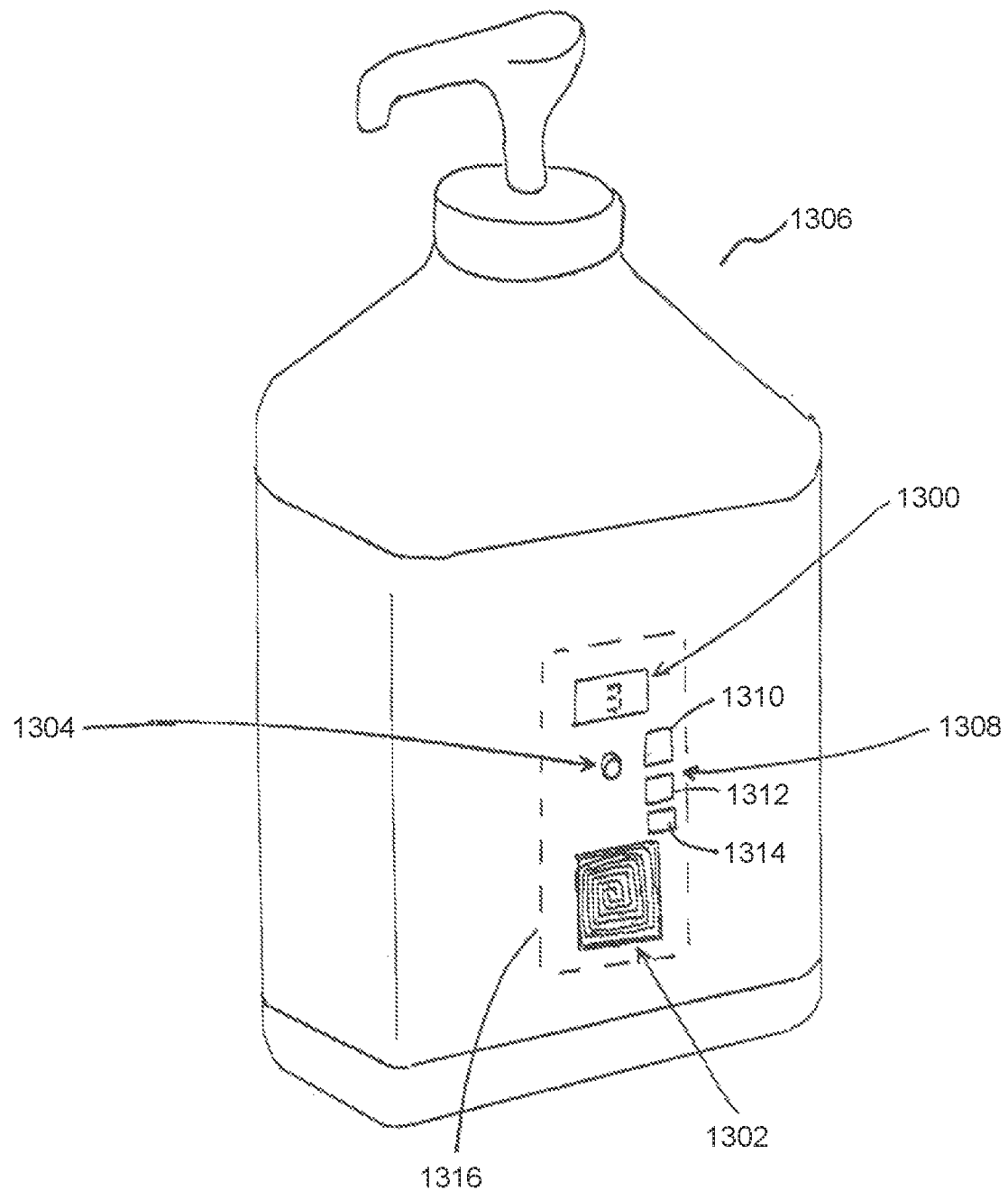
FIG. 21 shows a data output port on a lotion bottle according to one embodiment of the invention.

In one embodiment, the output option includes an electrical connector. The connector can be in the bottle as shown, for example, in FIG. 21. In FIG. 21, the bottle 1306 includes a display 1300, a sensor head 1302 and an on/off switch 1304. In this embodiment, the bottle 1306 also includes an electrical port 1308. The port can be a data port with three conductive pads or dots, 1310, 1312 and 1314, on a circuit board 1316. These three conductive pads could correspond to Tx, Rx and ground, as commonly used in a standard serial data port. One can make connections to electrical components in the bottle through the three pads with a corresponding mating connector, which is not shown in the figure.

In another embodiment, the electrical port is a connector, and the connector is a standard connector, such as a USB connector.

The electrical port can be used to couple an external device to electrical components integral with or attached to the bottle. For example, the electrical port can be used to upload the measured data by a moisture sensor to another device, such as a memory device, like a flash memory card. Then, the memory device can be removed and later attached to another computing instrument to upload the measured data into that instrument.

Instead of at the bottle, in one embodiment, an electrical port is part of a moisture sensor, such as for a standalone moisture sensor that is separate from or not integral with a bottle of lotion.

In another embodiment, an output option is visual, and can be based on LED, LCD, electric ink or thermochromic ink technologies. The output can be a relatively simple indicator. For example, the output can be based on color, such as red, yellow and green. Red can mean that the person's skin is very dry, with green meaning sufficiently moist and yellow being in between. In another example, the output can be either affirmative or negative. For example, the output from a LCD display is a specific type of symbol, such as a bottle with or without a slash. One type of symbol indicates that the user should apply lotion, and the other indicating that the user does not need to apply lotion.

In another embodiment, the visual output can be more elaborate. It can be a message. The message can be a recommendation for the type of lotion to apply based on the measurements. Depending on the dryness of the skin, the recommendation can be changed accordingly based on sensor measurement. For example, a lotion company can have a range of lotions, such as from very creamy (or more oily) to not that creamy (or less oily). The lotion company can designate a number of levels, such as five, for the range, with each level corresponding to a type of lotion along the range of lotions. For example, level 1 will correspond to very creamy lotion. If the sensor measurement indicates that the person's skin is very dry, the dryness would be equated to level 1. Then the recommendation for the user would be to use the very creamy lotion from the company.

To tailor a type of lotion for a person, in one embodiment, a moisture sensor measures the skin of the person for a duration of time, typically in a periodic manner. Based on the measurements, a specific type of lotion is recommended to the person. This recommendation can be provided by a message on the display of the bottle. In another embodiment, the measurements are transmitted to a computer, either through a wired connection or wirelessly. The computer then provides the recommendation. Due to changes in weather, the person might need different types of lotion at different times of the year. In yet another embodiment, the bottle can alert the person to periodically perform the measurements, such as every three months.

In another embodiment, the message on a display can be used to promote products for a company. For example, the products being promoted can be related to skin care.

The time when a promotion is shown on the display can be set by a number of ways. For example, with a bottle having an on/off switch and a display, one can push the switch if one wants to make a measurement. After the measurement, the person can turn the bottle off or it can automatically turn off. In one embodiment, an advertisement or promotion would be shown on the display if the switch is turned off. In another embodiment, the display will show advertisement if the measured results by the sensor have not changed for a predetermined amount of time, such as 30 minutes. In other words, when no one is making any measurements, such as no one pushes the switch on the bottle, the display can show one or more different products from a company. In yet another embodiment, after the measurement, the person can turn off the bottle. Then, after a duration of time, such as 30 minutes, if no one pushes the switch, the bottle will automatically turn on its display to show advertisements.

Alternatively, to manage power consumption, the bottle can display advertisements for a period of time after the bottle is used. For example, the bottle would be considered used if moved or if the start button is pressed. A motion sensor can be integral with or attached to the bottle to detect bottle motion. A motion sensor might also detect motion of a person in the vicinity of the bottle and, in view of such motion, a display on the bottle can be activated (e.g., to display an advertisement).

The advertisement can be from the manufacturer, the wholesaler, the retailer or the distributor of a bottle of lotion. The promotion can be on a product. A product can be a service. The product can be related to skin care, such as lotion.

In one embodiment, the product being promoted can change. This change can be based on time. For example, every week the display can change the product shown, such as the display showing a type of soap on one week and automatically changing to a type of shampoo the next week. The type of soap being promoted can be more suitable for the corresponding skin type as indicated by the lotion, or as indicated by measurements from a moisture sensor.

In one embodiment, the information shown on the display can be modified based on materials transmitted from a company to the bottle. For example, the bottle can also include a connector. When the user uses his computer to visit the website of the company, the user is encouraged to hook up the connector to his computer. The company gives incentives to the user if the user is willing to allow the company to download company information onto the bottle.

To illustrate, for example, the company has a webpage. Through the page, the company tells the user that the user can get a discount for their products if the user allows the company to download information into the lotion bottle. The discount can be on the products that the company is going to download information to the bottle. If the user agrees, the user can select an icon or a button on the webpage. Once the user has selected that button, the webpage will signal the user to connect the bottle to the computer. Then, the webpage will transfer a file to the computer to be downloaded to the bottle. The user can then be allowed to retrieve the discount coupons from the website and can print out the coupons on his printer.

In another embodiment, instead of visual outputs, as shown in FIG. 20, the output option is audio, such as through a speaker. For example, the speaker can provide a beep at a regular interval to remind the user that it is about time to apply lotion or check her skin using the sensor. As another example, the audio output can also provide information about the associated product or related products.

In one embodiment, after the sensor starts measuring, such as when the sensor head is pressed onto a surface, an audio output, such as a beep, provides an indication that the measurement is done. This could be achieved when the output from the sensor does not fluctuate beyond a certain threshold, such as when the change in percentage from an output to its immediate next output is below a preset amount. In another embodiment, if the sensor determines that the user's skin is a bit too dry or the user needs lotion, the sensor would produce an audio output, which could be a pre-stored message, such as, "You need lotion."

In another embodiment, the sensor starts measuring when the sensor head is pressed onto a surface. This can be done, for example, by having a pressure sensor or a switch at the sensor head. The pressure sensor or switch gets activated when pressed. The moisture sensor then continues to measure for a preset amount of time, such as 1.5 seconds. After the preset amount of time, the moisture sensor stops measuring. In one approach, the largest value (e.g. capacitance value) measured during the preset amount of time is chosen to be the measured value.

Instead of using a pressure sensor, other mechanisms can be used to automatically activate the moisture sensor. For example, there can be a switch with a spring. When the force exerted on the spring exceeds a certain amount, such as 4 ounces, the switch would turn on and the moisture sensor would take a measurement. In another embodiment, the moisture sensor includes a motion detector. If the motion detector senses motion, the moisture sensor would be automatically activated to take measurements for a preset amount of time.

A number of embodiments have been described where a moisture sensor is integral with or attached to a bottle. In one embodiment, the moisture sensor is a stand-alone sensor. It can be handheld or portable, and can be sold or acquired apart or separately from the bottle. Different electrical features/capabilities described above regarding a bottle can also be implemented into the handheld or portable moisture sensor according to different embodiments.

Figure 22A:
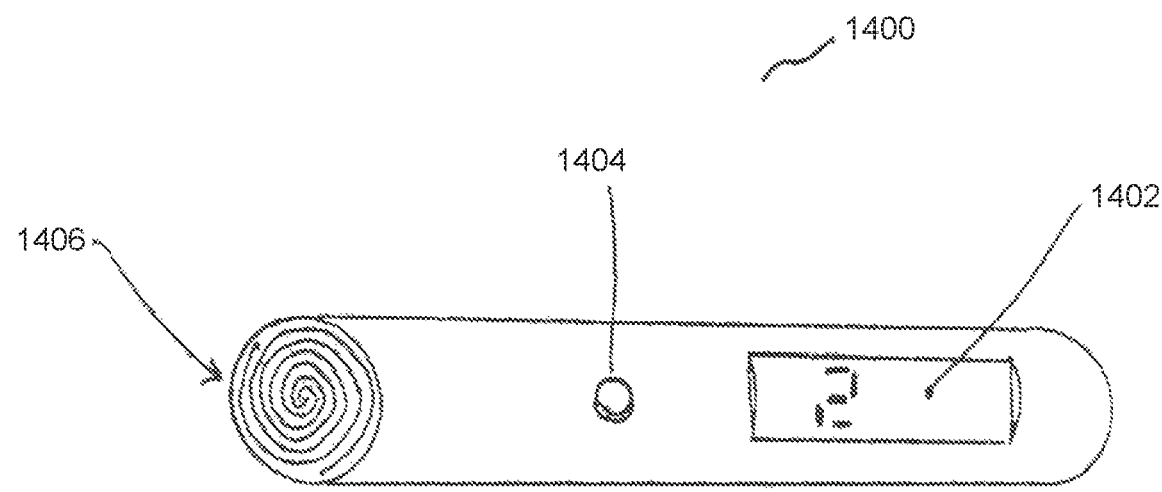
FIG. 22A shows a moisture sensor according to one embodiment of the invention.

FIG. 22A is a perspective view of a moisture sensor 1400 according to one embodiment of the invention. The general configuration of the sensor is cylindrical. The sensor 1400 also includes a display or screen 1402, an on/off switch 1404, and a sensor head 1406. In one embodiment, the sensor head 1406 includes an application surface. The application surface can include two conducting lines adjacent to each other, with the conducting lines covered by a thin insulating film. In FIG. 22A, the display can be a flat display located in a recessed and flat surface. In another embodiment, the display can be a flexible display, such as an electrophoretic display. In yet another embodiment, the general configuration of the sensor is rectangular, or the sensor has a rectangular cross section. In the embodiment shown in FIG. 22A, the application surface can be substantially perpendicular to the display 1402. In one embodiment, the sensor head is on a printed circuit board, which is electrically coupled to one or more other printed circuit boards in the sensor. In another embodiment, the sensor just has one printed circuit board and it is a flexible printed circuit board. In the embodiment shown in FIG. 22A, the flexible board can be bent so that a portion of it is for the sensor head, and another portion is for other electrical components, such as for coupling to the display 1402.

Figures 22B, 22C:
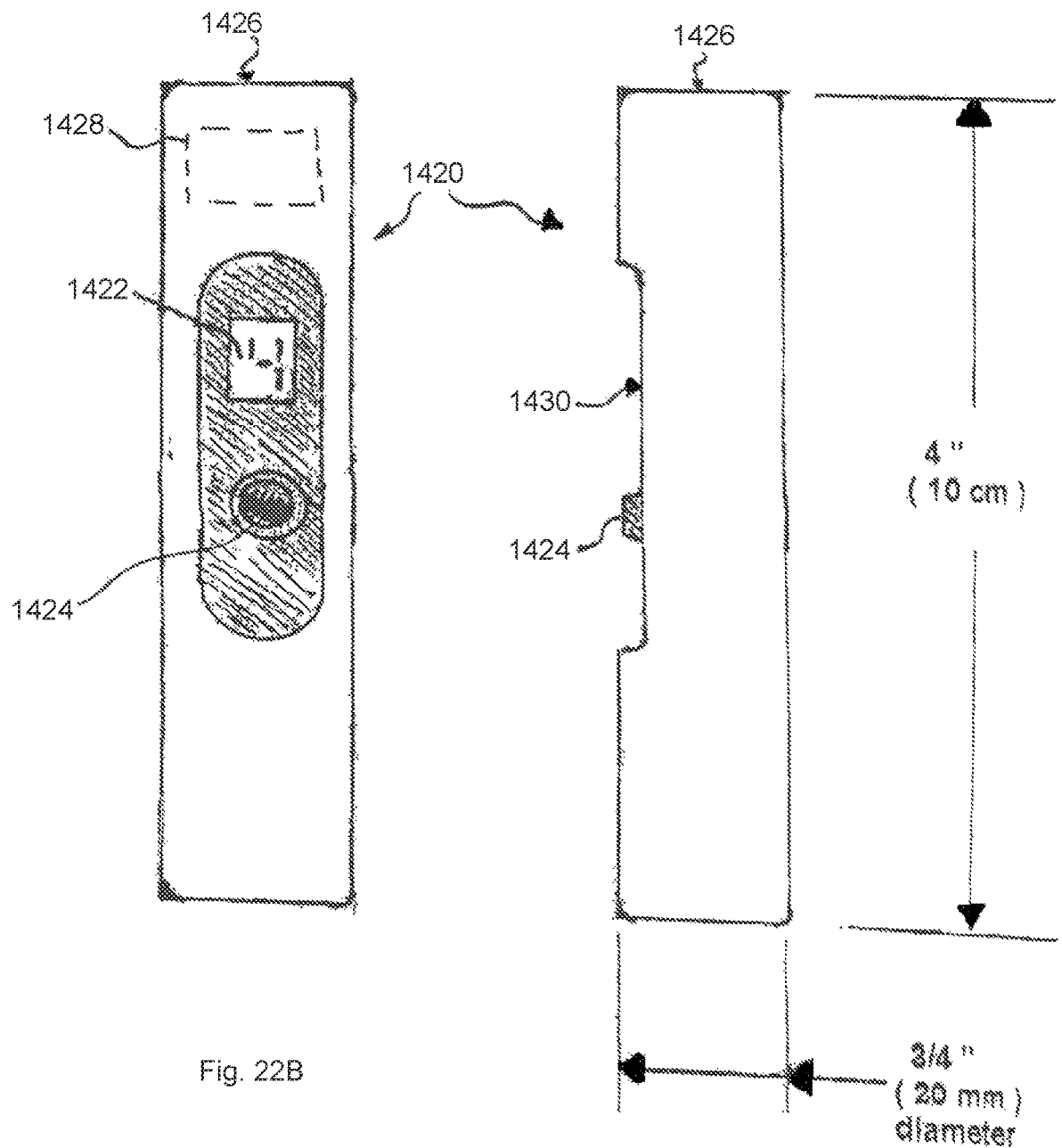
FIGS. 22B and 22C are front and side view for a moisture sensor according to another embodiment of the invention.

FIGS. 22B and 22C are front and side views for a moisture sensor 1420 according to another embodiment of the invention. The sensor 1420 also includes a display or screen 1422, an on/off switch 1424, and a sensor head 1426. In this embodiment, the sensor head 1426 resides at one end of the sensor 1420, which is generally cylindrical. In one embodiment, the sensor head 1406 includes an application surface which can include two conducting lines adjacent to each other and covered by a thin insulating film. The sensor 1420 can also include promotional area 1428 on the surface of a housing for the sensor 1420. As an example, the promotional area 1428 can carry a business logo, a trademark, or advertisement for a product or service. Although the general configuration of the sensor 1420 is cylindrical, the sensor 1420 can include a recessed, flattened surface 1430. In this example, the display or screen 1422 and the button 1424 are provided at the recessed, flattened surface 1430. FIG. 22C also depicts representative dimensions of the housing for the sensor 1420 according to one embodiment.

Figures 22D, 22E:
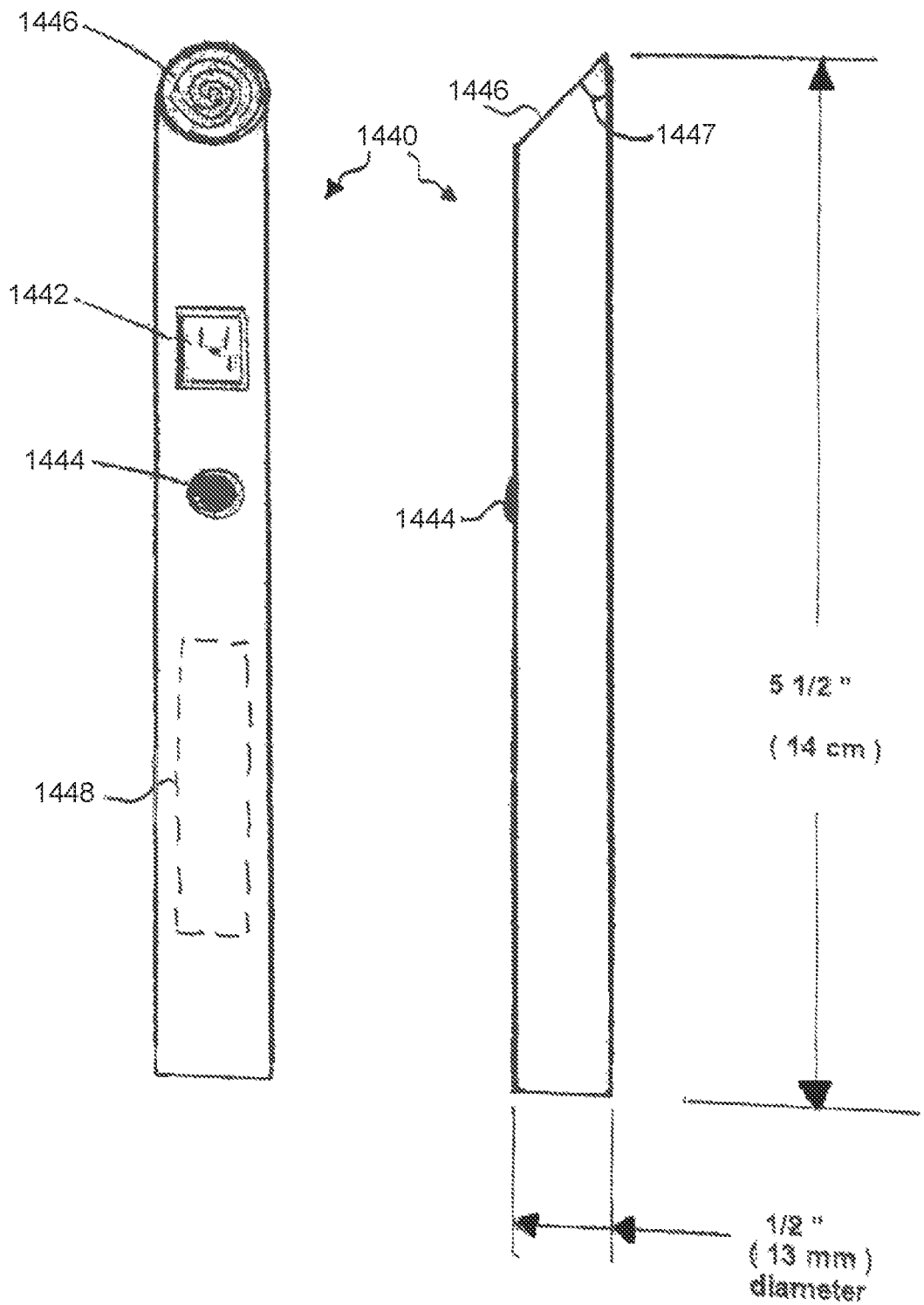
FIGS. 22D and 22E are front and side view for a moisture sensor according to still another embodiment of the invention.

FIGS. 22D and 22E are front and side views for a moisture sensor 1440 according to still another embodiment of the invention. The sensor 1440 also includes a display or screen 1442, an on/off switch 1444, and a sensor head 1446. In this embodiment, the sensor head 1446 resides at one end of the sensor 1440, which is generally cylindrical. As shown in FIG. 22E, the sensor head 1446 is angled, such that the angle 1447 is an acute angle. In one embodiment, the sensor head 1446 includes an application surface which can include two conducting lines adjacent to each other and covered by a thin insulating film. The sensor 1440 can also include one or more promotional areas 1448 on the surface of a housing for the sensor 1440. As an example, the promotional area 1448 can carry a business logo, a trademark, or advertisement regarding a product or service. FIG. 22E also depicts representative dimensions of the housing for the sensor 1440 according to one embodiment.

FIGS. 22F, 22G and 22H are rear, side and front view for a moisture sensor 1460 according to still another embodiment of the invention. The sensor 1460 also includes a display or screen 1462, an on/off switch 1464, and a sensor head 1466. In this embodiment, the sensor head 1466 is placed near one end of the sensor 1460, which is generally rectangular with rounded edges. In one embodiment, the sensor head 1466 includes an application surface which can include two conducting lines adjacent to each other and covered by a thin insulating film. The sensor 1460 can also include one or more promotional areas 1468 on the surface of a housing for the sensor 1460. As an example, the promotional area(s) 1468 can carry a business logo, a trademark, or advertisement for a product or service. The sensor 1460 can include a recessed, flattened surface 1470 where the sensor head 1466 is located. FIGS. 22F, 22G and 22H also depict representative dimensions of the housing for the sensor 1460 according to one embodiment.

In another embodiment, the sensor 1460 can be in the shape of a nail file, with a front surface and a back surface. The application surface of the sensor head can be on the front surface, at one end of the filer, while the on/off switch with the display are on the back surface. Optionally, the sensor 1460 can also actually provide a nail file surface so as to serve as a nail file.

In one embodiment, the sensor includes a mechanism to allow at least one of its electrical components to be connected to an electrical component outside the sensor. For example, the sensor includes a connector, which could be a standard connector, to allow the measurements made by the sensor to be captured and analyzed by another computing device. In another example, the sensor includes a wireless transceiver to allow, for example, measurements made by the sensor to be wirelessly transmitted to another device and to be displayed by the another device. The another device could be a portable device also carried by the user and the portable device has a display. The wireless technologies could be based on Bluetooth, WiFi or other standards.

The sensor can be incorporated into other devices. For example, the moisture sensor is incorporated into a pen, a phone, a key chain or a pair of glasses. To illustrate, the sensor is incorporated into a pen. As one writes, the pen can automatically measure the dryness of the person's skin. Similarly, the sensor can be in a phone. As one makes a phone call, the sensor can measure the dryness of the person's skin touching the sensor head on the phone.

In another embodiment, the sensor can be incorporated into a holder in the configuration of a lipstick or chapstick. For example, the sensor head is on the top surface of one end (e.g., on a base end or a cap end) of a product similar to a lipstick. There is also a display or a beeper on the lipstick. In one embodiment, based on measurements by the sensor, if a person's skin is too dry, the person can remove the cap, and apply the moisturizing materials inside, such as by rotating the bottom portion of the holder, as in a lipstick.

In one embodiment, a moisture sensor is personalized to a user, depending on the skin type of the user. Depending on whether the skin type of the user is dry/medium/moist, the user can adjust the sensor accordingly, or can acquire different types of sensors. For example, with the skin type selected, the full range of the output would be for that specific skin type. If the output is in scales of 1 through 5, the entire range would be applicable for the skin type selected. One way to select skin type is that the selection is configured to be done by the user. There can be a skin-type switch on the sensor. The general idea is to set the proper scale of the output of the sensor based on the position of the switch, which could be adjusted by the user. In another embodiment, the selection is configured not to be done by the user. There can be a jumper switch on a printed circuit inside the sensor. The manufacturer could set the switch position for different skin-type sensors.

Figure 23:
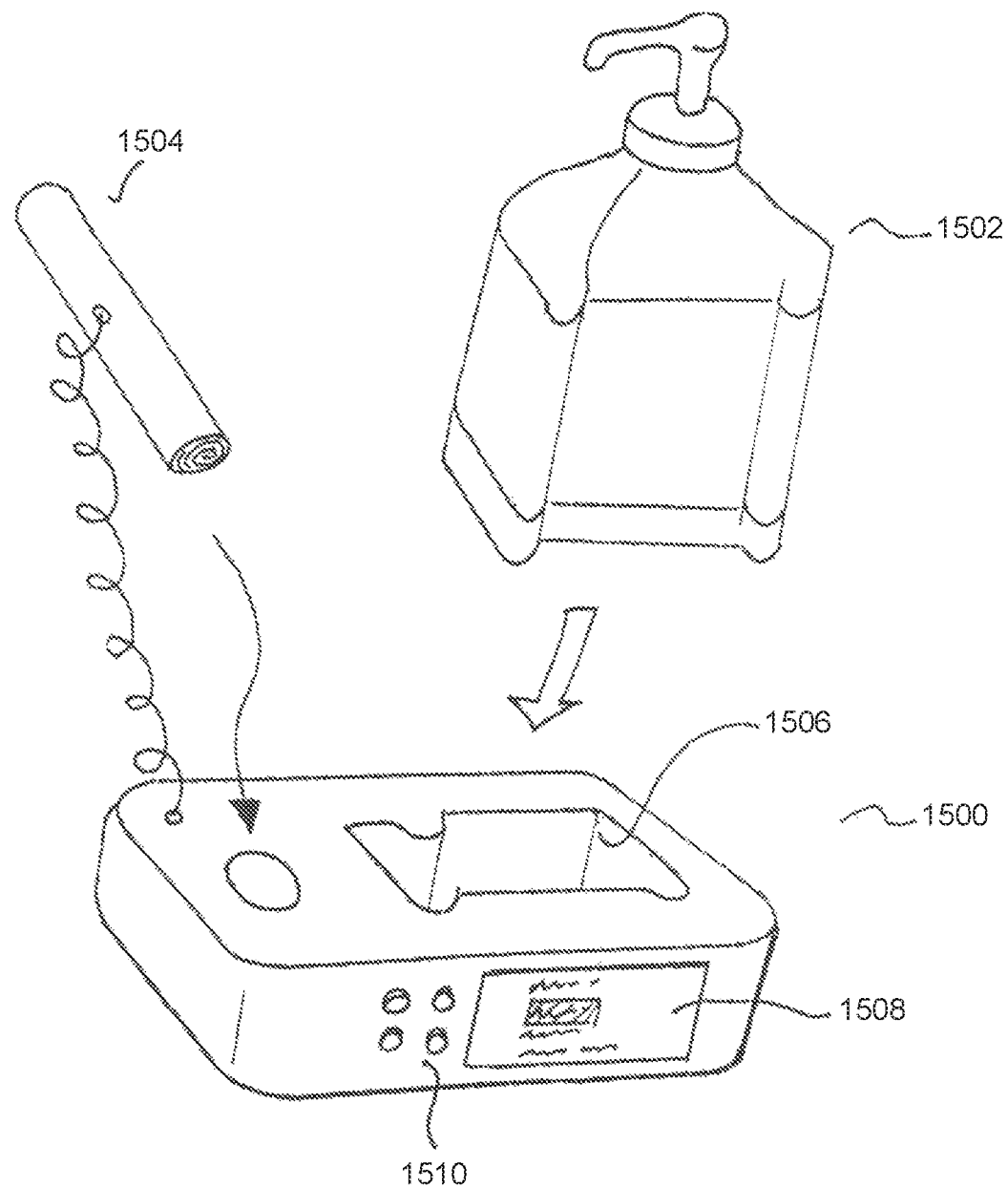
FIG. 23 shows a base for a bottle of lotion and a moisture sensor according to one embodiment of the invention.

In one embodiment, a moisture sensor and any other electrical components in the bottle are in a base that has at least one slot, opening, cavity or receptacle. FIG. 23 shows an embodiment of such a lotion base 1500 with a bottle of lotion 1502 and a moisture sensor 1504 tethered to the base. The base 1500 includes a cavity 1506 for the bottle of lotion 1502 to snugly fit into. The base can act like a base-station or a docking station.

In one embodiment, the base 1500 includes a display 1508, and a number of input switches 1510, with one of them being an on/off switch. Other switches can be used for additional input mechanisms to be further described below.

In one embodiment, different brands of lotion can have its base of specific design. For example, L'OREAL® can have an L-shape base. In another example, the cavity for the lotion bottle is of a specific dimension to fit the dimension of the corresponding lotion bottles. Each brand or the lotion bottles from each company can have its own dimensions. If one is using the base from company A, the person would have to buy lotions from company A to fit into the base.

In one embodiment, there can be a standard electrical connector at the base, such as a USB connector. The connector can be used as an input/output port.

In another embodiment, when the amount of lotion in the bottle is low, the base would generate a signal. For example, the base 1500 shown in FIG. 23 can include a scale that keeps track of the weight of the lotion bottle 1502. As the weight goes below a certain value, a signal will be generated. The signal can be a visual signal, such as on the display 1508. The signal can be audio, such as a beeping sound that is periodically produced if the weight is below the threshold. The beeping sound can be turned off, such as through one of the switches 1510 shown in FIG. 23.

In yet another embodiment, the low-lotion signal is transmitted to a computer that is connected to the Internet. This can be done through a wire or a wireless connection. For example, the base can be connected to the computer through a connector at the base. In another embodiment, the base is connected to the computer wirelessly, such as to a wireless hub in its vicinity. The wireless hub, for example, can be a WiFi hub. The computer can also be wirelessly connected to the hub.

When the low-lotion signal is generated, that signal can be transmitted to the computer. Next time, when the user gets onto the computer, the user is informed that a message has arrived from his lotion bottle. After reading the message, the user is asked if he wants to send the message to a company, which can be the company selling him the lotion. Alternatively, a message regarding the low-lotion signal can be automatically sent to the company without requiring or soliciting permission from the user. The message can also ask the user if he wants the company to contact him regarding refills. If the person responds affirmatively, the person can be asked to enter his email address, and the corresponding information will be transmitted to the company.

The transmission of the messages to the company can be through the Internet. This would allow the company to become aware of the lotion usage by the person. If the person agrees to receive information from the company, such as on refills, the company can send the person a message, such as through email, asking the person if he wants a similar bottle of lotion directly sent to him. If the person answers yes, the company will mail a bottle to him, and can charge him, such as through his charge cards. In another embodiment, the person is subscribed to an automatic-lotion-refill service. Based on the service, when the company receives the low-lotion signal, the company would send the person another bottle of lotion and charges the person's credit card accordingly.

In one embodiment, a bottle of lotion can have more than one sensor. Additional sensor(s) can be used to sense one or more other parameter(s). The one or more other parameters can be related to the user of the lotion or the environment the user is in. For example, in one embodiment, a lotion bottle is for suntan lotion. The bottle includes an indicator that alerts the user to apply the lotion. The indicator can be based on dryness or moisture content of the skin. Dry skin or low moisture content can indicate the need for suntan lotion. Moderate-to-high moisture content can indicate the presence of adequate quantities of suntan lotion. In one embodiment, the moisture sensor is applied to the user before the user gets into the water. One additional sensor that can be used with the bottle is a sun sensor. The sun sensor measures radiation (e.g., light) intensity. In one embodiment, the radiation intensity can pertain to UV radiation. For example, when the measured intensity (currently or cumulatively) is beyond a certain level, the user can be alerted to apply lotion (i.e., suntan lotion), or to apply more lotion to provide the user with additional protection.

In another example, one additional sensor is a humidity sensor that provides indication as to the humidity level of the environment. In this example, recommendation to the user regarding application of lotion depends on both the user's moisture level and the humidity level of the user's environment. The lotion bottle could alert the user to apply more lotion if both the environment is dry and the user's skin is dry. In another example, if the user's skin is moist, but the environment is dry, the bottle would still recommend the user to apply lotion. Different examples of commercially available humidity sensor are applicable, such as those in packaging applicable to printed circuit board assembly process. An example of such a packaging is surface mount packages.

The one or more additional sensors can be integrated together, or integral with a lotion bottle, or a lotion base. In another embodiment, the one or more additional sensors are attached to, or integral with a moisture sensor, which is not electrically coupled to a lotion bottle, or a lotion base.

In yet another embodiment, information from one or more additional sensors is remotely measured, and then transmitted to be used with measurements from a moisture sensor. For example, a bottle of lotion is wirelessly linked to a computer, which is connected to the Internet. Through the Internet, the computer receives information regarding the general humidity level of the town the user is at. The computer passes such humidity level data to the bottle. Based on such humidity level information and measurements from a moisture sensor, the bottle provides recommendation to the user regarding lotion usage.

A number of embodiments have been described where the lotion is contained in a bottle. In one embodiment, a bottle is defined as a container or a receptacle that has a narrow neck. In another embodiment, a bottle is defined as a container or a receptacle with a width that is not uniform (some part narrower than another part, such a neck portion being narrower).

In another embodiment, a bottle does not have to have a narrow neck and a bottle can have uniform width or substantially uniform width, but the bottle has an opening or a mouth that can be plugged, corked or capped.

In yet another embodiment, lotion was bought through an online store. The online store or web-store can keep track of the fact that a user bought a specific type of lotion. Next time, when the user visits the web-store, the user can be notified of information related to similar lotion or similar skin care product. For example, if the store has a similar type of lotion that is on sale, the store can let the user know.

Different embodiments described are applicable to human beings. In one embodiment, the lotion bottle and/or the moisture sensor and/or the lotion base is applicable to animals.

A number of embodiments have been described regarding a lotion bottle and a moisture sensor. In one embodiment, instead of a bottle, different aspects described in this application are also applicable to other types of containers, such as a box. One example of such a container is a tube. The tube can be squeezed to bring out the substance the tube carries. The container can have a sensor that is integral with, or attachable to and detachable from, the container. The sensor can be configured to measure an attribute of a living being with the container containing a substance that affects the attribute. The sensor and the container together as a unit can be portable.

The discussion above often refers to lotion, or more generally skin care products, for skin. Another embodiment of the invention pertains to hair care products for one's scalp. In one embodiment, the scalp can be considered skin on a person's head, and the hair care products can be considered skin care products. A sensor can measure an attribute of the scalp to determine if hair care products are needed, such as the type of shampoo. For example, a moisture sensor could measure the dryness of the scalp of the user. A scalp with a lot of dandruff has little moisture, and can benefit from specific shampoo for people with a lot of dandruff. Hence, the moisture sensor measurements can identify a specific hair care product or a class of hair care products, such as a type of shampoo.

Figure 24:
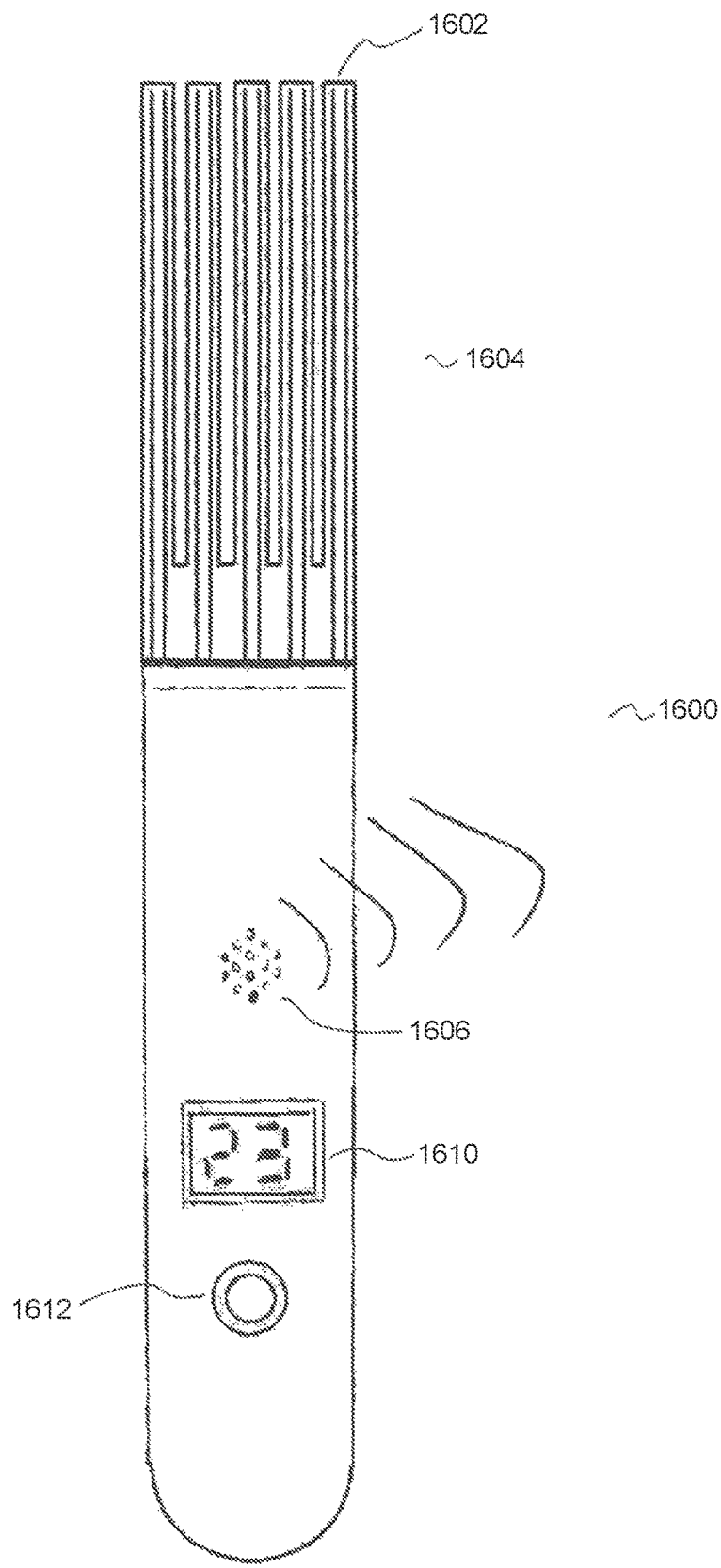
FIG. 24 shows one embodiment of a moisture sensor for measuring the scalp according to the invention.

FIG. 24 shows one embodiment of a moisture sensor 1600 for the scalp. The sensor head 1604 includes a number of narrow strips, probes or fingers 1602. In this example, the sensor also could include a speaker 1606, a display 1610 and a switch 1612. The speaker 1606 could provide indications as to when measurements are done. The display 1610 could display the measurements, while the switch 1612 could be an on/off switch. Each finger has at least two conducting lines closely-spaced adjacent to each other, with the lines covered by a thin piece of insulating material, for capacitance measurement. As an example, each line can be 7 mils wide and the spacing between lines can be also 7 mils or other dimensions. In FIG. 24, only two conducting lines are shown in each finger. The lines as shown serve as illustrations. In different embodiments, there could be a number of lines adjacent to each other similar, for example, to those shown in FIG. 16C. In one embodiment, the width of each strip or finger is about 0.05", with about 0.05" spacing between strips. The narrow fingers improve the ease of having the sensor head touch the scalp when the scalp is covered by a layer of hair. For example, the narrow fingers allow placing the sensor strips directly against the scalp, in between and under the hairs.

Figure 25:
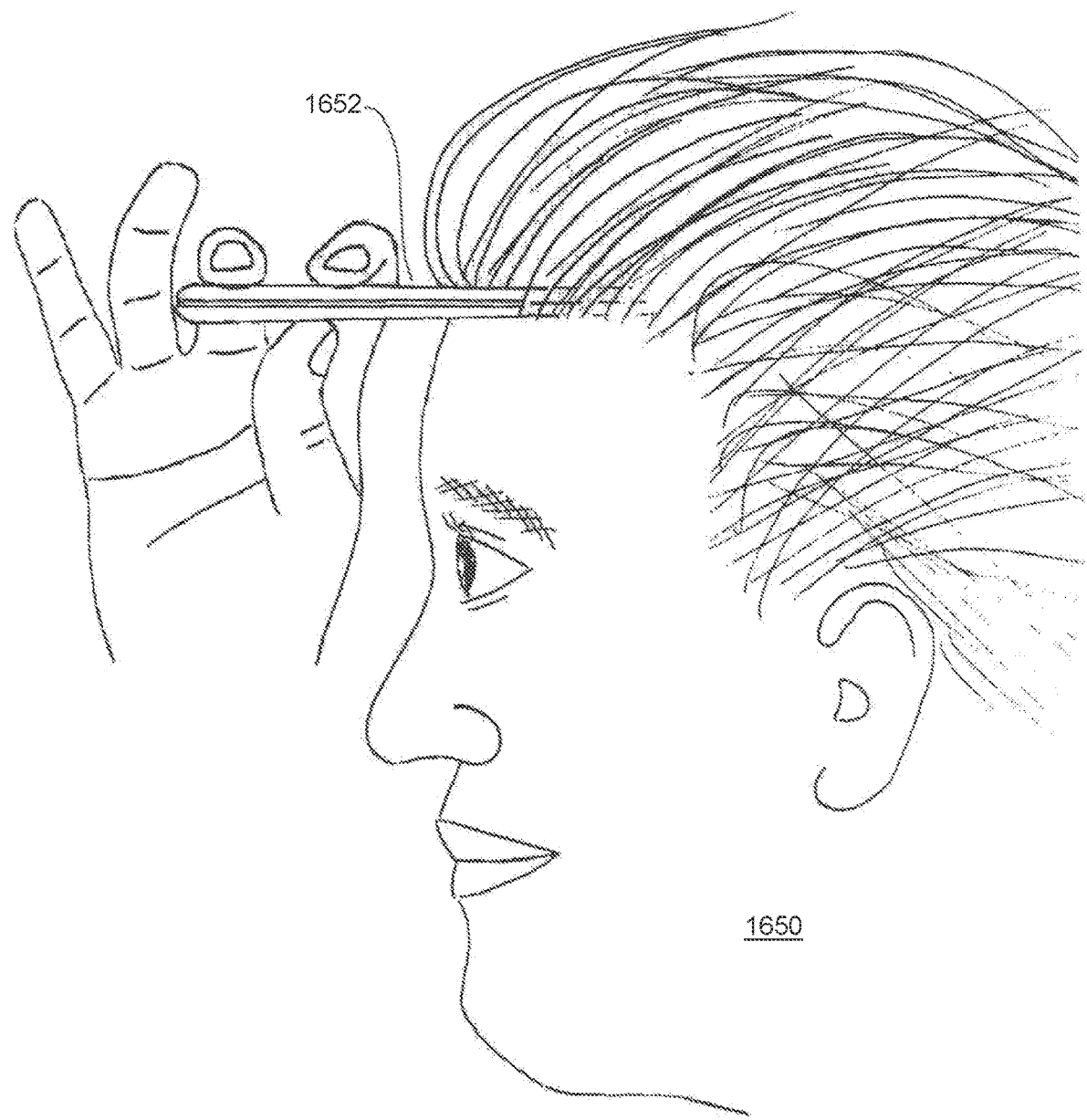
FIG. 25 shows an example of a user using a moisture sensor for the scalp according to the invention.

FIG. 25 shows an example of a user 1650 using a moisture sensor for the scalp 1652, such as the one shown in FIG. 24. The user 1650 places the strips into the hair, and presses them onto his scalp. Then the user activates the on/off switch to start measuring. When the measurement is done, the sensor 1652 produces an audible signal to alert the user.

The multiple fingers increase the intensity level and accuracy of the measured signals. In the example shown in FIG. 24, capacitances measured by each pair of conducting lines are added in parallel to increase the signal level.

In one embodiment, the multiple narrow fingers are in the shape of a comb, and circuits on all of the strips could be on the same printed circuit board. As an example, there are sixteen fingers per inch, each finger being about 0.03125" wide, with about 0.03125" spacing between each pair of fingers.

A number of embodiments have been described regarding a moisture sensor that includes at least two conducting lines adjacent to each other, with the lines covered by a thin piece of insulating material, for capacitance measurement. In another embodiment, the moisture sensing mechanism is based on Raman spectroscopy using infrared technologies. For example, the sensor head includes a near-infrared emitter and a near-infrared detector. With the sensor head applied to an area of skin, a portion of the emitted infrared radiation is reflected by the skin and absorbed by the detector. The detector includes a filter to measure specific spectral frequency bands. Based on the intensity measured, the sensor head determines the amount of moisture level in the area of skin. In one embodiment, such a sensor is used to measure the moisture level of the scalp of a person. Since the emitter and detector could occupy a relatively small area, the sensor head could be relatively small. In one embodiment, there are more than one probe or fingers as in FIG. 24, with an emitter/detector pair on each finger. Multiple pairs provide redundancy in the output data and could improve measurement accuracy.

In another embodiment, a moisture sensor head includes both conducting lines adjacent to each other for capacitance measurements, and one or more near-infrared emitter/detector pair for infrared measurements. In one embodiment, the two types of moisture sensors focus on measuring moisture level at different layers of the skin below the skin surface.

A number of embodiments of the invention pertain to a medical monitoring system. The medical monitoring system facilitates end-users in obtaining medical information concerning their health or wellness. In one embodiment, an end-user is provided with a medical monitoring appliance. In another embodiment, an end-user acquires an appropriate medical monitoring appliance. The end-user can utilize the medical monitoring appliance to capture health data concerning the end-user. The health data can be electronically stored at a central repository and be available for electronic access by medical personnel and/or the end-user. The invention also facilitates remote evaluation of an end-user's health data by another person, such as a medical specialist.

A number of embodiments of the invention are discussed below with reference to FIGS. 26-36. However, those skilled in the art will readily appreciate that the detailed description given herein with respect to these figures is for explanatory purposes as the invention extends beyond these limited embodiments.

Figure 26:
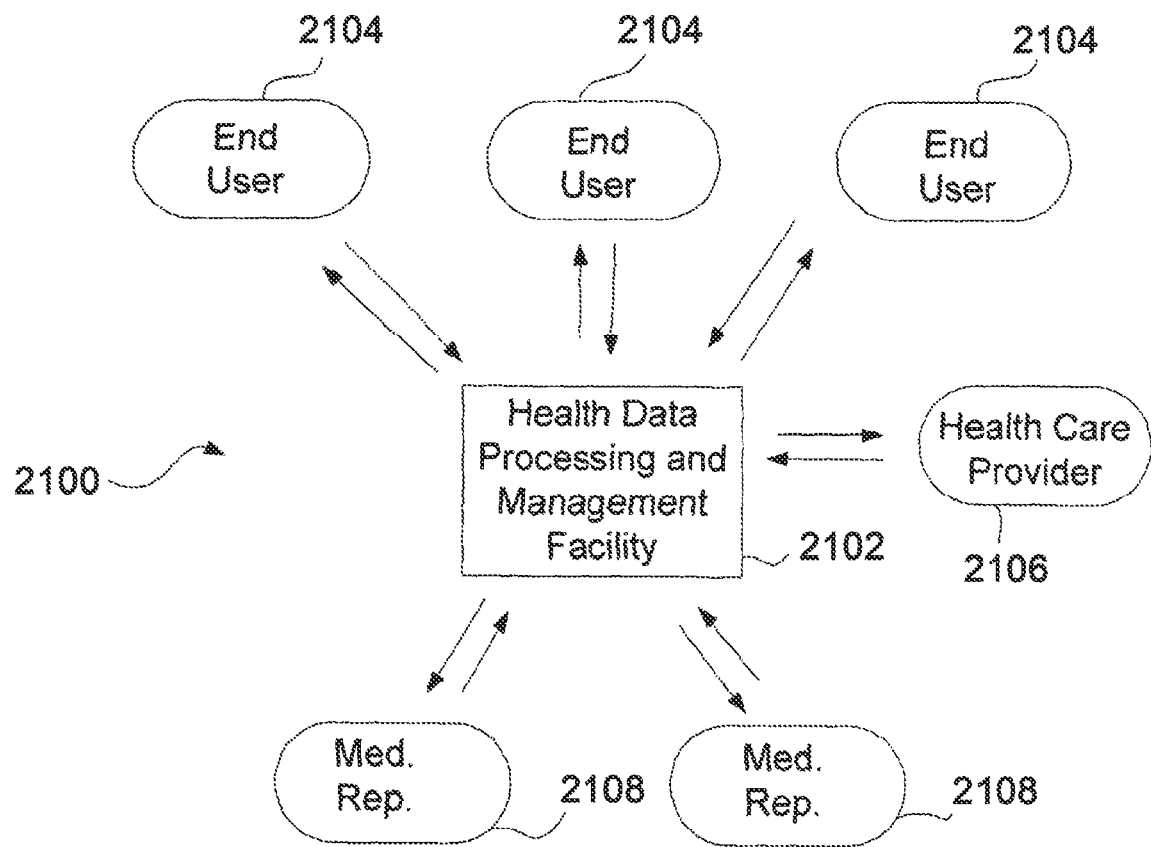
FIG. 26 is a distributed health and wellness system according to one embodiment of the invention.

FIG. 26 is a distributed health and wellness system 2100 according to one embodiment of the invention. The health and wellness system 2100 is distributed in that it utilizes resources, which can be both personnel and electrical equipment, located in one or more different locations.

In one embodiment, the distributed health and wellness system 2100 includes a health and data processing and management facility 2102. The health data processing and management facility 2102 controls the overall operation of the distributed health and wellness system 2100. In particular, the health data processing and management facility 2102 is able to interact with a plurality of end-users 2104. An end-user 2104 is a person whose health or wellness is being monitored by the distributed health and wellness system 2100. Through interaction with the end-users 2104, the health data processing and management facility 2102 operates to acquire health and wellness data (hereafter "health data") from the end-users 2104. The acquired health data can be stored and managed by the health data processing and management facility 2102. In addition, health-care providers 2106 can be permitted to access the health data processing and management facility 2102. Hence, the health data processing and management facility 2102 facilitates the health care providers 2106 in gaining access to the health data stored and maintained by the health data processing and management facility 2102. Moreover, medical representatives 2108 can interact with the health data processing and management facility 2102. The medical representatives 2108 can be trained medical professionals, nurses, medical technicians, etc. The medical representatives 2108 can also gain access to the health data stored and maintained by the health data processing and management facility 2102. The medical representatives 2108 can be associated with, or independent of, the health-care providers 2106.

According to one aspect of the invention, the distributed health and wellness system 2100 is distributed. For example, the end-users 2104 participate in the acquisition of their health data. The acquired health data is then transmitted from an end-user's location (e.g., home, office or local clinic) to the health data processing and management facility 2102, which serves as a central processing facility. The health care providers 2106 need not be located at the health data processing and management facility 2102. Instead, the health care providers 2106 can be provided with electronic access to the health data stored and/or maintained at the health data processing and management facility 2102. Likewise, the medical representatives 2108 can be geographically located away from the end-users, such as at other parts of the world. However, the medical representatives 2108 can gain access to the health data stored and maintained by the health data processing and management facility 2102.

In one embodiment, the medical representatives 2108 are utilized to analyze the health data that is stored and maintained by the health data processing and management facility 2102. In this regard, a particular medical representative 2108 can specialize in evaluating health data for particular problematic health conditions. With electronic access to the health data and assistance from the health data processing and management facility 2102, a particular medical representative 2108 is able to efficiently handle and/or analyze health data regarding specific problematic health conditions for a number, which can be a large number, of end-users 2104. For example, the particular medical representative 2108 may be highly trained at reviewing images of skin discolorations to evaluate presence of skin cancer conditions. In this regard, as an example, the health data processing and management facility 2102 can facilitate end-users 2104 in acquiring images of suspect skin regions on their bodies. The skin images that have been acquired from the end-user 2104 can then be sent (electronically or manually) to the health data processing and management facility 2102 and then stored by the health data processing and management facility 2102. When or as appropriate, the medical representative 2108 can examine the stored skin images to analyze whether a problematic skin condition exists, such as melanoma or skin cancer. Further, if there is a suspected problematic skin condition, the medical representative 2108 can request (or the health data processing and management facility 2102 can determine) that an appropriate health care provider 2106 should be notified concerning the suspected problematic skin condition. The health data processing and management facility 2102 can operate to so inform the health care provider 2106. As appropriate, the health data processing and management facility 2102 may also operate to inform the end-user 2104 of the suspected problematic skin condition.

Given that the particular medical representative 2108 can be specialized and can be located anywhere electronic network (e.g., Internet) access is available, the cost of the analysis can be reduced. As an example, the particular medical representative 2108 can be a doctor, such as a doctor experienced in analyzing skin conditions. The doctor, referred to as a primary doctor, can be assisted by a team of junior doctors and other medical practitioners. The initial review of the health data can be by the lower cost medical practitioners. If desired, multiple independent reviews of the same health data can be performed for even greater certainty. Subsequent review by the junior doctors can then be performed on a subset of the health data that potentially have suspected problematic skin conditions, and then still a further subset of the health data can be reviewed by the primary doctor. The health data can also be reviewed by a computer. The computer evaluation can be initially performed as to assist or aid practitioners in reviewing the health data or can be performed as requested by a practitioner, health care provider or user. The computer evaluation can also be automatically performed, such as periodically or when new health data is available to be evaluated. Still further, the computer evaluation can serve to trigger manual evaluation or review of the health data by practitioners or health care providers.

The skin images acquired and processed, for example, as noted above, are typically optical images. Such optical images can, for example, be referred to as digital pictures. However, it should be noted that the skin images can differ in other embodiments. For example, in one embodiment, the skin images can pertain to thermal images. The thermal images can be acquired and processed to analyze whether a problematic skin condition exists. As an example, it is believed that cancerous cells tend to absorb or retain more heat, or take longer time to release heat absorbed, than healthy or non-cancerous cells. The thermal images can be processed to locate skin regions having such problematic conditions.

Figure 27:
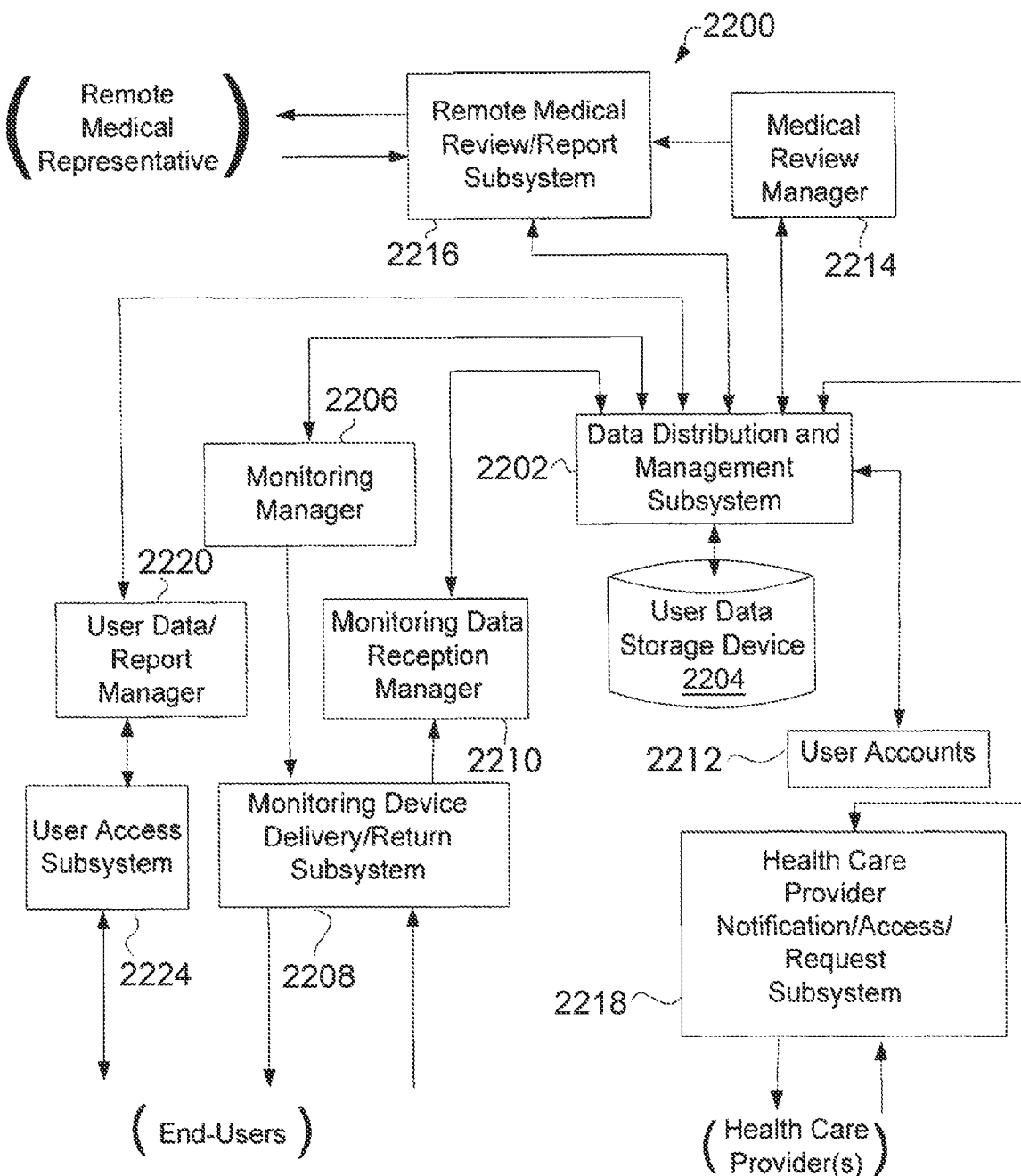
FIG. 27 is a block diagram of a health and wellness system according to one embodiment of the invention.

FIG. 27 is a block diagram of a health and wellness system 2200 according to one embodiment of the invention. The health and wellness system 2200 is, for example, suitable for use as the health data processing and management facility 2102 illustrated in FIG. 26.

In one embodiment, the health and wellness system 2200 includes various different subsystems. A data distribution and management subsystem 2202 serves as a central subsystem for the health and wellness system 2200. The data distribution and management subsystem 2202 couples to a user data storage device 2204. The user data storage device 2204 can store health and wellness data for a plurality of end-users.

The health and wellness system 2200 supports distributed health and wellness monitoring by the end-users. In this regard, the health and wellness system 2200 includes a monitoring manager 2206. The monitoring manager 2206 overseas the monitoring of one or more health and wellness issues or conditions of the end-users. In one embodiment, the monitoring manager 2206 couples to the data distribution and management subsystem 2202 and a monitoring device delivery/return subsystem 2208. The monitoring manager 2206 determines when end-users are to monitor certain health and wellness conditions. When requested by the monitoring manager 2206, the monitoring device delivery/return subsystem 2208 provides (e.g., delivers) a monitoring device to an end-user. The monitoring device can be, for example, sent by a courier or by postal mail, to the end-user. The monitoring device provided to the end-user is utilized by the end-user to acquire health and wellness data pertaining to the user. The type of monitoring device can vary widely depending upon the type of health and wellness data to be acquired. For example, when the health and wellness stated to be acquired are images of skin regions, the monitoring device can be an image capture device. Upon receiving the monitoring device, the end-user then utilizes the monitoring device to acquire the desired health and wellness data (e.g., images of skin regions). The monitoring device then can be returned to the monitoring device delivery/return subsystem 2208.

When the returned monitoring device is received by the monitoring device delivery/return subsystem 2208, a monitoring data reception manager 2210 extracts the health and wellness data from the returned monitoring device and provides such data to the data distribution and management subsystem 2202, which causes the health and wellness data to be stored in the user data storage device 2204. The data distribution and management subsystem 2202 can also process the incoming health and wellness data prior to or after being initially stored in the user data storage device 2204. The health and wellness data can also be referred to as user data. For example, the health and wellness data over a period of time may be processed (e.g., organized or correlated) through data processing operations so that the stored health and wellness data is more usable by health-care providers or medical representatives. Organizing the health and wellness data in a predetermined manner can provide a consistent data model that enables health care providers and medical representatives to efficiently review the stored health and wellness data.

The data distribution and management subsystem 2202 can also maintain user accounts 2212. The user accounts 2212 provide personal information regarding the users (name, address, age, social security number, insurance information, etc.), authorizations for data access that they have approved, their health-care provider, medical group, etc. The user accounts 2212 can also store user requests, conditions or preferences for types of health and wellness conditions to be monitored. With health and wellness data for a given user stored in the user data storage device 2204, the data distribution and management subsystem 2202 can determine that remote medical personnel should review the health and wellness data. In this regard, the data distribution and management subsystem 2202 can interact with a medical review manager 2214. The medical review manager 2214 can coordinate the medical review of health and wellness data for one or more users with remote medical representative. The medical review manager 2214 is operatively connected to the data distribution and management subsystem 2202 and to a remote medical review/report subsystem 2216. When the medical review manager 2214 desires to have a remote medical representative review the health and wellness data for one or more users, the medical review manager 2214 interacts with the remote medical review/report subsystem 2216. The remote medical review/report subsystem 2216 can then operate to forward appropriate requests and health and wellness data (or access thereto) to a remote medical representative. The remote medical representative then is able to review the health and wellness data and can prepare a report regarding his/her review. The report is typically provided as an electronic report. The report is then returned to the remote medical review/report subsystem 2216 which can cause the report to be stored by the data distribution and management subsystem 2202 in the user data storage device 2204.

Depending upon the nature of the report, a health-care provider (e.g., the user's primary care physician) may be consulted regarding the health and wellness data of the user. The health-care provider could be notified when the data distribution and management subsystem 2202 detects certain conditions. Such notifications can be computerized or automatic. For example, the data distribution and management subsystem 2202 can process the health and wellness data to determine whether suspect health conditions exist. Nevertheless, when the data distribution and management subsystem 2202 desires to interact with a health-care provider, a health-care provider notification/access/request subsystem 2218 is utilized. The health-care provider notification/access/request subsystem 2218 allows a health-care provider to (i) be notified, (ii) access health and wellness data from the user data storage device 2204, and (iii) request certain monitoring to be performed (either by the health-care provider or by the end-user).

The health and wellness system 2200 can also produce a user data report suitable for distribution to an end-user. Typically, the health and wellness system 2200 would produce a user report to provide health and wellness data to an end-user in a useful and user-friendly manner. A user data/report manager 2220 can be used to generate a user data report for an end-user. For example, a user preference as specified by the user may have specified periodic user reports to be provided to the end-user. On the other hand, the data distribution and management subsystem 2202 alone or together with the user data/report manager 2220 can determine when it is an appropriate time to provide user reports to end-users. In any case, when the user data/report manager 2220 determines that a user report is to be provided to an end-user, a user access subsystem 2224 permits a user report to be provided to the end-user, or permits the end-user to access the user report available from the user data/report manager 2220.

As noted above, the health and wellness data acquired by the monitoring device can pertain to images of skin regions. In one embodiment, the images can pertain to radiation in a visible range, which can be known as pictures or photographs. In another embodiment, the images can pertain to other sources, such as radiation in an infrared range, which can be known as thermal images. However, the health and wellness data used with the health and wellness system 2200 can be various other types of data as acquired by a monitoring device. For example, the health and wellness data that can be acquired, such as heart, kidney or lung performance data, chemical reaction data, etc. In one embodiment, the chemical reaction data results from a chemical to a bodily secretion. The health and wellness data can be used to monitor various illnesses, including asthma, diabetes, heart disease, HIV, lung disease, kidney disease, etc.

Figure 28A:
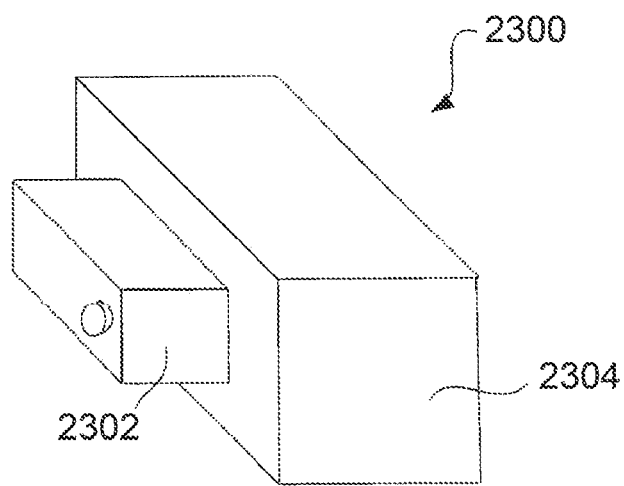
FIG. 28A is a perspective view of a skin monitoring system according to one embodiment of the invention.

FIG. 28A is a perspective view of a skin monitoring system 2300 according to one embodiment of the invention. The skin monitoring system 2300 includes a camera 2302 and a guide box 2304. The skin monitoring system 2300 is designed to facilitate capturing of skin images by end-users.

Figure 28B:
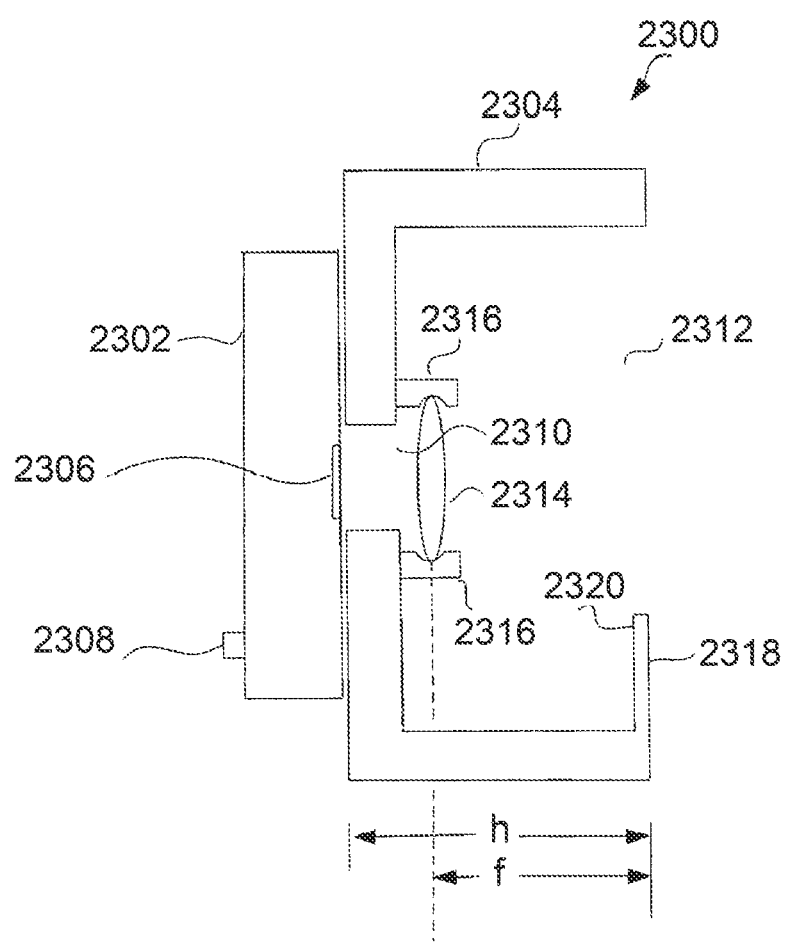
FIG. 28B is a cross-sectional view of the skin monitoring system illustrated in FIG. 28A according to one embodiment of the invention.

FIG. 28B is a cross-sectional view of the skin monitoring system 2300 illustrated in FIG. 28A according to one embodiment of the invention. As shown in FIG. 28B, the guide box 2304 has a smaller opening 2310 proximate to the camera 2302, and a larger opening 2312 at the opposite end of the guide box 2304. The camera 2302 is attached to the guide box 2304. In one embodiment, the camera 2302 is removably attached to the guide box 2304. Internal to the guide box 2304 is a lens 2314. When the camera 2302 is attached to the guide box 2304, an aperture 2306 for the camera is aligned with the lens 2314. The lens 2314 can be held in position by lens holders 2316. Although the opening 2312 of the guide box 2304 is a substantial portion of the area at that end of the guide box 2304, the guide box 2304 can include a partial back surface 2318. On the interior side 2320 of the partial back surface 2318 there can be provided a ruler or other markings. Such a ruler or markings can assist with the understanding of the size, nature or characteristics of an image or part of an image being captured. For example, when an image is acquired using the skin monitoring system 2300, the image will include the ruler or other markings, which provide a reference. The guide box 2304 has a height (h), and has a distance (f) from the end of the guide box 2304 to the lens 2314, which is the focusing distance of the lens 2314. Hence, when the skin monitoring system 2300 is utilized to capture skin images, the images are typically properly in focus, or otherwise acquired in a controlled environment. A push button 2308 on the camera 2302 allows the user to capture an image using the camera 2302. The aperture 2306 can also include a lens.

Although not shown in FIGS. 28A and 28B, the skin monitoring system 2300 can also include a light or flash device so as to provide light during capture of the skin images. For example, the light or flash device can provide light that is white, red, blue, infrared ultraviolet, or other color that is useful for imaging the skin region being analyzed. In one embodiment, the light or flash is provided by the camera 2302. For example, the light or flash device could be adjacent to the opening 2312 of the guide box 2304 or at another opening that can be provided in the guide box 2304. In another embodiment, the light or flash device could be attachable to the guide box 2304. In still another embodiment, the light or flash can be provided by the guide box 2304. In this situation, the light or flash device would be internal to the guide box 2304 and controlled by a switch. In any case, the light or flash device serves to provide uniform or appropriate lighting for image capture so that images can be relatively consistently properly exposed.

Figure 29A:
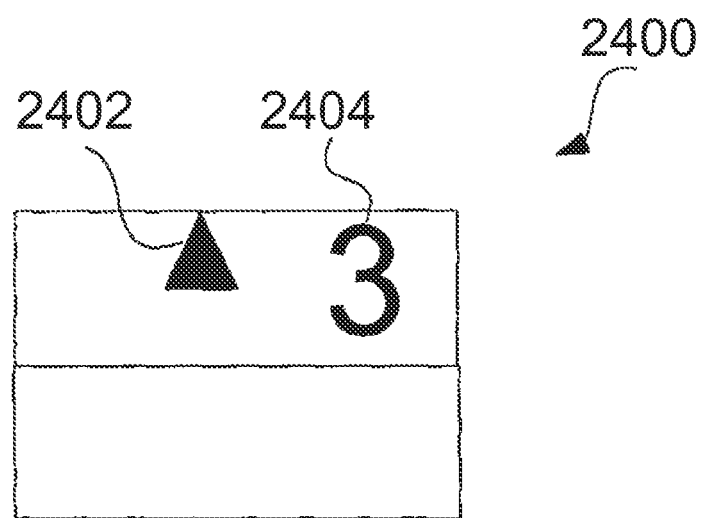
FIG. 29A is a view of a skin reference device according to one embodiment of the invention.

FIG. 29A is a view of a skin reference device 2400 according to one embodiment of the invention. A user can utilize the skin reference device 2400 to provide a reference at any skin area that is being captured by a camera or a skin monitoring system. The skin reference device 2400 includes a pointer 2402 and a reference number 2404. The skin reference device 2400 can, for example, be a label that can be placed on an end-user's skin such that the pointer 2402 points to the skin condition, mark or area that is to be captured by the system. Hence, when the image (e.g., picture or photo) of the skin condition, mark or area is captured, the image will include a depiction of the skin reference device 2400. The reference number 2404 can serve to provide a designator, which can be unique, for the skin condition, mark or area.

Figure 29B:
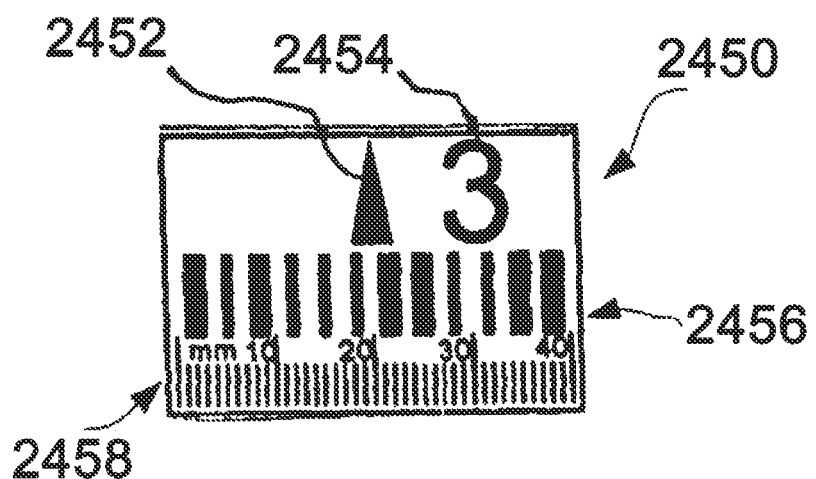
FIG. 29B is a view of a skin reference device according to another embodiment of the invention.

FIG. 29B is a view of a skin reference device 2450 according to another embodiment of the invention. The skin reference device 2450 includes a pointer 2452, a reference number 2454, a bar code 2456, and a ruler 2458. A user can utilize the skin reference device 2450 to provide a reference at any skin area that is being captured by a camera or a skin monitoring system. The skin reference device 2450 can, for example, be a label that can be placed on the end-user's skin such that the pointer 2452 points to the skin condition, mark or area that is to be captured by a skin monitoring system. The bar code 2456 can facilitate computerized recognition of the characteristics of the skin reference device 2450. For example, the bar code 2456 can signal to a computing system the reference number 2454. The bar code 2456 could also encode or be linked to various other information, such as user information, date, time, etc. The ruler 2458 facilitates review of the captured images, namely, understanding the size of a particular mark on the skin, which can be subsequently evaluated from an acquired image. For example, the ruler 2458 can allow a mark (e.g., lesion) to be compared over time, such as where the mark in a recently acquired image is of a different size (e.g., larger) than in a previously acquired image.

Figure 30A:
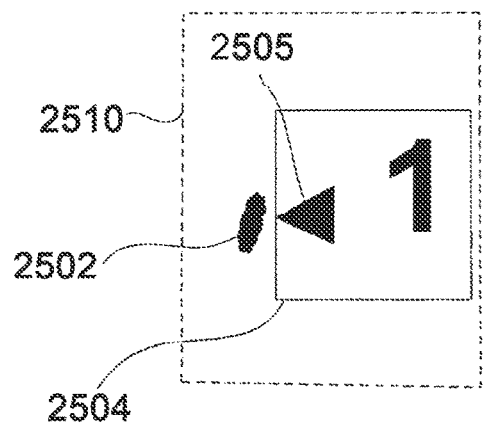
FIGS. 30A-30C illustrate how the skin reference devices can be utilized in acquiring appropriate images of skin conditions by an end-user according to one embodiment of the invention.
Figure 30B:
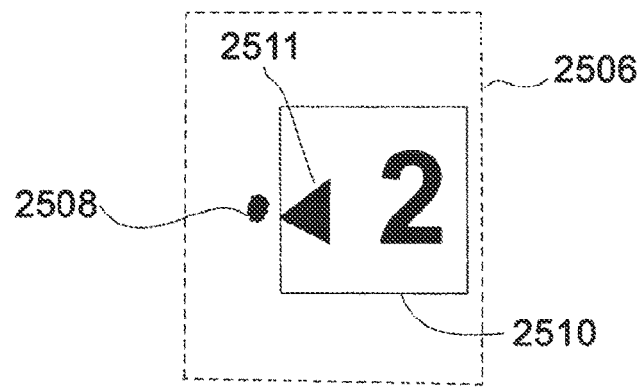
Figure 30C:
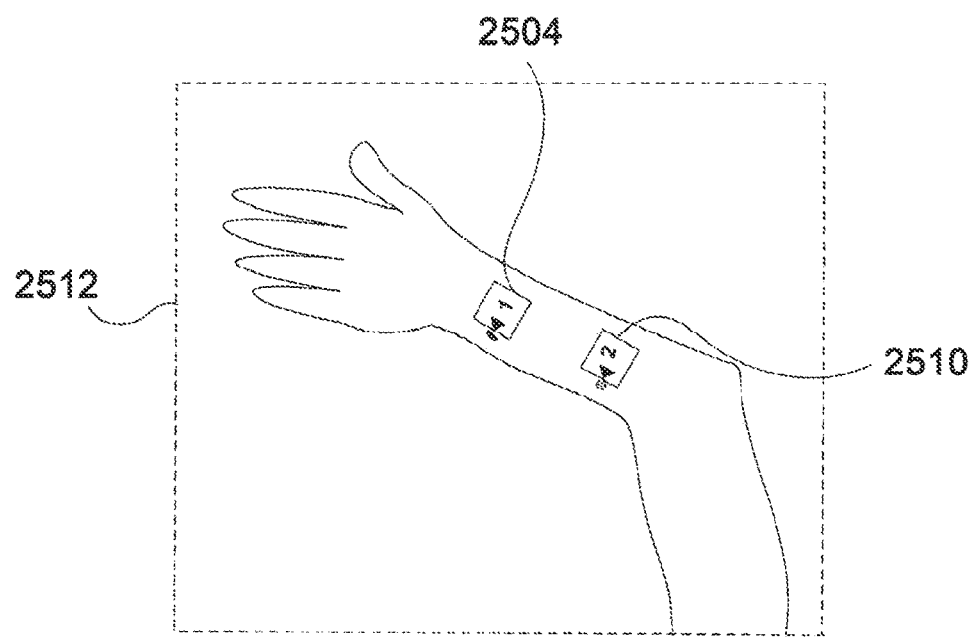

FIGS. 30A-30C illustrate how the skin reference devices according to one embodiment of the invention can be utilized in acquiring appropriate images of skin conditions by an end-user. The images of skin conditions are acquired by a skin monitoring system, such as the skin monitoring system 2300 illustrated in FIGS. 28A and 28B.

In FIG. 30A, a skin reference device 2504 is provided proximate to a skin condition 2502. The pointer 2505 of the skin reference device 2504 is directed to the skin condition 2502. Then, using the skin monitoring system, an image 2500 of the skin condition 2502 and the skin reference device 2504 is captured. Similarly, in FIG. 30B, a skin reference device 2510 is provided proximate to a skin condition 2508. The pointer 2511 of the skin reference device 2510 is directed to the skin condition 2508. Then, using the skin monitoring system, a second image 2506 is captured. Note that the skin reference device 2504 includes a reference number 1, and the skin reference device 2510 includes a reference number 2. The images 2500 and 2506 can be considered close-up images of the skin conditions 2502 and 2508, respectively. Given the use of the skin monitoring system, the images 2500 and 2506 can be clear, properly exposed and in focus. However, capturing additional images from a perspective further from the skin surface can aid in the understanding of the precise position of the skin conditions being monitored with respect to other parts of the end-user's body. For example, in FIG. 30C, an image 2512 includes a substantial portion of the end-user's arm. As shown in FIG. 30C, the skin reference devices 2504 and 2510 remain on the end-user's arm when the image 2512 was acquired. Hence, the image 2512 provides context as to where the skin conditions 2502 and 2508 reside with respect to the arm of the end-user.

A camera can be used to capture the images. In one implementation, the camera can have two different lens systems. In another implementation, the camera can have one lens with two different focal settings, with one focal setting used for the close-up images (e.g., images 2500 and 2506) and the other focal setting used for the context images (e.g., images 2512).

In one embodiment, there can be a CCD array or other image detector(s) at the smaller opening 2310, such as at the aperture 2306. The lens 2314 can be positioned at a focusing distance (f) so that for close-up pictures, the images (e.g., images 2500 and 2506) can be in focus at the image detector(s), such as at the aperture 2306. For context pictures, the lens 2314 can be moved closer to the aperture 2306 to a different focusing distance (f) so that the context images (e.g., images 2512) can be in better focus at the image detector(s). In one embodiment, there can be a small lever or other type of moving mechanisms to move the lens 2314 from the close-up position to the context position. In another embodiment, the camera 2302 can be a commercial camera, such as a disposable digital camera, with its own lens system. The lens 2314, which can be a lens system, can be designed so that when the lens 2314 is positioned at a focusing distance (f), close-up images (e.g. images 2500 and 2506) are in focus at the image plane of the camera. For context images (e.g. images 2512), the lens 2314 can be removed (or moved) to allow the camera to take pictures. In one embodiment, the lens 2314 can be removed manually, and in another embodiment, the lens 2314 can be moved by a mechanical system, such as a lever.

In one embodiment, when images are taken, they are also time-stamped to record when the images are taken. Since each image can be electronically identified relative to its position at the body of the end-user, multiple images of the same location can be compared relative to each other as a function of time. For example, images with reference number 1 are compared as a function of time. The images document the change or the lack of change of the skin condition 2502 as a function of time. In one embodiment, when a medical representative is reviewing the images, the system automatically collects and organizes the images with the same reference number. Then they can be shown to the representative chronologically as a function of time on a screen. All the images can be shown on the screen simultaneously with a time-stamp indicated below each image. In another embodiment, only recent images are shown to show how a skin condition has been changing recently. For example, only images in the last twelve months can be, at least initially, shown to the medical representative.

In another embodiment, the system automatically performs image processing on the images pertaining to skin condition. For example, based on edge-recognition techniques, the system automatically identifies the size of a skin condition and computes the approximate area occupied by the skin condition. If the area changes by more than a preset percentage over a preset period of time, then the skin condition could be considered as a suspect skin condition. In such cases, a medical representative could be alerted to review the images.

According to another embodiment of the invention, thermal radiation can be measured and utilized to determine skin condition or other health conditions associated with a user. According to one implementation, skin associated with the user can be locally heated and then one or more thermal images are acquired at the corresponding skin region. The thermal image(s) acquired can be evaluated as discussed herein. More generally, an embodiment of the invention can first excite or induce a portion of the body by an excitation source, and then measure responsiveness to such excitation. As one example, the excitation can be a heat source to apply heat to a body portion (e.g., skin region), and the measurement can be thermal imaging of the body portion that has been previously heated. Thermal imaging can be done by a thermal image acquisition device, and the images can be used to determine, for example, the rate of heat dissipation by the previously heated body portion.

Figure 30D:
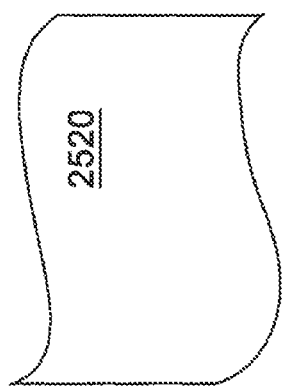
FIGS. 30D-30F illustrate how devices according to another embodiment of the invention can be utilized in acquiring appropriate images by an end-user.
Figure 30F:
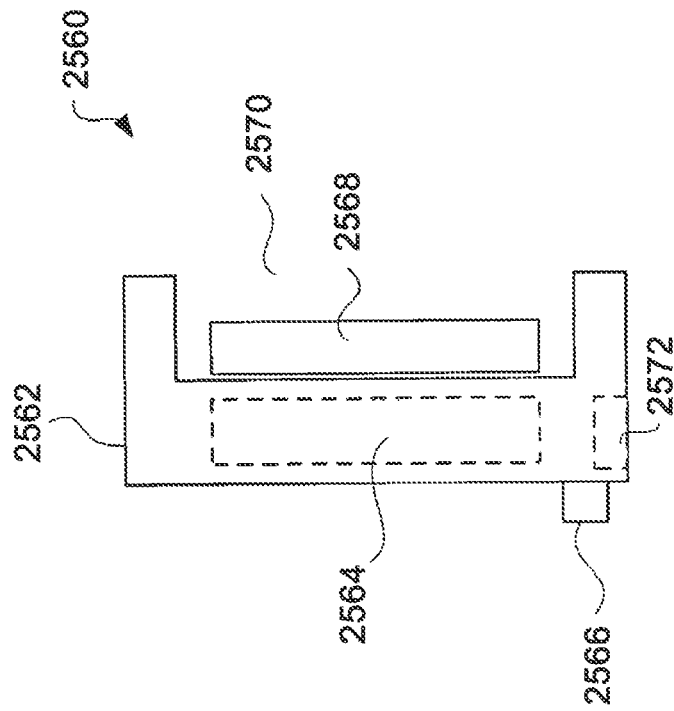
Figure 30E:
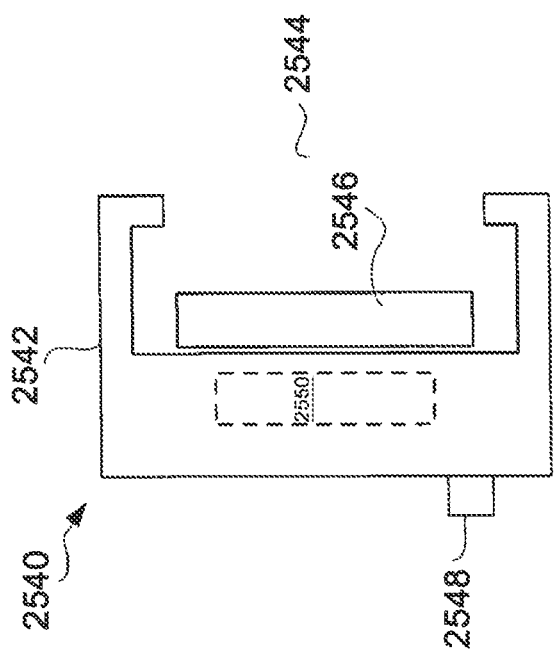

FIGS. 30D-30F illustrate how devices according to another embodiment of the invention can be utilized in acquiring appropriate images by an end-user. In the embodiment illustrated in FIGS. 30D-30F, images of skin conditions can be acquired. In one implementation the images being acquired are thermal images.

FIG. 30D illustrates a thermal wrap 2520 according to one embodiment of the invention. The thermal wrap 2520 can pertain to a piece of cloth, fabric, or other material that can be utilized to apply heat to a portion of a user's body. The thermal wrap 2520 can also be considered a thermal blanket. The thermal wrap 2520 can itself generate heat or can retain heat that was otherwise previously applied to the thermal wrap 2520. In any case, the thermal wrap 2520 can be placed on a portion of the body and utilized to heat that portion of the body. Typically, the portion of the body is associated with a region of skin on the body.

FIG. 30E illustrates a cross-sectional view of a heater 2540 according to one embodiment of the invention. The heater 2540 represents another approach to heating a portion of the body. The heater 2540 includes a housing 2542. One end of the housing 2542 includes an opening 2544. The end of the housing 2542 having the opening 2544 is applied against a portion on the user's skin. A heating element 2546 provided within the housing 2542 generates heat. The heat from the heating element 2546 can be absorbed by the user's skin adjacent to the opening 2544. In addition, the housing 2542 also can include an on/off switch 2548 that can be used to activate/deactivate the heating element 2546. Still further, the housing 2542 can include electrical circuitry 2550 that is utilized to control the heating element 2546 to produce the appropriate amount of heat. The on/off switch 2548 can also be connected to the circuitry 2550. The heater 2540 can be powered by a battery provided within the housing 2542 or it can be powered by an external source, e.g., external battery or an AC outlet via an electrical cord.

In FIG. 30E, the heating element 2546 receded (or set back) from the opening 2544. In another embodiment, the heating element 2546 can be provided at the opening 2544, and can be flexible or malleable to conform to the curvature of the skin or body part that is being heated. In such an embodiment, the heating element 2546 can be in contact with the region to be heated.

FIG. 30F illustrates a cross-sectional view of an image acquisition device 2560 according to one embodiment of the invention. The image acquisition device 2560 includes a housing 2562. The housing 2562 includes internal circuitry 2564, a switch 2566, and a thermal imaging sensor 2568. The thermal imaging sensor 2568 is provided facing the end of the housing 2562 having an opening 2570. When the image acquisition device 2560 is placed on a portion of the user's skin, the skin is adjacent to not only the opening 2570 but also the thermal imaging sensor 2568. The thermal imaging sensor 2568 can then acquire one or more thermal images associated with the portion of the user's skin.

In one embodiment, the thermal imaging sensor 2568 is represented by a two-dimensional arrangement of thermocouples arranged in a two-dimensional array. In another embodiment, the thermal imaging sensor 2568 is a sheet of material with thermochromic paint. Thus, in this embodiment, instead of an infrared array or other image detector(s) at an aperture, such as the aperture 2306 in FIG. 28B, the thermal imaging sensor can be a sheet of material whose characteristics change as a function of temperature.

In the embodiment shown in FIG. 30F, the imaging sensor 2568 receded (or set back) from the opening 2570. In another embodiment, the imaging sensor 2568 can be provided at the opening 2570, and can be malleable or flexible. For example, the thermal imaging sensor 2568 includes a sheet of transparent plastic with thermochromic paint on a first surface. That first surface is at the opening 2570, facing away from the inside of the housing 2562. The plastic can conform to the surface to be measured to allow the thermochromic paint to be substantially in contact with the surface. There can be the thermal imaging sensor 2568 (e.g., a digital camera) on the other side of the plastic, opposite to the first surface. With the plastic being transparent, the thermal imaging sensor 2568 can take pictures of the thermochromic paint to register its color change.

The circuitry 2564 can control the acquisition of a thermal image by the thermal imaging sensor 2568, such as under the control of the switch 2566. The circuitry 2564 can also include circuitry (e.g., memory) to store the acquired thermal image. The image acquisition device 2560 can optionally include a peripheral port 2572, such as a USB port. The peripheral port 2572 can be utilized to upload data from the image acquisition device 2560 to another electronic device, such as a personal computer.

In yet another embodiment, the image acquisition device and the heating device are integrated or incorporated in a package. One example is based on the transparent plastic sheet with thermochromic paint, as described above. There can be heating wires embedded in the plastic, such as in the configuration of a mesh. When current passes through the wires, the plastic heats up, and can be used as the heating device. When used as the image acquisition device, current is removed from the wires. Initially, the thermochromic paint still registers areas of elevated temperature due to the heating wires. After the heating wires have cooled off, the thermochromic paint can be used to image the temperature of the portion of the skin that the paint is adjacent.

Figure 31A:
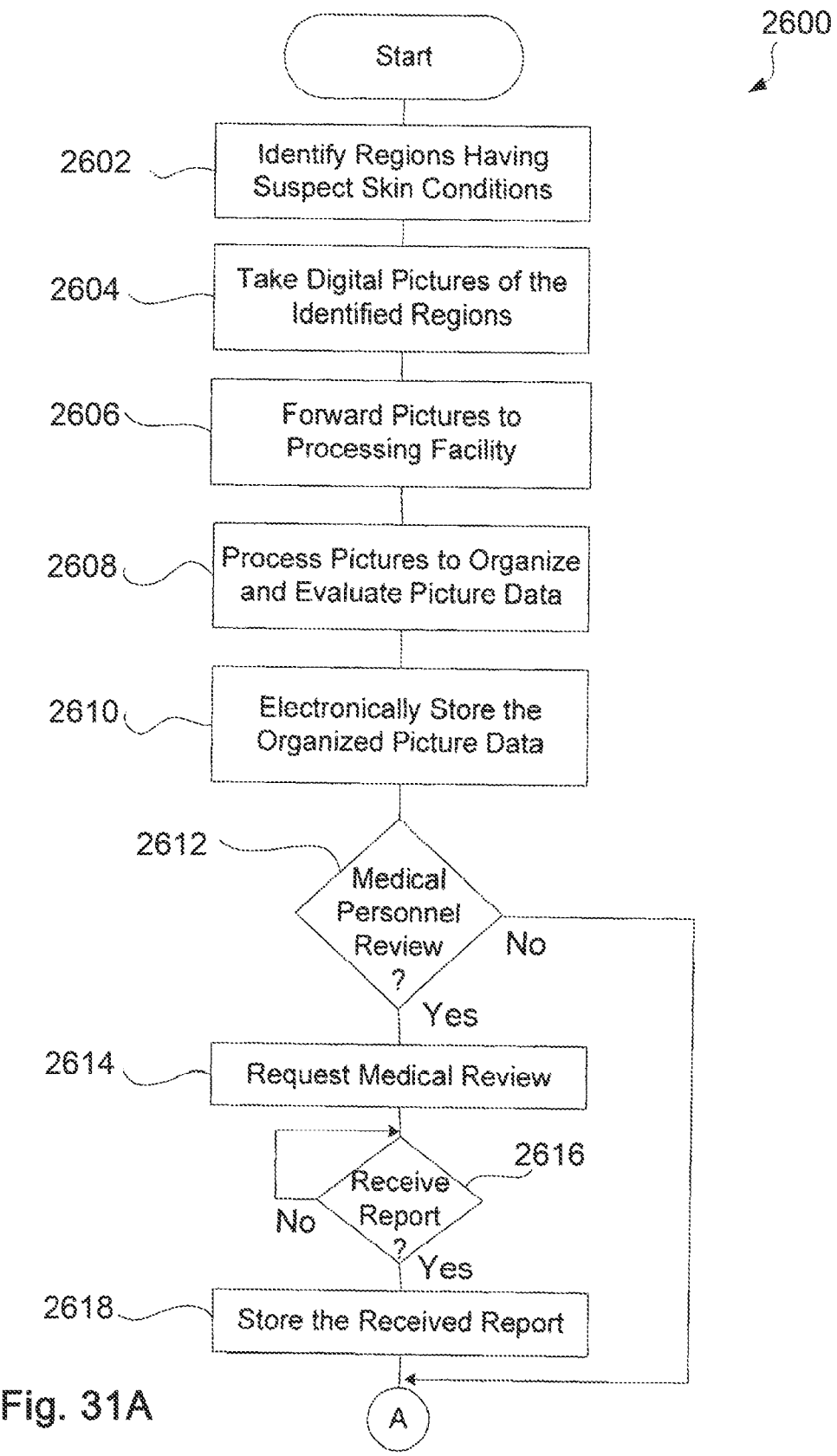
FIGS. 31A and 31B are flow diagrams of a skin monitoring process according to one embodiment of the invention.
Figure 31B:
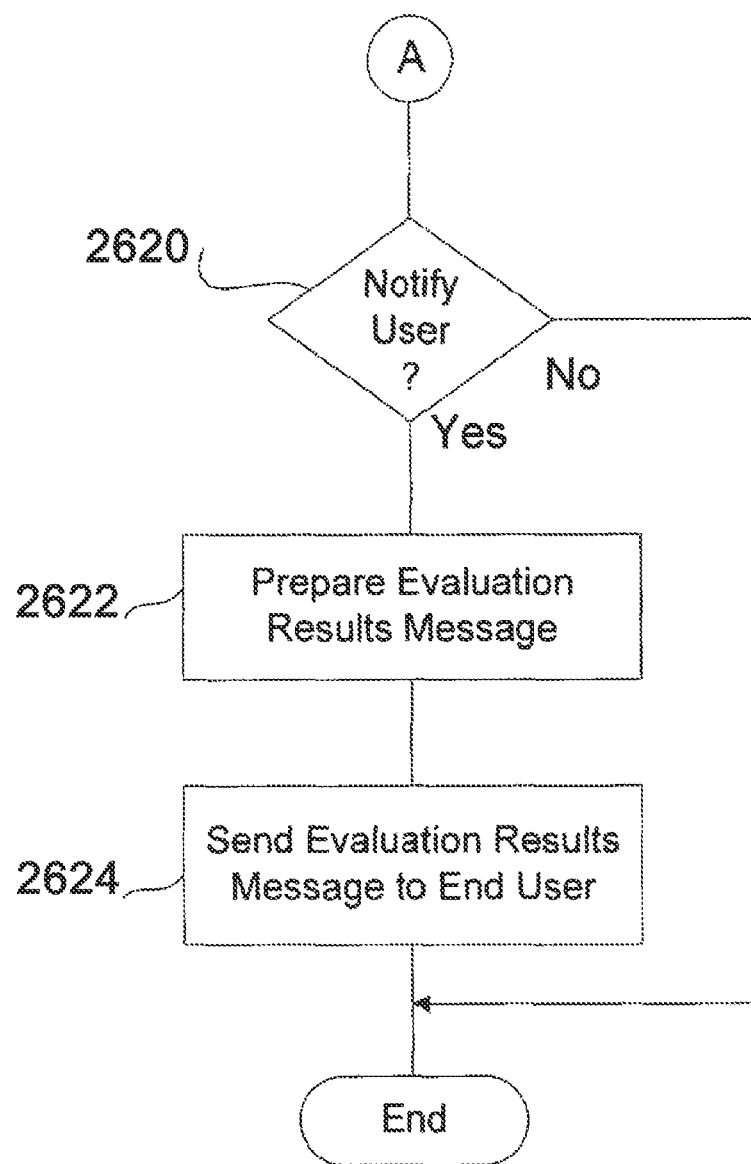

FIGS. 31A and 31B are flow diagrams of a skin monitoring process 2600 according to one embodiment of the invention. The skin monitoring process 2600 is, for example, performed by a user and a computing device.

The skin monitoring process 2600 initially identifies 2602 regions having suspect skin conditions. Then, digital pictures are taken 2604 of the identified regions. In one embodiment, the digital pictures are taken 2604 using a skin monitoring system, such as the skin monitoring system 2300 illustrated in FIGS. 28A and 28B. After the digital pictures are taken 2604, the digital pictures are forwarded 2606 to a processing facility. The digital pictures can be forwarded 2606 in a variety of different ways, including by courier, postal mail, electronic file transfer or electronic mail. The forwarding 2606 of the pictures can involve the forwarding of the electronic data or can involve the forwarding of the skin monitoring system, or a camera portion thereof, that includes the digital pictures.

When the digital pictures arrive at the processing facility, the digital pictures are processed 2608, which can include organizing and evaluating the picture data. The organized picture data is then electronically stored 2610. Subsequently, a decision 2612 determines whether medical personnel should review the picture data. When the decision 2612 determines that medical personnel should review the picture data, a medical review is requested 2614.

There can be different approaches to determine that medical personnel should review the picture data. In one embodiment, when picture data arrives, medical personnel will be alerted to review the arrived data. In another embodiment, the picture data can be initially electronically evaluated. For example, computerized processing at the processing facility can perform an evaluation of the picture data in an automated fashion. To illustrate, in the context of monitoring skin conditions, the electronic evaluation can monitor size, rate of growth, and/or color (pigmentation). Regarding monitoring the rate of growth, the electronic evaluation could check the picture data against prior picture data. If the electronic evaluation indicates one or more suspected regions, medical personnel can be summoned. Different embodiments have been described in electronically determining problematic images of skin problems in U.S. Patent Publications, 2005/0119551 A2 and 2004/0218810 A1, both of which are hereby incorporated herein by reference.

In response to the medical review request, a medical person can review and prepare a report regarding the picture data. Hence, the skin monitoring process 2600 can await the reception of such a report. Here, a decision 2616 determines whether a report has been received from a medical person. When the decision 2616 determines that a report has not yet been received, the skin monitoring process 2600 can await such a report, though other processing or acts can be performed while awaiting a report. Once the decision 2616 determines that a report has been received, the received report is stored 2618. Alternatively, when the decision 2612 determines that medical review is not requested at this time, then blocks 2614 through 2618 are bypassed.

Following the block 2618, or its being bypassed, a decision 2620 determines whether the end-user should be notified. In one embodiment, the end-user can be notified after the medical review of the images. In another embodiment, the end-user can be notified if there are problematic images. In still another embodiment, user preferences provided by an end-user can determine or influence when the end-user is to be notified (and/or how). In yet another embodiment, notification of an end-user can be determined or influenced by a practitioner performing a review or by a health care provider.

The end-user can be notified of the medical data, the medical review/report, etc. when the decision 2620 determines that the end-user is to be notified. When the end user is to be notified, an evaluation results message is prepared 2622. The evaluation results message can include medical data, medical review/reports regarding the medical data, recommendations, preventative care treatments, and/or additional related information. After the message is prepared, the evaluation results message is sent 2624 to the end-user. The evaluation results message can be sent 2624 in a variety of different ways, including such as by courier, postal mail, electronic file transfer or electronic mail. Alternatively, when the decision 2620 determines that the end-user is not to be notified, the blocks 2622 and 2624 are bypassed. Following the block 2624, or its being bypassed, the skin monitoring process 2600 is complete and ends. In one embodiment, the blocks 2602 and 2604 are performed by or with the assistance of end-users, whereas the blocks 2606-2624 are performed by one or more computing devices.

Figure 31C:
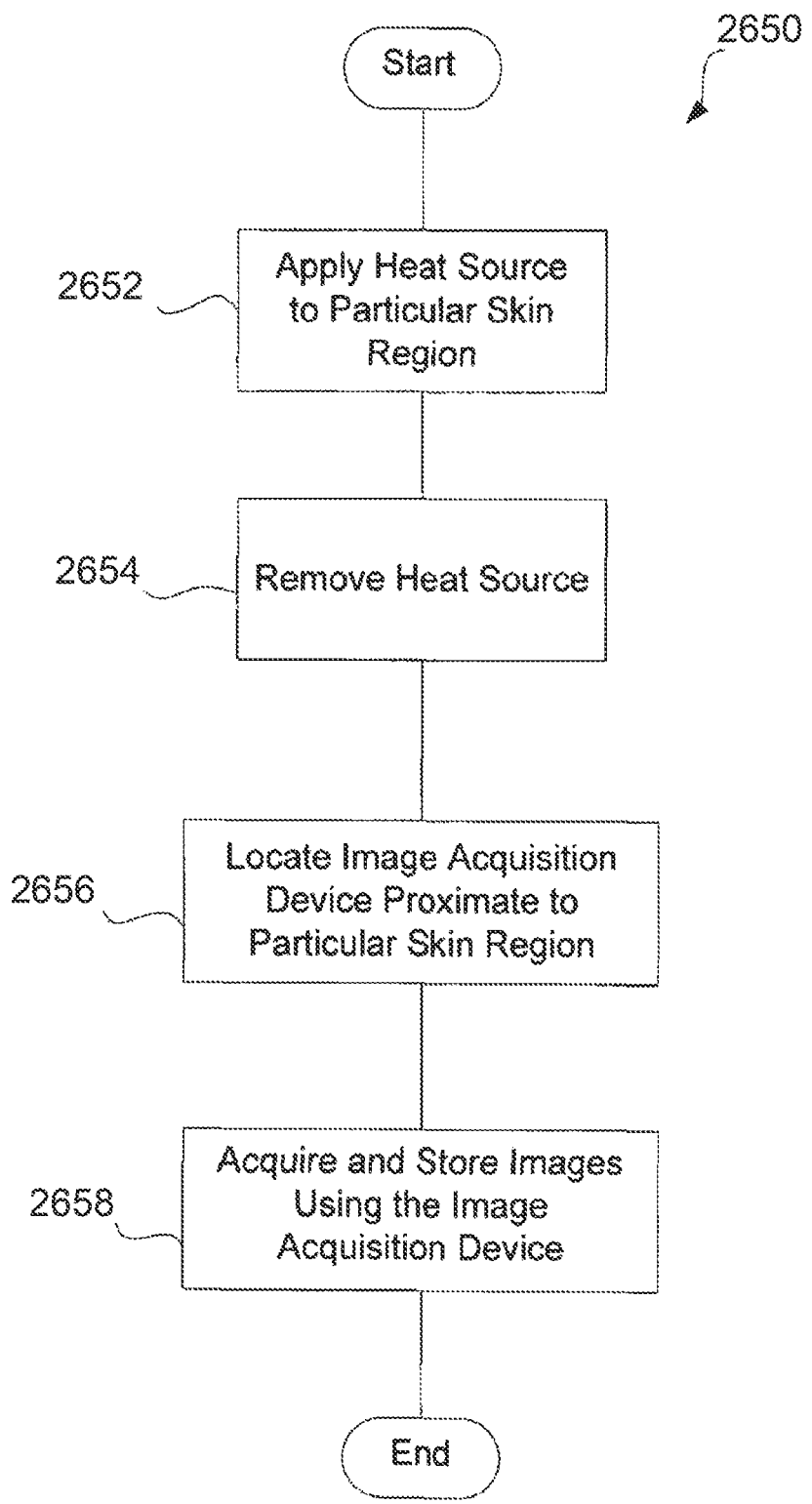
FIG. 31C is a flow diagram of an image acquisition process according to one embodiment of the invention.

FIG. 31C is a flow diagram of an image acquisition process 2650 according to one embodiment of the invention. The image acquisition process 2650 can, for example, be performed by a user utilizing a thermal wrap or heater as well as an image acquisition device.

The image acquisition process 2650 initially can apply 2652 a heat source to a particular skin region. Here, the heat source produces heat that is transferred to the particular skin region. After the appropriate amount of heating of the particular skin region, the heat source can be removed 2654. Then, an image acquisition device can be located 2656 proximate to the particular skin region. Thereafter, one or more images of the particular skin region can be acquired and stored 2658 using, for example, the image acquisition device. In this embodiment, the images are thermal images associated with a thermal mapping of the particular skin region in response to the prior heating of such region. Following the block 2658, the image acquisition process 2650 can end. Once the thermal images are acquired, the thermal images can be processed and evaluated, such as by processes similar to processing other images discussed herein.

Figure 32:
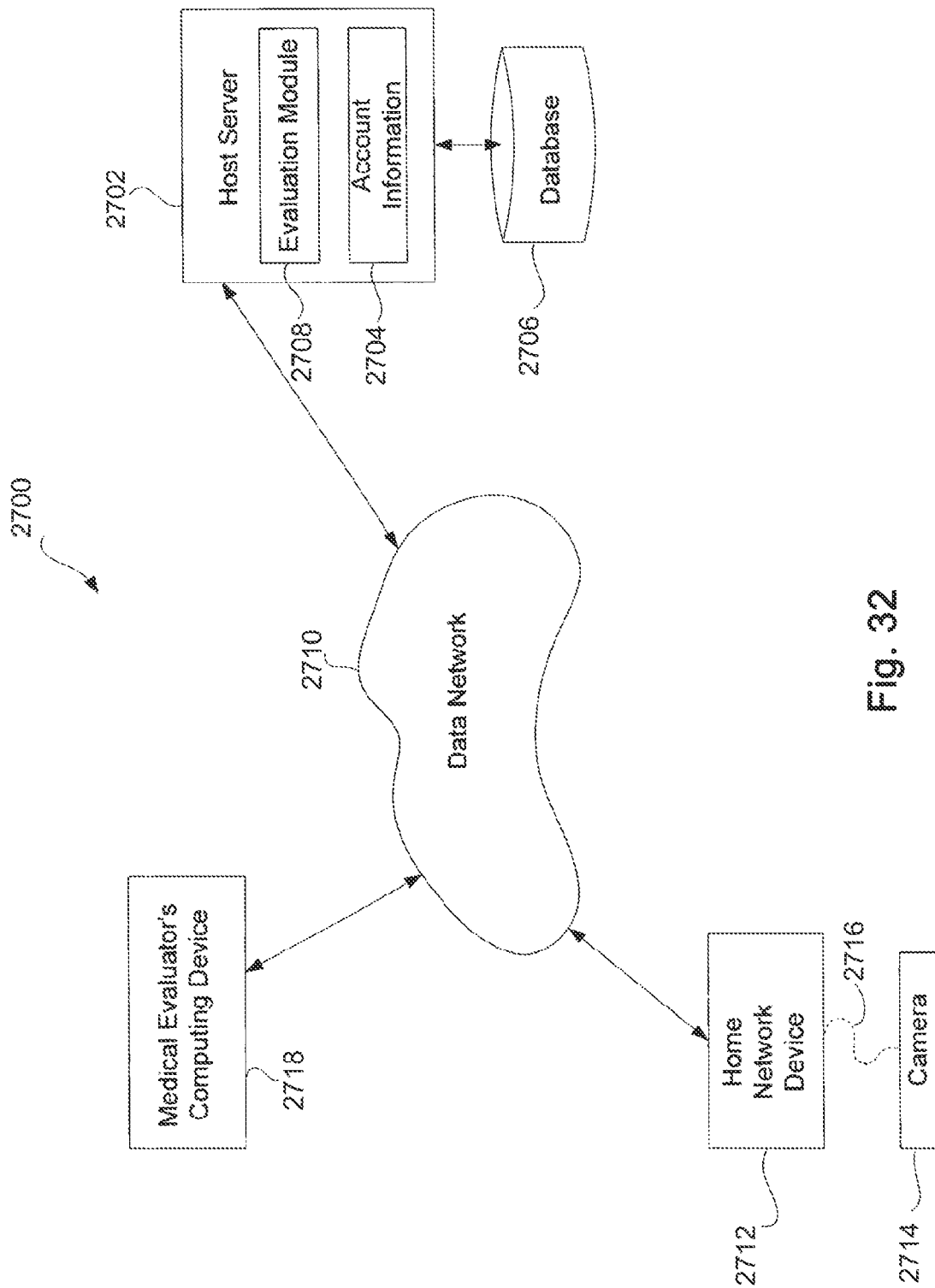
FIG. 32 is a distributed health and wellness system according to one embodiment of the invention.

FIG. 32 is a distributed health and wellness system 2700 according to one embodiment of the invention. The distributed health and wellness system 2700 includes a host server 2702, which can be a networked computer. The host server 2702 stores account information 2704 corresponding to a plurality of registered end-users. The host server 2702 maintains health and wellness data for the various end-users. The health and wellness data is typically stored in a database 2706. The host server 2702 can also process the health and wellness data using an evaluation module 2708.

The host server 2702 couples to a data network 2710. The data network 2710 can be a wide area or global area network. For a given end-user, a home network device 2712 can couple to the data network 2710. For example, the home network device 2712 can be a personal computer or a personal health and wellness system for in-home or personal use. In one embodiment, the home network device 2712 supports the capture of images pertaining to health and wellness of an end-user, and a camera 2714 is utilized by the end-user. The end-user uses the camera 2714 to capture images corresponding to health and wellness conditions of the end-user. In one approach, the camera 2714 is capable of electrically coupling to the home network device 2712 over a link 2716. The link 2716 can be a wireless link or a wired link or a connector established link.

In one embodiment, the distributed health and wellness system 2700 can further permit medical evaluators to access the health and wellness data for the various end-users being stored by the host server 2702. In this regard, the health and wellness data, such as the health and wellness images provided by the camera 2714, can be uploaded by the home network device 2712 through the data network 2710 to the host server 2702. The host server 2702 can store the health and wellness images in the database 2706 such that they are associated with the pertinent user account associated with the end-user. The host server 2702 can also process the health and wellness data using the evaluation module 2708. The evaluation module 2708 can evaluate whether specific medical conditions exist based on a computerized examination of the health and wellness data. The evaluation module 2708 can also determine whether a medical evaluation by a medical evaluator (or medical representative) should be performed using the health and wellness data associated with a particular end-user. When the host server 2702, namely, the evaluation module 2708, determines that a medical evaluator should review the health and wellness data for a particular end-user, the host server 2702 can notify a medical evaluator's computing device 2718 via the data network 2710. The medical evaluator associated with the medical evaluator's computing device 2718 can then access the health and wellness data for the particular end-user via the host server 2702 and provide an evaluation of any existing health and wellness conditions that require attention. The medical evaluation or report can then be returned to the host server 2702 via the data network 2710. The report can also be stored in the database 2706.

Figure 33A:
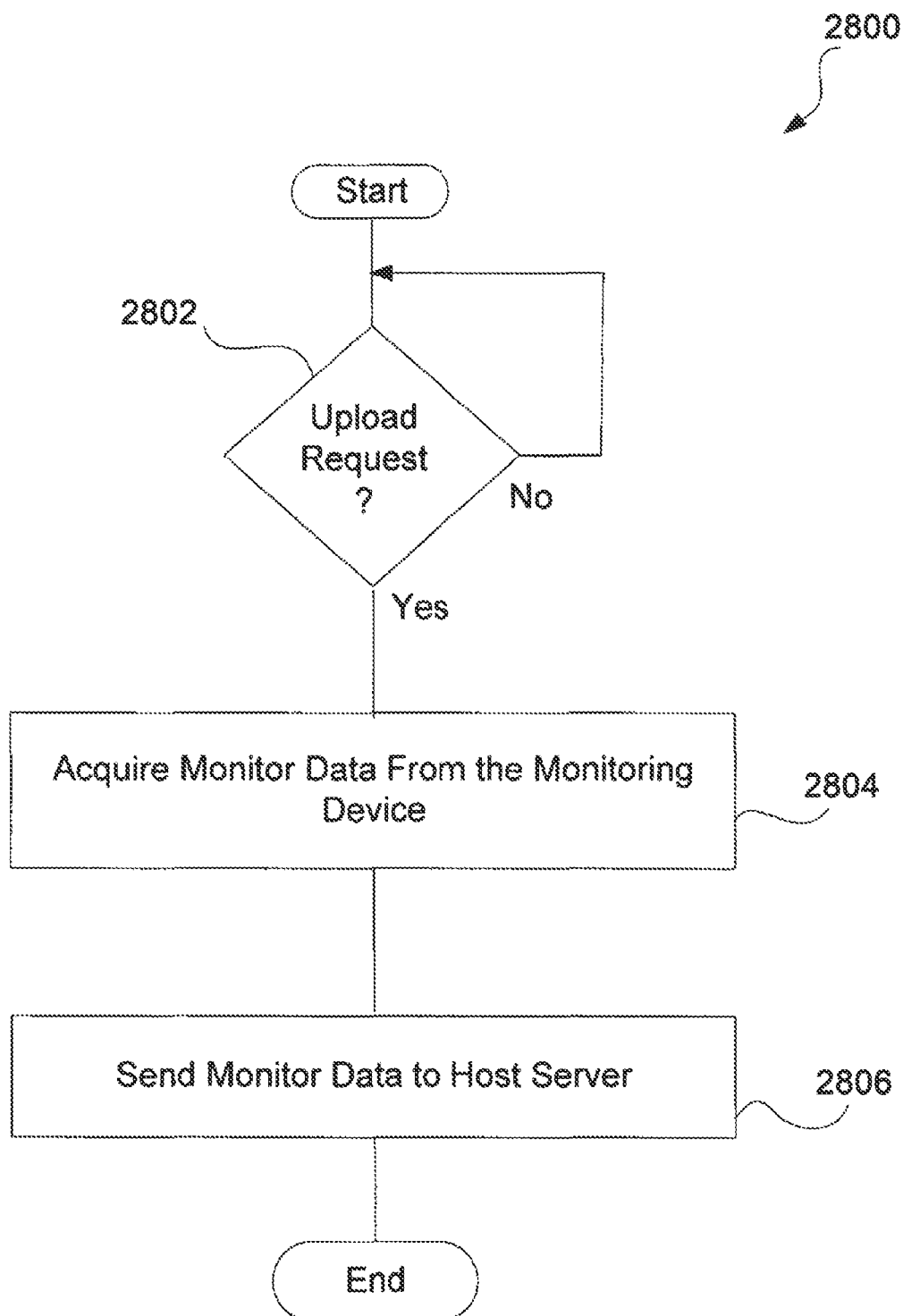
FIG. 33A is a flow diagram of a monitoring data upload process according to one embodiment of the invention.

FIG. 33A is a flow diagram of a monitoring data upload process 2800 according to one embodiment of the invention. The monitoring data upload process 2800 can, for example, be performed by the home network device 2712 illustrated in FIG. 32. The monitoring data upload process 2800 begins with a decision 2802. The decision 2802 determines whether an upload request has been received. An upload request can be provided by an end-user through a manual user action, or can be automatically initiated by the home network device 2712, or can be requested by the host server 2702. In any case, when the decision 2802 determines that an upload request has not been received, then the monitoring data upload process 2800 awaits such a request. Once the decision 2802 determines that an upload request has been received, data, including monitoring data, from the monitoring device is acquired 2804. The monitor data is then sent 2806 to the host server. Typically, to secure the monitoring data, the monitor data would be encrypted prior to its transmission to the host server. Additionally, the home network device 2712 could authenticate the camera 2714 prior to transmission of the monitor data to the host server. The home network device 2712 also could authenticate itself with the host server 2702. The authentication of the camera

2714 can ensure that the camera 2714 is authorized for use with the host server 2702. The authentication of the home network device 2712 can ensure that the home network device 2712 is authorized for use with the host server 2702 and/or ensure that the user of the home network device 2712 is an authorized (and registered) user of the system. After the monitor data has been sent to the host server, the monitoring data upload process 2800 is complete and ends.

Figure 33B:
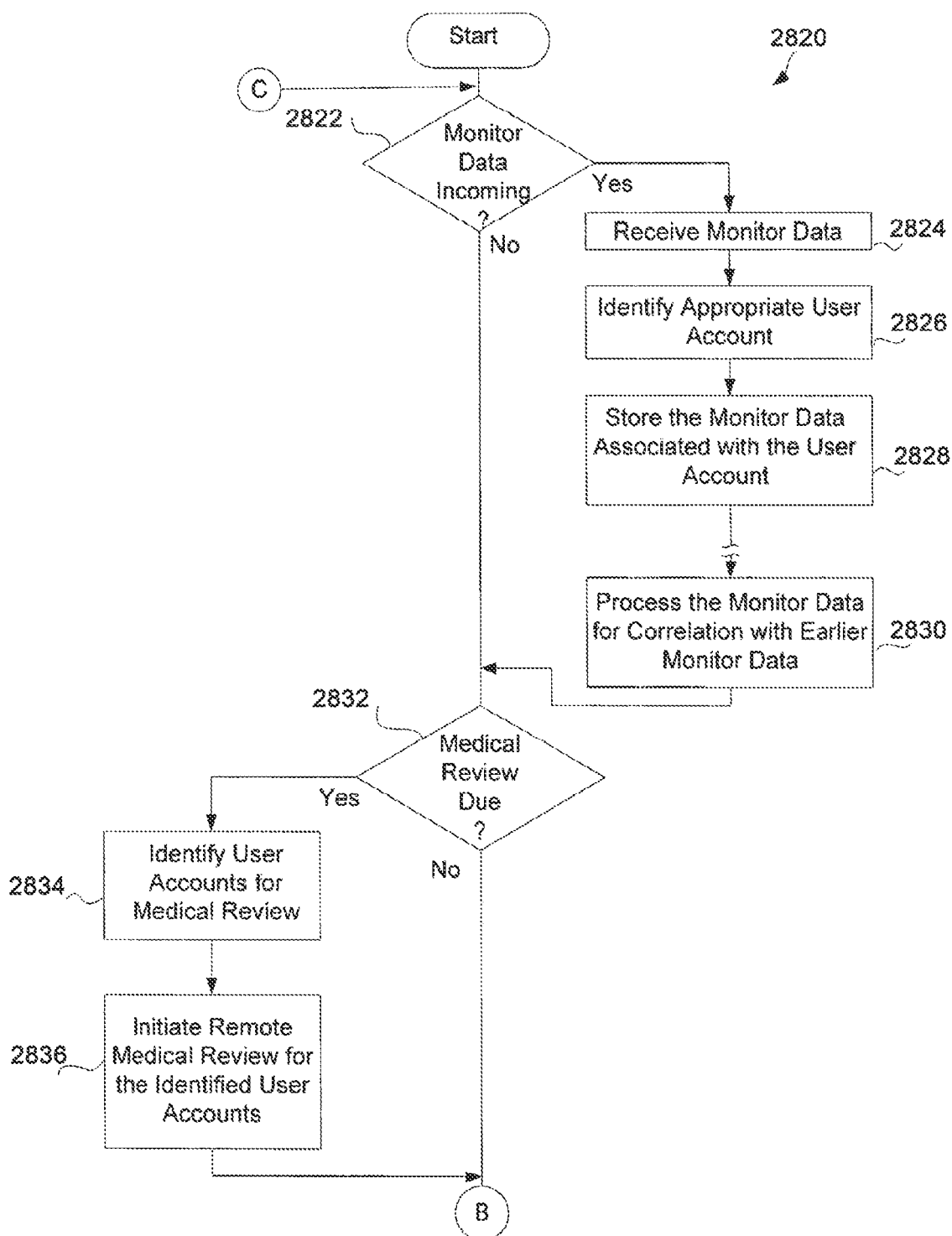
FIGS. 33B and 33C are flow diagrams of a host server process according to one embodiment of the invention.
Figure 33C:
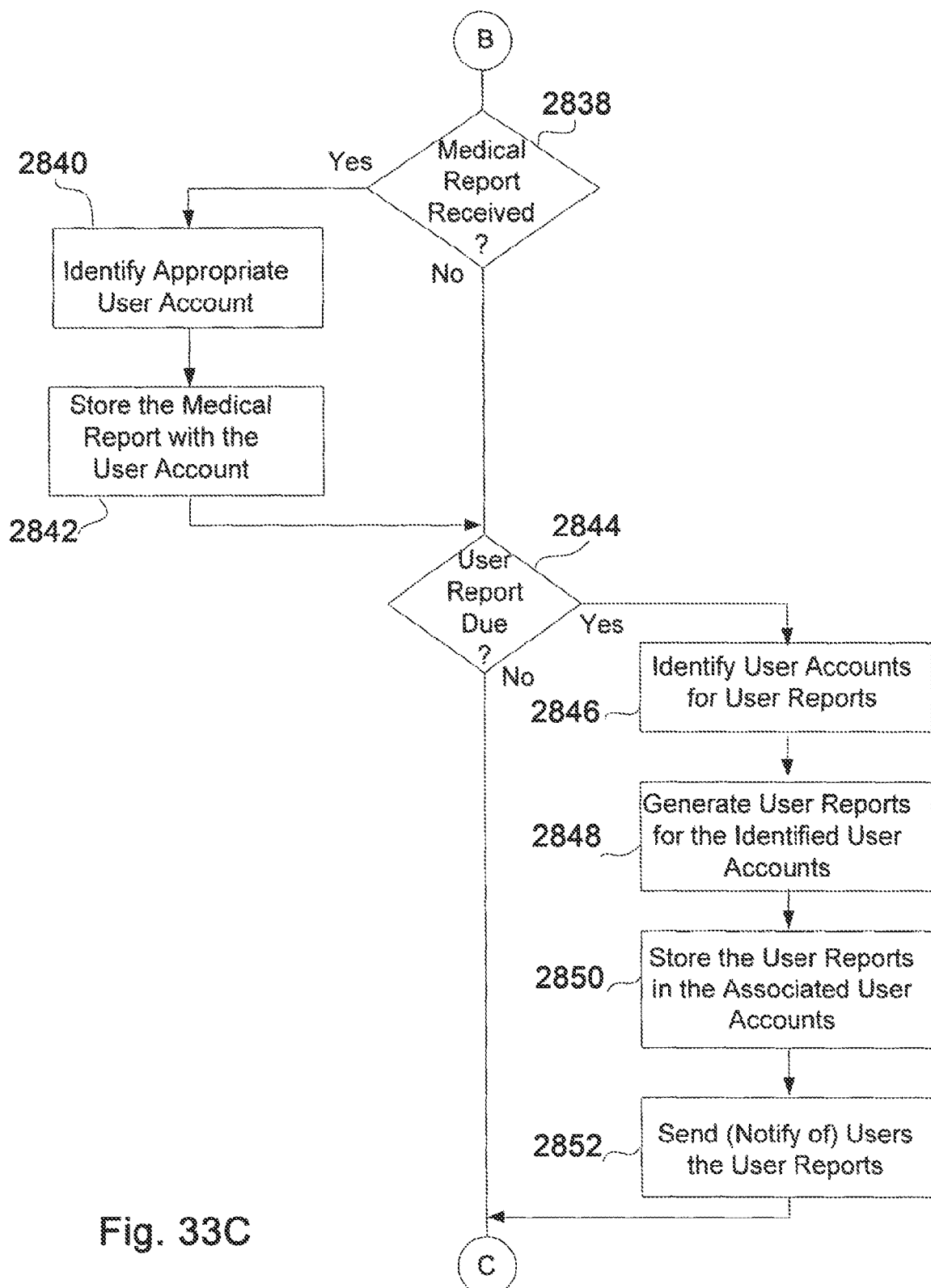

FIGS. 33B and 33C are flow diagrams of a host server process 2820 according to one embodiment of the invention. For example, the host server process 2820 can be performed by the host server 2702 illustrated in FIG. 32.

The host server process 2820 begins with a decision 2822. The decision 2822 determines whether monitor data is incoming. When the decision 2822 determines that monitor data is incoming, the monitor data is received 2824. In addition, an appropriate user account may be identified 2826. If the monitor data is associated with a particular end-user, the identification 2826 of the appropriate user account can be important. If the monitor data is associated with a particular end-user, next, the monitor data is stored 2828 such that it is associated with the corresponding user account. Subsequently, although other processing may intervene, the monitor data can be processed 2830 for correlation with earlier monitor data. The ability to correlate current monitor data with earlier monitor data can be advantageous when the monitor data is provided over an extended period of time and the evolution and change in the monitor data is important for health and wellness evaluation.

Following the block 2830, or directly following the decision 2822 when the monitor data is not incoming, a decision 2832 determines whether a medical review is due or appropriate. A medical review can be initiated by the host server 2702. For example, the medical review could be periodically requested or could be requested when the evaluation module 2708 indicates that irregularity (or certain particular features) exists in the monitor data. In any case, when the decision 2832 determines that a medical review is due or appropriate, one or more user accounts for medical review are identified 2834. Then, medical review or remote medical review for the identified user accounts is initiated 2836.

Following the block 2836, or directly following the decision 2832 when a medical review is not due, a decision 2838 determines whether a medical report has been received. When the decision 2838 determines that a medical report has been received, an appropriate user account associated with the medical report is identified 2840. Then, the medical report is stored 2842 associated with the user account.

Following the block 2842, or following the decision 2838 directly when a medical report has not been received, a decision 2844 determines whether a user report is due. When the decision 2844 determines that a user report is due, a user account for one or more user reports are identified 2846. User reports are then generated 2848 for the identified user account. The user reports are then stored 2850 in the associated user accounts. Thereafter, the user is sent (or notified of) 2852 the user reports.

Following the block 2852, or directly following the decision 2844 when a user report is not due, the host server process 2820 returns to repeat the decision 2822 and subsequent blocks so that the host server process 2820 can repeat and process other incoming data or requests.

Figure 34:
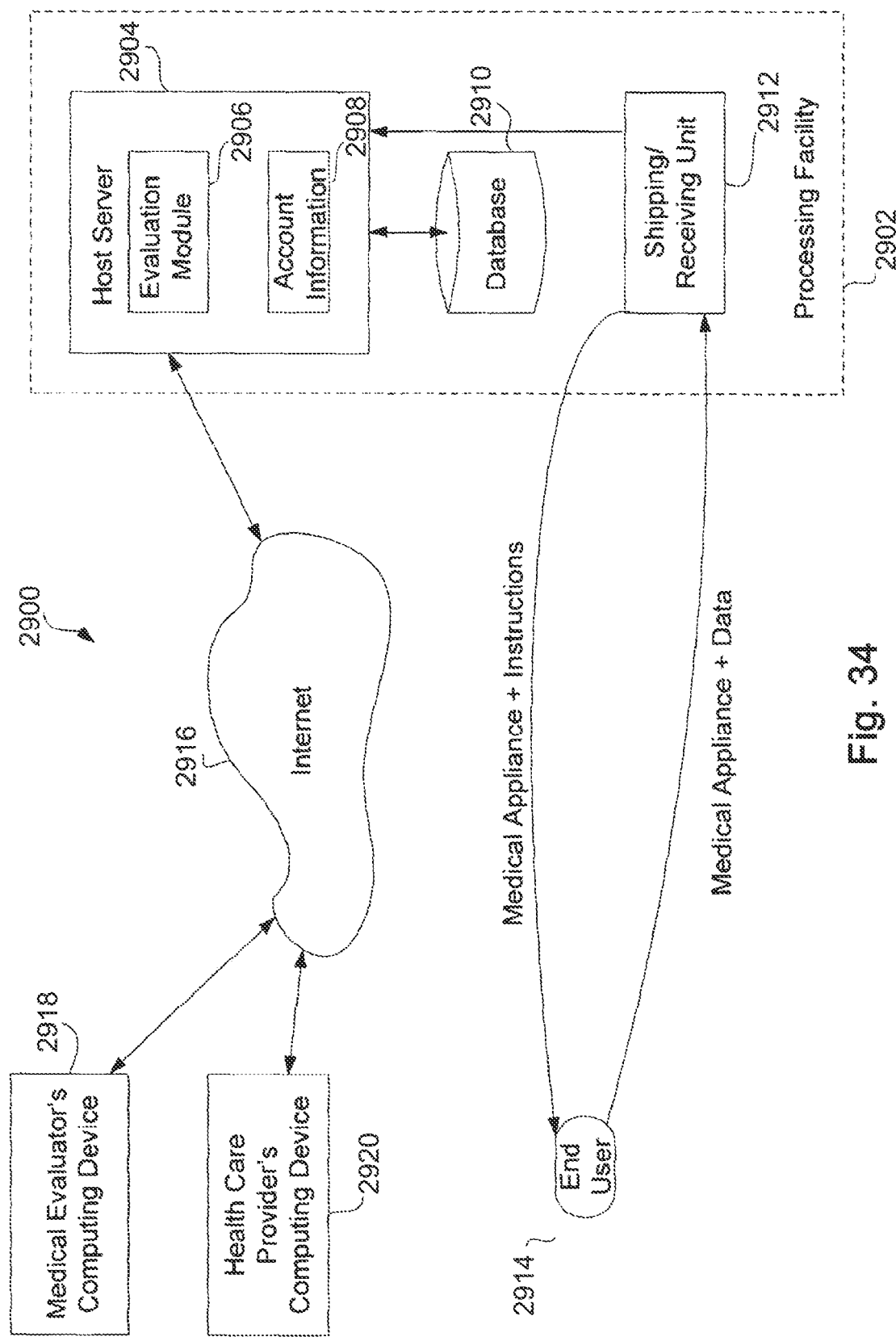
FIG. 34 is a distributed health and wellness system according to another embodiment of the invention.

FIG. 34 is a distributed health and wellness system 2900 according to another embodiment of the invention. The distributed health and wellness system 2900 includes a processing facility 2902. The processing facility 2902 includes a host server 2904. The host server 2904 is a computing device that controls overall operation of the processing facility 2902. The host server 2904 includes an evaluation module 2906 and account information 2908. Coupled to the host server 2904 is a database 2910. The database 2910 can store health and wellness data corresponding to various end-users who have registered with the host server 2904 and have account information stored in the account information area 2908. The processing facility 2902 also includes a shipping/receiving unit 2912. The shipping/receiving unit 2912 operates to send shipments to and receive shipments from a plurality of different end-users 2914 and other facilities. In particular, the shipping/receiving unit 2912 can ship a medical appliance together with usage instructions to an end-user 2914. The instructions can inform the end-user 2914 about how to use the medical appliance to acquire health and wellness data. After the end-user 2914 has used the medical appliance, the end-user 2914 can return all or a portion of the medical appliance together with the acquired health and wellness data back to the shipping/receiving unit 2912 of the processing facility 2902.

The shipping/receiving unit 2912 can then acquire the health and wellness data for the end-user 2914 from the returned materials, such as the returned medial appliance, and supplies such to the host server 2904. The host server 2904 associates the health and wellness data to the associated user and stores such health and wellness data in the database 2910. The evaluation module 2906 can then evaluate the health and wellness data within the database 2910 to determine when a remote medical evaluation is to be performed by a medical person. When the evaluation module 2906 indicates that a medical evaluation is appropriate, the host server 2904 informs a medical evaluator's computing device 2918, which can be a personal computer, PDA, or cell phone, via a network 2916, such as the Internet, that an evaluation of certain health and wellness data is requested. The medical person associated with the medical evaluator's computing device 2918 can then access the health and wellness data for the user of interest and perform an evaluation. The evaluation is then returned to the host server 2904 via the network 2916, and then stored in the database 2910.

In some embodiments, the medical evaluation is done by a medical person that is capable of evaluating specific health and wellness data. For example, the medical person can be a specialist that specializes in reviewing images of skin conditions. In such case, the medical specialist can be very efficient in reviewing the health and wellness data for their specific field(s) of expertise. On the other hand, the medical person could be a more general practice type medical person, or could even be the health care provider for the end-user. In any case, the distributed health and wellness system 2900 can also permit health care providers' computing devices access to the processing facility 2902, namely, access the health and wellness data associated with end-users under their care. Hence, a health-care provider's computing device 2920 can couple to the host server 2904 via the Internet 2916.

Figure 35A:
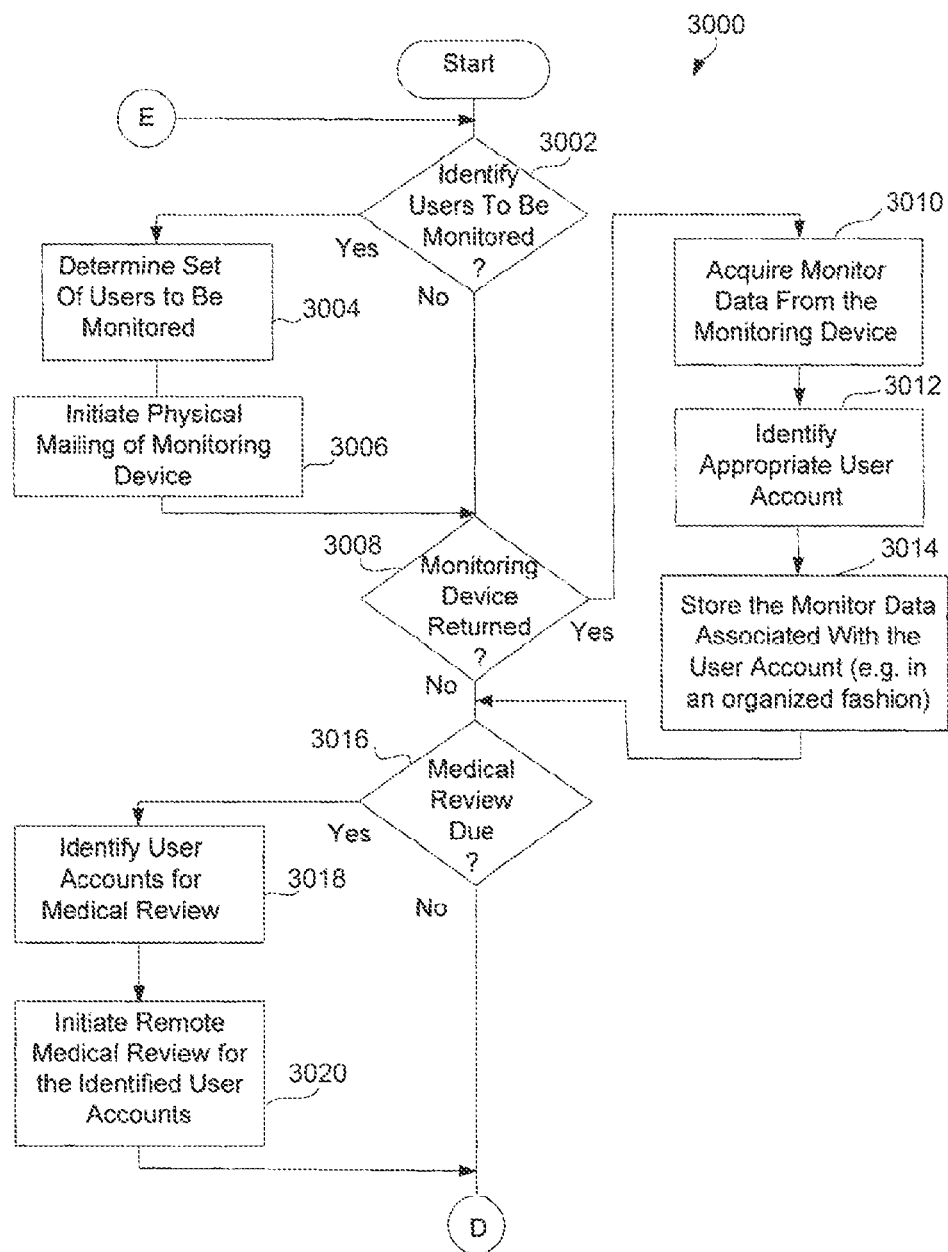
FIGS. 35A and 35B are flow diagrams of a server process according to one embodiment of the invention.
Figure 35B:
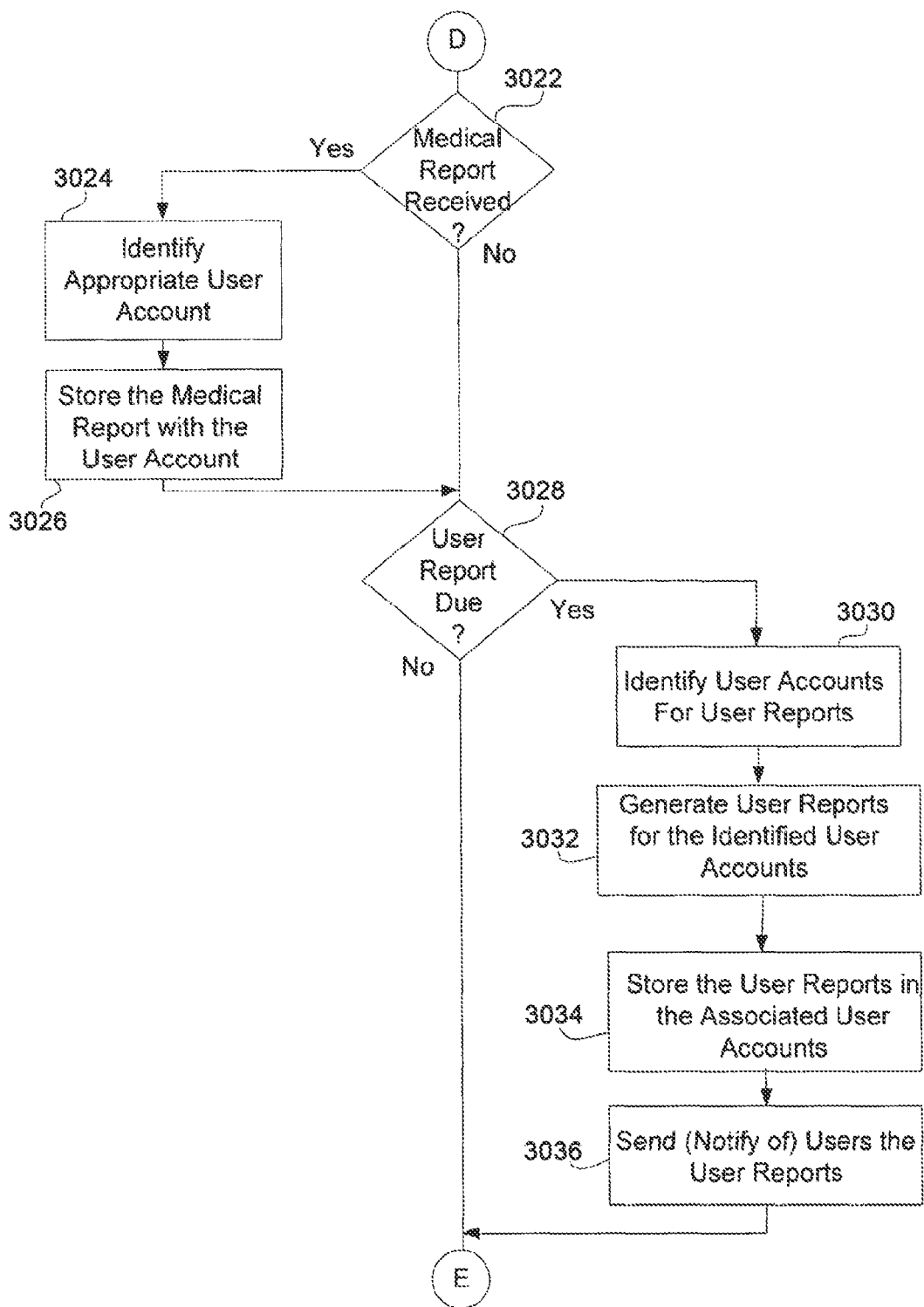

FIGS. 35A and 35B are flow diagrams of a server process 3000 according to one embodiment of the invention. The server process 3000 is, for example, performed by a host server, such as the host server 2904 illustrated in FIG. 34.

The server process 3000 begins with a decision 3002 that determines whether one or more users to be monitored are to be identified. When the decision 3002 determines that a number of users to be monitored are to be identified, a set of users to be monitored is determined 3004. Then, physical mailing of monitoring devices is initiated 3006 to the set of users. The physical mailing can, for example, be performed or controlled by the shipping/receiving unit 2912 illustrated in FIG. 34.

Following the block 3006, or directly following the decision 3002 when the decision 3002 determines that users to be monitored are not to be identified at this time, a decision 3008 determines whether a monitoring device has been returned. When the decision 3008 determines that a monitoring device has been returned, such as to the shipping/receiving unit 2912, monitored data can be acquired 3010 from the returned monitoring device. An appropriate user account is identified 3012. The monitored data associated with the user account is then stored 3014. Normally, the monitored data would be stored such that it is organized with respect to previously stored data for the corresponding user. In other words, the data can be correlated with earlier data to provide organized storage. With the data stored in an organized manner, subsequent evaluation of the data can become more efficient and, for certain wellness data, more accurate.

Following the block 3014, or directly following the decision 3008 when the decision 3008 determines that a monitoring device has not been returned, a decision 3016 determines whether a medical review is due or appropriate. When the decision 3016 determines that a medical review is due, one or more user accounts for medical review are identified 3018. In one embodiment, medical review can be initiated periodically for each user, by a health care provider's request, by an end-user's request, and/or automatically by computerized evaluation of the stored monitored data. The medical review can be of different types, including different conditions, diseases, infections, etc. Then, remote medical review for the identified user accounts can be initiated 3020. Here, the server process 3000 can select from a variety of different medical evaluators such that the evaluator to be utilized is appropriate for the type of medical review desired. The medical evaluator that provides the remote medical review can complete a report for the evaluation he or she has performed.

Following the block 3020, or directly following the decision 3016 when a medical review is not due, a decision 3022 determines whether a medical report has been received. When the decision 3022 determines that a medical report has been received, an appropriate user account associated with the medical report is identified 3024. Then, the medical report is stored 3026 associated with the user account.

Following the block 3026, or following the decision 3022 directly when a medical report has not been received, a decision 3028 determines whether a user report is due. When the decision 3028 determines that a user report is due, one or more user accounts for one or more user reports are identified 3030. One or more user reports are then generated 3032 for the identified user accounts. The user reports can then be stored 3034 in the associated user accounts. Thereafter, one or more users are sent (or notified of) 3036 the user reports.

Following the block 3036, or directly following the decision 3028 when a user report is not due, the host server process 3000 returns to repeat the decision 3002 and subsequent blocks so that the host server process 3000 can repeat and process other incoming data or requests.

In still another embodiment of the invention, a distributed health and wellness system can provide a medical monitoring device or appliance at a retail or discount store. A customer, while visiting the store, can purchase the medical monitoring device or appliance. In one embodiment, the medical monitoring device or appliance can be provided within a kit that further includes one or more of a computer readable medium including computer program code for execution by a computer to assist the customer (user) in acquiring and transmitting health data to a remote facility, either physically or electronically, instruction for operation of the medical monitoring device or appliance, and/or possibly a cable for connecting the medical monitoring device or appliance to a host device (e.g., computer) server.

The medical monitoring device or appliance can monitor various different health or wellness conditions of a user. As an example, the medical monitoring device or appliance can monitor skin or other conditions, chemical analysis for bodily fluids, etc. The medical monitoring device or appliance can, for example, be a probe, a container, or sensor. The medical monitoring device or appliance can use one or more of a reagent, an electrical component, an electrical circuit, and data storage.

Figure 36:
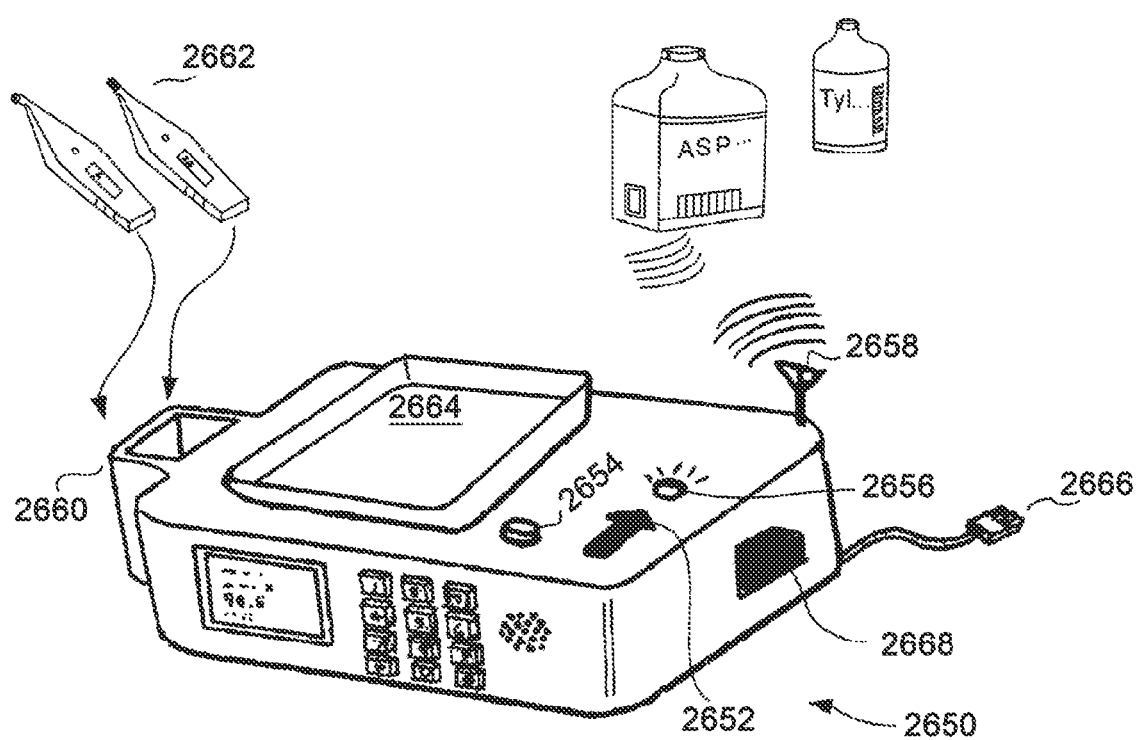
FIG. 36 shows one embodiment of such a base that can be electrically coupled to a medical monitoring device or appliance.

In one embodiment, any of a number of functions previously described as being performed by a medical monitoring device or appliance can be performed by a base. FIG. 36 shows one embodiment of such a base 2650 that can be electrically coupled to a medical monitoring device or appliance.

In one embodiment, in such a base implementation, operations performed by a medical monitoring device can be minimized. For example, when the user gets his medication from a pharmacist, the device, such as a bottle, can include information regarding the prescription, which can include the user's schedule to take the medication. Such information can be on a barcode, a RFID tag or in a memory in the device, according to different embodiments. The user can facilitate downloading such information from the device into the base 2650. For example, if the information is in a barcode on a device, the base 2650 can include a barcode reader 2652. The user can push a start button 2654, and then the user can scan the barcode to enter such information into the base 2650. When the barcode is successfully scanned, a signal can be provided to the user, such as a light 2656 can turn on, or an audio feedback can be provided by a speaker. Note that different pharmacies might use different barcodes. In one embodiment, information regarding different barcodes from the different pharmacies is stored in the base 2650. In one embodiment, the base 2650 can include a RFID tag reader, including its antenna 2658, to access the information stored in an RFID tag.

Alternatively, the device or appliance can include an electrical connector. The user can connect the device's connector to a base connector at the base 2650 to download the information. In one embodiment, the device's connector is located at the bottom of the device. There can be a recessed space on top of the base 2650 to receive the device. When the user puts the device into the space, with the device's connector received by the base's connector, information in the device can be downloaded into the base. In one embodiment, the device's connector can be at the bottom of the device. The device's connector can be a standard connector, such as a USB connector. The connector can be slightly recessed into the device, allowing the device to firmly stand on a flat surface, without the connector sticking out.

In one embodiment, the base 2650 includes a slot 2660 to receive a sensor 2662, such as a thermometer. The slot 2660 can be used to track different measurements regarding an end-user. Each time a sensor is stationed in the space, such as inserted into the slot 2660, measurements made by the sensor 2662, such as in the past 24 hours, are uploaded to the base 2650. The upload can be through a connector at the sensor 2662 with a corresponding connector at the base 2650. The sensor 2662 is one example of a medical monitoring device or appliance that can be used with the base 2650.

In one embodiment, the base 2650 can also include a scale 2664. An end-user can weigh a device with the scale 2664. The scale 2664 can also be at a recessed space on top of the base 2650 to receive the device. In another embodiment, as the device sits on the scale 2664, its RFID tag is read by a RFID tag reader in the base 2650.

In another embodiment, the base can have multiple recessed spaces for more than one device. The base can also have multiple slots for more than one sensor to be stationed.

In another embodiment, the base 2650 can include a connector 2666 to connect to other devices or instruments, such as a computer. Instead of a physical connector, the connection can also be wireless. Based on such connections, the base 2650 can be connected, for example, to another area, such as a website. Information in the base 2650 can be accessed and the base 2650 can also access information from the another area, such as the website. In yet another embodiment, the base 2650 can also include another input/output connector 2668, which can be for a memory device, such as a flash memory card.

In one embodiment, the base 2650 can keep track of the time, the date, the weight of a medical monitoring device, sensor measurements from a medical monitoring device and/or the identity of the end-user using the base 2650 and/or medical monitoring device. In one embodiment, the device can contain medication. For example, the device can be a bottle of pills. Every time the end user uses the device, the user can place the device on a selected space on the base 2650 to weigh the device and to download information into the base 2650. This would allow the base 2650 to keep track of information related to the user taking the medication.

In one embodiment, since the device can keep track of the type of substance taken by the user, as the user takes different types of substances, such as from different devices, the information regarding the substance can be downloaded into the base 2650 accordingly. Based on information in the base 2650, or information accessed from a remote site or area, the base can provide indication to the user that the different types of medication the user is taking, conflict with each other and can cause complications to the user.

In one embodiment, a base 2650 is, or performs the functions of, a medical monitoring system. In another embodiment, a base 2650 can be considered personal to an end-user in the sense that the user typically does not want to share it with another end-user if the another person is using the base 2650 for similar purposes as the user. This can be similar to a toothbrush, which is usually considered personal to the user. However, the user may be willing to let a healthcare provider use it because the provider is typically using the base 2650 for different purposes, such as to access information from it to diagnose the user.

Different processes have been described regarding analyzing and processing images captured. In one embodiment, the analysis includes color analysis. For example, the colors of optical images of lesions can be analyzed to provide additional skin condition information.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

Certain aspects of the invention can be implemented in software, hardware or a combination of hardware and software. Certain aspects of the invention can also be embodied as computer readable code on a computer readable medium. The computer readable medium is any data storage device that can store data which can thereafter be read by a computer system. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

The advantages of the invention are numerous. Different embodiments or implementations may yield one or more of the following advantages. One potential advantage of a number of embodiments of the invention is that health care costs can be significantly lowered. Another potential advantage of a number of embodiments of the invention is that through use of technology associated with the invention, quality health care can be provided in the privacy and convenience of one's home. More people may be interested in checking themselves more often and more regularly, given its ease of use and given that the user's portion of the testing can be done in the privacy of the user's home. Still another potential advantage of a number of embodiments of the invention is that a health and wellness system as described herein can provide standardized, consistent health and wellness data that can be used by hospitals, medical researchers, doctors, and end-users.

Numerous specific details are set forth in order to provide a thorough understanding of the present invention. However, it will become obvious to those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

In the foregoing description, reference to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

The many features and advantages of the present invention are apparent from the written description. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

What is claimed is:

1. A non-transitory computer readable storage medium of a handheld sensing apparatus configured to receive a sensing strip that is configured for single use,
the handheld sensing apparatus comprising:
a computing device;

a display; and
connection terminals; and
the sensing strip comprising:
a first water-impermeable layer;
a second water-impermeable layer;
a first conductive line having a first end and a second end; and
a second conductive line having a first end and a second end,
wherein the first conductive line and the second conductive line are configured to be separated from one another,
wherein at least a portion of the first conductive line and at least a portion of the second conductive line are configured to be between the first water-impermeable layer and the second water-impermeable layer,
wherein at least an area proximate to the second end of the first conductive line and an area proximate to the second end of the second conductive line are configured such that they are not covered by at least one of the first and the second water-impermeable layers,
wherein the first end of each of the first and second conductive lines are configured to be positioned proximate to at least an opening of the sensing strip,
wherein the second end of each of the first and the second conductive lines are configured to be positioned away from the at least the opening, and
wherein the at least the opening is configured to allow at least a portion of a bodily fluid of a user to get to at least the vicinity of at least the first end of the first conductive line, and at least a portion of the bodily fluid of the user to get to at least the vicinity of at least the first end of the second conductive line, and
the non-transitory computer readable storage medium comprising a plurality of instructions, when executed by at least the computing device, configured to cause the handheld sensing apparatus to:
measure at least an electrical characteristic across the first and the second conductive lines proximate to their second ends, when the connection terminals are electrically connected to first and second conductive lines proximate to their second ends, with the electrical characteristic depending on at least portions of the bodily fluid getting to at least the vicinities of at least the first ends of the first and the second conductive lines, via the at least the opening, to provide at least an indication related to a health condition of the user; and
present data, based on at least the indication, related to the health condition of the user via the display.

2. A non-transitory computer readable storage medium as recited in claim 1,
wherein the handheld sensing apparatus comprises a wireless communication component, and
wherein the plurality of instructions, when executed by at least the computing device, are configured to cause the handheld sensing apparatus wirelessly transmitting data related to the health condition of the user to another apparatus via at least the wireless communication component.

3. An electronic system at least for a health condition of a user comprising:
a sensing strip that is configured for single use comprising:
a first water-impermeable layer;
a second water-impermeable layer;
a first conductive line having a first end and a second end; and
a second conductive line having a first end and a second end,
wherein the first conductive line and the second conductive line are configured to be separated from one another,
wherein at least a portion of the first conductive line and at least a portion of the second conductive line are configured to be between the first water-impermeable layer and the second water-impermeable layer,
wherein at least an area proximate to the second end of the first conductive line and an area proximate to the second end of the second conductive line are configured such that they are not covered by at least one of the first and the second water-impermeable layers,
wherein the first end of each of the first and second conductive lines are configured to be positioned proximate to at least an opening of the sensing strip,
wherein the second end of each of the first and the second conductive lines are configured to be positioned away from the at least the opening, and
wherein the at least the opening is configured to allow at least a portion of a bodily fluid of the user to get to at least the vicinity of at least the first end of the first conductive line, and at least a portion of the bodily fluid of the user to get to at least the vicinity of at least the first end of the second conductive line; and
a handheld sensing apparatus comprising:
a computing device;
a display;
a storage medium comprising a plurality of instructions; and
connection terminals,
wherein when the sensing strip is received by the handheld sensing apparatus, and the connection terminals are electrically connected to first and second conductive lines proximate to their second ends, the plurality of instructions, when executed by at least the computing device, are configured to cause the handheld sensing apparatus to:
measure at least an electrical characteristic across the first and the second conductive lines proximate to their second ends, with the electrical characteristic depending on at least portions of the bodily fluid getting to at least the vicinities of at least the first ends of the first and the second conductive lines, via the at least the opening to provide at least an indication related to the health condition of the user; and
present data, based on at least the indication, related to the health condition of the user via the display.

4. An electronic system as recited in claim 3, wherein the health condition is related a hydration state of the user.

5. An electronic system as recited in claim 3, wherein the bodily fluid of the user includes saliva of the user.

6. An electronic system as recited in claim 3, wherein the sensing strip comprises at least an electrical component configured to provide an identification of the sensing strip.

7. An electronic system as recited in claim 3, wherein the second water-impermeable layer is configured to include at least a hole.

8. A sensing strip configured for single use at least for a health condition of a user comprising:
a first water-impermeable layer;
a second water-impermeable layer;

a first conductive line having a first end and a second end; and a second conductive line having a first end and a second end, wherein the first conductive line and the second conductive line are configured to be separated from one another, wherein at least a portion of the first conductive line and at least a portion of the second conductive line are configured to be between the first water-impermeable layer and the second water-impermeable layer, wherein at least an area proximate to the second end of the first conductive line and an area proximate to the second end of the second conductive line are configured such that they are not covered by at least one of the first and the second water-impermeable layers, wherein the first end of each of the first and second conductive lines are configured to be positioned proximate to at least an opening of the sensing strip, wherein the second end of each of the first and the second conductive lines are configured to be positioned away from the at least the opening, wherein the at least the opening is configured to allow at least a portion of a bodily fluid of the user to get to at least the vicinity of at least the first end of the first conductive line, and at least a portion of the bodily fluid of the user to get to at least the vicinity of at least the first end of the second conductive line, and wherein the sensing strip is configured to facilitate measuring at least an electrical characteristic across the first and the second conductive lines proximate to their second ends, depending on at least portions of the bodily fluid getting to at least the vicinities of at least the first ends of the first and the second conductive lines, via the at least the opening to provide at least an indication related to the health condition of the user.

9. A sensing strip as recited in claim 8, wherein the health condition is related a hydration state of the user.

10. A sensing strip as recited in claim 8, wherein the bodily fluid of the user includes saliva of the user.

11. A sensing strip as recited in claim 8, wherein the sensing strip comprises at least an electrical component configured to provide an identification of the sensing strip.

12. A sensing strip as recited in claim 8, wherein the second water-impermeable layer is configured to include at least a hole.

13. A sensing strip as recited in claim 8, wherein the sensing strip is configured to be disposable,
wherein the sensing strip includes a first end and a second end,
wherein the first ends of both the first and second conductive lines are configured to be positioned proximate to the first end of the sensing strip, and the second ends of both the first and the second conductive lines are configured to be positioned away from the first end of the sensing strip, and
wherein the sensing strip is configured to facilitate measuring at least capacitance between the first and the second conductive lines proximate to their second ends, with at least an area proximate to the first end of the sensing strip touching skin of the user, to provide at least an indication on the health condition regarding moisture level of the skin of the user.

14. A sensing strip as recited in claim 13, wherein both the first end of the first conductive line and the first end of the second conductive lines are configured to be in a shape of a spiral, with both spirals being adjacent to each other.

15. An electronic system at least for a health condition of a user comprising:
a sensing strip that is configured to be disposable comprising:
a first water-impermeable layer;
a second water-impermeable layer;
a first conductive line having a first end and a second end; and
a second conductive line having a first end and a second end,
wherein the first conductive line and the second conductive line are configured to be separated from one another,
wherein at least a portion of the first conductive line and at least a portion of the second conductive line are configured to be between the first water-impermeable layer and the second water-impermeable layer,
wherein at least an area proximate to the second end of the first conductive line and an area proximate to the second end of the second conductive line are configured such that they are not covered by at least one of the first and the second water-impermeable layers,
wherein the sensing strip includes a first end and a second end, and
wherein the first ends of both the first and second conductive lines are configured to be positioned proximate to the first end of the sensing strip, and the second ends of both the first and the second conductive lines are configured to be positioned away from the first end of the sensing strip; and
a handheld sensing apparatus comprising:
a computing device;
a storage medium comprising a plurality of instructions;
an output device; and
connection terminals,
wherein when the sensing strip is received by the handheld sensing apparatus, and the connection terminals of the handheld sensing apparatus are electrically connected to the first and second conductive lines proximate to their second ends, the plurality of instructions, when executed by at least the computing device, are configured to cause the handheld sensing apparatus to:
measure at least capacitance between the first and the second conductive lines proximate to their second ends, with at least an area proximate to the first end of the sensing strip touching skin of the user, to provide at least an indication on the health condition regarding moisture level of the skin of the user; and
present data, based on at least the indication, related to the moisture level of the skin of the user, via the output device.

16. An electronic system as recited in claim 15, wherein the data presented is related to a skin-care product for the skin of the user.

17. An electronic system as recited in claim 16, wherein the skin-care product is lotion.

* * * * *